US012667556B2

(12) United States Patent
Cady et al.

(10) Patent No.: US 12,667,556 B2
(45) Date of Patent: Jun. 30, 2026

(54) EXTENDED RELEASE INJECTABLE FORMULATIONS COMPRISING AN ISOXAZOLINE ACTIVE AGENT, METHODS AND USES THEREOF

(71) Applicant: BOEHRINGER INGELHEIM ANIMAL HEALTH USA INC., Duluth, GA (US)

(72) Inventors: Susan Mancini Cady, Yardley, PA (US); Peter Cheifetz, East Windsor, NJ (US); Izabela Galeska, Newtown, PA (US); Loic Patrick Le Hir de Fallois, Hopewell, NJ (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 203 days.

(21) Appl. No.: 17/327,929

(22) Filed: May 24, 2021

(65) Prior Publication Data

US 2021/0299104 A1 Sep. 30, 2021

Related U.S. Application Data

(63) Continuation of application No. 15/092,491, filed on Apr. 6, 2016, now abandoned.

(60) Provisional application No. 62/144,871, filed on Apr. 8, 2015.

(51) Int. Cl.

*A61K 31/42* (2006.01)
*A61K 9/00* (2006.01)
*A61K 31/422* (2006.01)
*A61K 47/10* (2017.01)
*A61K 47/22* (2006.01)

(52) U.S. Cl.

CPC ................ *A61K 31/42* (2013.01); *A61K 9/00* (2013.01); *A61K 9/0019* (2013.01); *A61K 31/422* (2013.01); *A61K 47/10* (2013.01); *A61K 47/22* (2013.01)

(58) Field of Classification Search

CPC ..... A61K 9/0019; A61K 31/42; A61K 31/422
See application file for complete search history.

(56) References Cited

U.S. PATENT DOCUMENTS 6,733,767 B2 5/2004 Chern et al.
8,187,640 B2 5/2012 Dunn
8,362,086 B2 1/2013 Soll et al.
8,410,153 B2 * 4/2013 Lahm ..................... A01N 43/80 514/378
2002/0064547 A1 * 5/2002 Chern .................. A61K 9/0024 424/422
2004/0018238 A1 1/2004 Shukla
2007/0042013 A1 * 2/2007 Soll ......................... A61P 43/00 424/405
2010/0254959 A1 10/2010 Ahm et al.
2011/0245274 A1 10/2011 Nanchen et al.
2013/0095126 A1 4/2013 Perret et al.
2013/0116178 A1 5/2013 Lambert
2013/0131016 A1 5/2013 Akama et al.
2013/0137735 A1 5/2013 Currie
2013/0143956 A1 6/2013 Cady et al.
2013/0324538 A1 12/2013 Gauvry et al.
2013/0345221 A1 12/2013 Gauvry et al.
2015/0057321 A1 2/2015 Alteheld et al.

FOREIGN PATENT DOCUMENTS

WO 2011075591 A1 6/2011
WO 2013039948 A1 3/2013
WO 2014039475 A1 3/2014
WO 2015048371 A1 4/2015
WO WO 2015/048371 * 4/2015

OTHER PUBLICATIONS

Letendre et al. (Veterinary Parasitology (2014) 201:190-197). (Year: 2014).*
Susanne Kilp et al., "Pharmacokinetics of fluralaner in dogs following a single oral or intravenous administration", Parasites & Vectors, vol. 7, No. 1, Mar. 7, 2014, pp. 1-5.
Hirenkumar K. Makadia et al., "Poly Lactic-co-Glycolic Acid (PLGA) as Biodegradable Controlled Drug Delivery Carriers", NIH Public Access Manuscript, published in final form in Polymers, vol. 3, No. 4, Aug. 26, 2011, pp. 1377-1397.
A. Hatefi et al., "Biodegradable injectable in situ forming drug delivery systems", Journal of Controlled Release, vol. 80, No. 1-3, Apr. 23, 2002., pp. 9-28.
Y. Shi et al., "Recent advances in intravenous delivery of poorly water-soluble compounds", Expert Opinion on Drug Delivery, Informa Healthcare, GB, vol. 6, No. 12, Jan. 1, 2009.
C. Matschke et al., "Sustained-release injectables formed in situ and their potential use for veterinary products", Journal of Controlled Release, vol. 85, No. 1-3, Dec. 13, 2002, pp. 1-15.
Maria Tobio et al., "A novel system based on poloxamer/PLGA blend as a tetanus toxoid delivery vehicle", Pharmaceutical Research, vol. 16, No. 5, 1999, pp. 682-688.
Tetsuji Yamaoka et al, "Novel adhesion prevention membrane based on a bioresorbable copoly(ester-ether) comprised of poly-L-lactide and Pluronict: In vitro and in vivo evaluations", Journal of Biomedical Material Research, 2000, 54(4), pp. 470-479.
Letendre et al. "The Intravenous and Oral Pharmacokinetics of Afoxolaner Used as a a Monthly Chewable Antiparasitic for Dogs", Veterinary Parasitology, vol. 201, 2014, pp. 190-197.

(Continued)

*Primary Examiner* — Marcos L Sznaidman
(74) *Attorney, Agent, or Firm* — Katrina Bergbauer

(57) ABSTRACT

This invention relates to extended release injectable formulations for combating parasites in animals, comprising at least one isoxazoline active agent, a pharmaceutically acceptable polymer, and a solvent. This invention also provides for improved methods for eradicating, controlling, and preventing parasite infections and infestations in an animal comprising administering the extended release injectable formulations of the invention to the animal in need thereof.

27 Claims, No Drawings

(56) References Cited

OTHER PUBLICATIONS

Mansour, H.M. et al. "Materials for Pharmaceutical Dosage Forms: Molecular Pharmaceutics and Controlled Release Drug Delivery Aspects", Int. J. Mol.Sci., vol. 11, Sep. 15, 2010, pp. 3298-3322.

Beugnet, Frédéric, et al. "Afoxolaner against fleas: immediate efficacy and resultant mortality after short exposure on dogs." Parasite 21 (2014).

* cited by examiner

EXTENDED RELEASE INJECTABLE FORMULATIONS COMPRISING AN ISOXAZOLINE ACTIVE AGENT, METHODS AND USES THEREOF

CROSS REFERENCE TO RELATED APPLICATIONS

This application is a continuation application of U.S. patent application Ser. No. 15/092,491, filed Apr. 6, 2016, which claims the benefit of U.S. Provisional Application No. 62/144,871, filed on Apr. 8, 2015, both of which are incorporated herein by reference, in their entirety.

FIELD OF THE INVENTION

The present invention provides extended release injectable formulations comprising at least one isoxazoline active agent, a pharmaceutically acceptable polymer and a solvent; the use of these formulations against parasites (including ectoparasites (e.g., fleas or ticks) and/or endoparasites), and methods for preventing or treating parasitic infections and infestations in animals.

BACKGROUND OF THE INVENTION

Animals such as mammals and birds are often susceptible to parasite infestations/infections. These parasites may be ectoparasites, such as fleas, ticks and parasitic flies, and endoparasites such as nematodes and other worms. Domesticated animals, such as cats and dogs, are often infested with one or more of the following ectoparasites:

- fleas (e.g. *Ctenocephalides* spp., such as *Ctenocephalides felis* and the like);
- ticks (e.g. *Rhipicephalus* spp., *Ixodes* spp., *Dermacentor* spp., *Amblyomma* spp., and the like);
- mites (e.g. *Demodex* spp., *Sarcoptes* spp., *Otodectes* spp., and the like);
- lice (e.g. *Trichodectes* spp., *Cheyletiella* spp., *Linognathus* spp. and the like);
- mosquitoes (*Aedes* spp., *Culex* spp., *Anopheles* spp. and the like); and
- flies (*Haematobia* spp., *Musca* spp., *Stomoxys* spp., *Dermatobia* spp., *Cochlomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals. Major diseases which may be transmitted by ticks include borreliosis (Lyme disease caused by *Borrelia burgdorferi*), babesiosis (or piroplasmosis caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. A parasite which is prevalent among cattle in some regions are ticks of the genus *Rhipicephalus*, especially those of the species *microplus* (cattle tick), *decoloratus* and *annulatus*. Ticks such as *Rhipicephalus*

*microplus* (formerly *Boophilus microplus*) are difficult to control because they lay eggs in the pasture where farm animals graze.

This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesiosis ("cattle fever") and anaplasmosis.

Animals and humans also suffer from endoparasitic infections including, for example, helminthiasis, which is caused by of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting companion animals and poultry. Other parasites which occur in the gastrointestinal tract of animals and humans include those from the genus *Ancylostoma, Necator, Ascaris, Strongyloides, Trichinella, Capillaria, Toxocara, Toxascaris, Trichuris, Enterobius* and parasites which are found in the blood or other tissues and organs such as filarial worms and the extra intestinal stages of *Strongyloides, Toxocara* and *Trichinella.*

Recently, isoxazole and isoxazoline-containing compounds have been demonstrated to be effective against parasites that harm animals. For example, U.S. Pat. No. 7,964,204 (to DuPont, incorporated by reference herein in its entirety) discloses isoxazoline compounds according to Formula (I) below, which are active against ectoparasites and/or endoparasites.

(I)

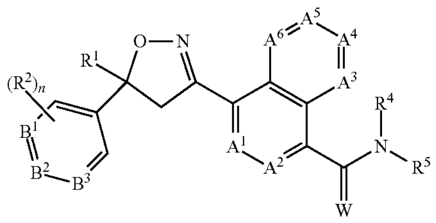

In addition, published patent application nos. US 2010/0254960 A1, WO 2007/070606 A2, WO 2007/123855 A2, WO 2010/003923 A1, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1 and WO 2007/075459 A2 and U.S. Pat. Nos. 7,951,828 and 7,662,972 describe various other parasiticidal isoxazoline compounds. Other published patent applications that describe various other parasiticidal isoxazoline compounds and formulations comprising the same include WO 2007/079162 A1, WO 2008/154528 A1, WO 2009/002809 A2, WO 2011/149749 A1, WO 2014/439475 A1, U.S. Pat. No. 8,466,115, WO 2012/120399, WO 2014/039484, WO 2014/189837, (Zoetis) and WO2012 120135A1 (Novartis). WO 2012/089623 describes topical localized isoxazoline formulations comprising glycofurol. WO 2013/039948 A1 provides for topical veterinary compositions comprising at least one isoxazoline active agent and WO 2013/119442 A1 provides for oral veterinary compositions such as a soft chew, which comprise at least one isoxazoline active agent.

In addition to topical and oral dosage forms, it is sometimes possible to formulate active agents as extended release injectable formulations, depending upon, for example, the physiochemical properties of the individual active agent. These properties include, for example, solubility, bioavailability, etc. In some cases it may be possible to formulate active agents in extended release formulations comprising a pharmaceutically acceptable polymer that controls the release of the active agent in the animal's body from the formulation over an extended period of time. The meaning of "extended release" formulations in the veterinary medicine field is the subject of the article "*Terminology Challenges: Defining Modified Release Dosage Forms in Veterinary Medicine*" by Marilyn N. Martinez, Danielle Lindquist and Sanja Modric (Journal of Pharmaceutical Sciences, vol. 99, no. 8, August 2010). The definition for an "extended release" dosage form proposed in the article "Dosage forms that are formulated in such a manner as to make the contained medicament available over an extended period of time" is consistent with the use of this term in the present application in which the formulation components induce the release characteristics of the active ingredient rather than the intrinsic properties of the active itself being responsible for the long acting nature of the formulation. For example, U.S. Pat. Nos. 6,733,767 and 8,362,086 provide for long acting injectable formulations comprising a bioactive substance, such as, for example, an avermectin or a milbemycin and a biologically acceptable polymer. U.S. Pat. No. 5,330,768 provides for degradable polymeric matrices for the delivery of drugs by blending polymers that degrade by hydrolysis (e.g., poly(L-lactic acid), nonionic surfactants and block copolymers of polyethylene oxide and polypropylene oxide.

Fluorinated compounds, such as the some of the isoxazoline compounds provided for in the inventive formulations, often present additional challenges as compared to their non-fluorinated counterparts when formulating the compounds in extended release injectable formulations because the presence of fluorine groups make it more difficult to achieve the desired release properties of the compound from the polymeric matrices, which form the depot.

Fluorinated organic compounds are very hydrophobic. In part, this is due to the low surface energies which make the compound less wettable. See, N. L. Jarvis and W. A. Zisman, "Surface Chemistry of Fluorochemicals", U.S. Naval Research Laboratory, Washington, D.C. (1965). This property hinders the hydration of polymers such as poly(L-lactic acid), thereby delaying the degradation of the polymer and delaying the release of the fluorinated compound from the depot.

Notwithstanding the compositions comprising isoxazoline active agents alone or in combination with other active agents described in the documents above, there is a need for veterinary compositions and methods with improved duration of efficacy, and/or bioavailability, and/or spectrum of coverage to protect animals against endoparasites and/or ectoparasites. More specifically, there is a need to develop a longer acting injectable formulation comprising an isoxazoline compound, which has good bioavailability and provides a high level of efficacy against ectoparasites (e.g., fleas and ticks) for a long duration (e.g., from three (3) up to twelve (12) months, while exhibiting reduced injection site irritation on the animal.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention provides novel and inventive extended release injectable formulations for the treatment or prevention of parasite infections or infestations in an animal comprising an antiparasitic effective amount of at least one isoxazoline active agent, a pharmaceutically acceptable polymer and, optionally, a solvent. In an embodiment, the extended release injectable formulations of the invention comprise an antiparasitic effective amount of at least one isoxazoline active agent, a pharmaceutically acceptable biodegradable polymer, and a solvent. As used herein, the term "poloxamer" means a block copolymer of ethylene oxide and propylene oxide. For the purpose of the present application poloxamers that are not co-polymerized with other pharmaceutically acceptable polymers are considered solvents or surfactants rather than a pharmaceutically acceptable polymer. Different grades, sources, and brands of block copolymers of ethylene oxide and propylene oxide may be used in the extended release injectable formulations of the invention. Likewise, for the purposes of this application, liquid polyethylene glycols (PEGs) that are not co-polymerized with other pharmaceutically acceptable polymers are considered to be a solvent and are not considered to be a pharmaceutically acceptable polymer In accordance with this invention, it has been discovered that the inventive extended release injectable formulations generally show desirable bioavailability and duration of efficacy.

Further, the inventive extended release formulations generally do not show undesirable irritation on the injection site of the animal. The compositions also provide desirable safety profiles toward the warm-blooded and avian animal recipients. In addition, it has been discovered that a single administration of such formulations generally provides potent activity against one or more parasites (e.g., ectoparasites), while also tending to provide fast onset of activity, long duration of activity, and/or desirable safety and release profiles.

The invention encompasses uses or veterinary uses of the isoxazoline compositions for the treatment or prevention or prophylaxis of parasitic infections and infestations of animals (either wild or domesticated), including livestock and companion animals such as cats, dogs, horses, chickens, sheep, goats, pigs, turkeys and cattle, with the aim of ridding these hosts of parasites commonly encountered by such animals.

The invention also provides methods for the treatment or prevention of parasitic infections and infestations in animals, comprising administering an effective amount of extended release injectable formulations comprising an antiparasitic effective amount of at least one isoxazoline compound together with a pharmaceutically acceptable polymer and a solvent.

Surprisingly, it has been found that the inventive isoxazoline-containing extended release injectable formulations described herein exhibit superior broad spectrum efficacy against harmful parasites (e.g. ectoparasites such as fleas and ticks) more rapidly, and over a long duration compared to other injectable formulations containing isoxazoline active agents known in the art while exhibiting acceptable irritation injection site characteristics.

This invention also provides for the use of an isoxazoline in the preparation of extended release injectable formulations for the treatment or prevention of an animal against parasites.

In one embodiment, the invention provides for extended release injectable formulations comprising antiparasitic effective amounts of at least one isoxazoline of formula (I) below, in combination and a pharmaceutically or veterinary acceptable polymer and a solvent, where variables $B^1$, $B^2$, $B^3$, $R^1$, Y and Q are defined herein and the asterisk signifies that the carbon is a quaternary carbon.

(I)

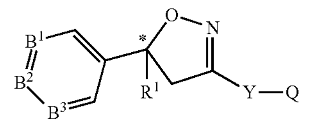

In other embodiments, the extended release injectable formulations of the invention comprise effective amounts of at least one isoxazoline active agent of formulae (II)

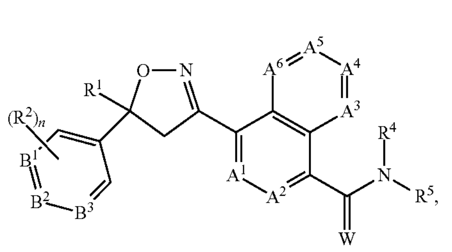

(III)

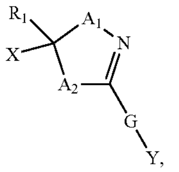

(IV)

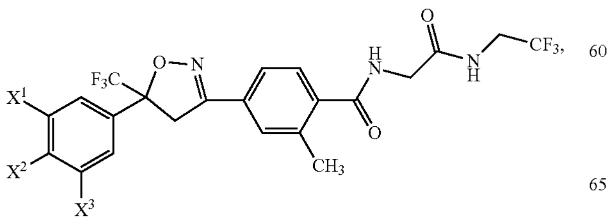

-continued (V)

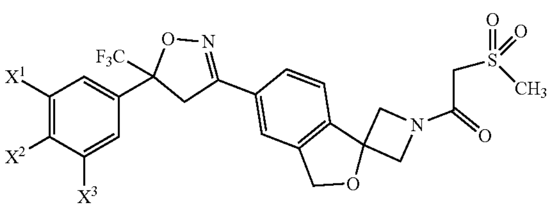

(VI)

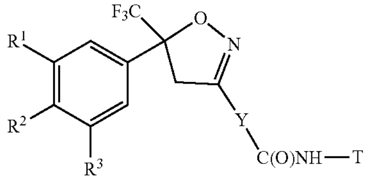

or (VII)

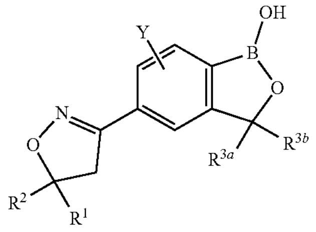

wherein variables $A^1$, $A^2$, $A^3$, $A^4$, $A^5$, $A^6$, $B^1$, $B^2$, $B^3$, $R^1$, $R^2$, $R^3$, $R^4$, $R^5$, W, n, $X^1$, $X^2$, $X^3$, $R_1$, X, $A_1$, $A_2$, G, Y, T, $R^{3a}$ and $R^{3b}$ for each formula are defined herein.

In some embodiments, the extended release injectable formulations and methods comprise 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide (compound of Formula IIc) as the active agent. These compounds are described in U.S. Pat. Nos. 7,964,204 B2 and 8,410,153 B2, both incorporated herein by reference in their entirety.

In other embodiments, the extended release injectable formulations may further comprise one or more additional active agents that are systemically active. Systemically-acting active agents include, but are not limited to, isoxazoline active agents of different structure, a systemically-acting neonicotinoid active agent, a systemically-acting 1-N-arylpyrazole active agent, macrocyclic lactones such as avermectin and milbemycin compounds, a cyclic depsipeptide such as emodepside or PF1022A, or analogs thereof, benzimidazoles, imidazothiazoles, a tetrahydropyrimidine active agent, an organophosphate active agent, levamisole, a paraherquamide active agent and/or a marcfortine active agent, praziquantel, closantel, clorsulon, pyrantel, a spinosyn or spinosoid active agent, an amino acetonitrile active agent, an aryloazol-2-yl cyanoethyl active agent and a systemically-acting insect growth regulator. In one embodiment, the extended release injectable formulations comprise at least one macrocyclic lactone active agent, including, but not limited to, avermectins or milbemycins. In some embodiments, the avermectin or milbemycin active agent is eprinomectin, ivermectin, abamectin, selamectin, doramectin, milbemectin, milbemycin D, milbemycin oxime, or moxidectin.

In other embodiments, the compositions and methods comprise at least one of thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, or an aryloazol-2-yl cyanoethylamino active agent.

In yet another embodiment, the compositions and methods comprise at least cyclic depsipeptide active agent including, but not limited to, emodepside and PF1022A, or analogs thereof.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

DETAILED DESCRIPTION

The present invention provides for novel and inventive extended release injectable formulations treatment or prevention of parasite infections or infestations in an animal comprising an antiparasitic effective amount of at least one isoxazoline compound, a pharmaceutically acceptable polymer and optionally a solvent or mixture of solvents.

Also provided are methods and uses for the treatment and/or prophylaxis of parasitic infections and infestations of animals, comprising administering to an animal in need thereof an extended release formulation comprising an antiparasitic effective amount of at least one isoxazoline compound, a pharmaceutically acceptable polymer and optionally a solvent or mixture of solvent.

In another embodiment, the present invention provides for extended release injectable formulations for the treatment and/or prophylaxis of parasitic infections and infestations of animals comprising an antiparasitic effective amount of at least one isoxazoline compound and an effective amount of at least one additional systemically-acting active agent, a pharmaceutically acceptable polymer and, optionally, a solvent or mixture of solvent.

In a preferred embodiment of the invention, the pharmaceutically acceptable polymer is a pharmaceutically acceptable biodegradable polymer.

In one embodiment, the present invention provides for an extended release injectable formulations for the treatment and/or prophylaxis of parasitic infections and infestations of animals comprising:

a) an antiparasitic effective amount of at least one isoxazoline active agent, which is:
   i) an isoxazoline compound of formula (I):

(I)

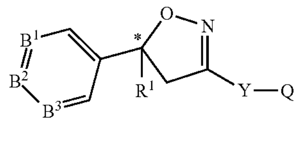

wherein:

$B^1$, $B^2$ and $B^3$ are each independently C—R or N;

each R is independently H, halogen, cyano, —$NO_2$, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino or alkoxycarbonyl;

$R^1$ is $C_1$-$C_3$alkyl or $C_1$-$C_3$haloalkyl;

Y is an optionally substituted phenylene, naphthylene, indanylene, a 5- or 6-membered heteroarylene or an 8-10-membered fused heterobicyclylene, wherein the optional substituents are selected from the group consisting of halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN or —$NO_2$ and $NH_2$—C(═S)—;

Q is X—$NR^2R^3$, the group (—$CH_2$—)(—$CH_2$—)N—$R^3$, OH, $NH_2$, alkoxy, haloalkoxy, alkylamino, haloalkylamino, dialkylamino, halodialkylamino, thiol, alkylthio, haloalkylthio, alkylsulfinyl, haloalkylsulfinyl, alkylsulfonyl, haloalkylsulfonyl, or an optionally substituted 5- or 6-membered carbocyclyl, heterocyclyl or heteroaryl ring;

X is $(CH_2)_n$, $CH(CH_3)$, CH(CN), C(═O) or C(═S);

$R^2$ is H, alkyl, alkenyl, alkynyl, cycloalkyl, alkylcycloalkyl, cycloalkylalkyl, alkylcarbonyl or alkoxycarbonyl;

$R^3$ is H, $OR^7$, $NR^8R^9$ or $Q^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^4$; or $R^2$ and $R^3$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;

each $R^4$ is independently halogen; alkyl, cycloalkyl, alkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —$NH_2$, —CN or —$NO_2$; or $Q^2$ each $R^5$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —$NO_2$;

each $R^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN, —$NO_2$, phenyl or pyridinyl;

$R^7$ is H; or alkyl, alkenyl, alkynyl, cycloalkyl, alkylcycloalkyl or cycloalkylalkyl, each optionally substituted with one of more halogen;

$R^8$ is H, alkyl, alkenyl, alkynyl, cycloalkyl, alkylcycloalkyl, cycloalkylalkyl, alkylcarbonyl or alkoxycarbonyl;

$R^9$ is H; $Q^3$; or alkyl, alkenyl, alkynyl, cycloalkyl, alkylcycloalkyl or cycloalkylalkyl, each optionally substituted with one or more substituents independently selected from $R^4$; or $R^8$ and $R^9$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^5$;

$Q^2$ is independently a phenyl ring or a 5- or 6-membered heterocyclic ring, each ring optionally substituted with one or more substituents independently selected from $R^6$;

$Q^3$ is a phenyl ring or a 5- or 6-membered heterocyclic ring, each ring optionally substituted with one or more substituents independently selected from $R^6$; and n is 0, 1 or 2;

b) at least one pharmaceutically acceptable polymer;
c) at least one pharmaceutically acceptable solvent;
d) optionally, an antioxidant;
e) optionally a surfactant; and
f) optionally at least one pharmaceutically acceptable additive, excipient or mixtures thereof.

In one embodiment of the invention directed to extended release compositions comprising an isoxazoline compound of formula (I), Y is selected from Y-1, Y-2, Y-3, Y-4 where Z is nitrogen or CH, Y-5 or Y-6 shown below:

Y-1

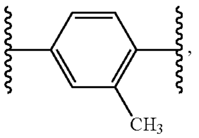

Y-2

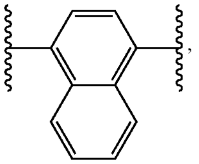

Y-3

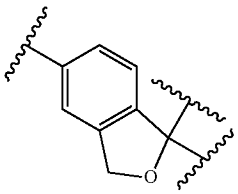

Y-4

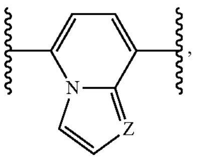

-continued

Y-5

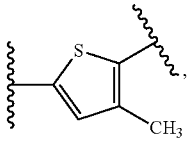

Y-6

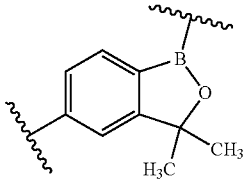

In one embodiment of the invention comprising an isoxazoline compound of formula (I), the group Q is X—$NR^2R^3$. In another embodiment, Q is X—$NR^2R^3$ wherein $R^2$ is H or $C_1$-$C_3$alkyl and $R^3$ is $C_1$-$C_3$alkyl optionally substituted by $R^4$. In yet another embodiment, Q is X—$NR^2R^3$ wherein $R^2$ is H and $R^3$ is $C_1$-$C_3$alkyl optionally substituted by alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl. In another embodiment, Q is X—$NR^2R^3$ wherein $R^2$ is H and $R^3$ is $C_1$-$C_3$alkyl optionally substituted by alkylthio, haloalkylthio, alkylaminocarbonyl, dialkylaminocarbonyl, haloalkylaminocarbonyl or dihaloalkylaminocarbonyl. In still another embodiment, Q is —C(O)$NHCH_2C(O)NHCH_2CF_3$. In yet another embodiment, Q is —C(O)$CH_2S(O)_2CH_3$. In another embodiment, Q is —C(O)$NHCH_2CH_2SCH_3$. In another embodiment, Q is the group (—$CH_2$—)($CH_2$—)N(CO)$CH_2S(O)_2CH_3$.

In another embodiment, the present invention provides for an extended release injectable formulations for the treatment and/or prophylaxis of parasitic infections and infestations of animals comprising:

a) an antiparasitic effective amount of at least one isoxazoline active agent, which is:
   i) an isoxazoline compound of formula (I):

(II)

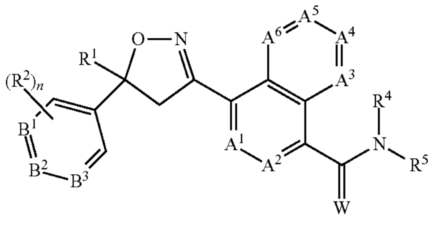

wherein:

$A^1$, $A^2$, $A^3$, $A^4$, $A^5$ and $A^6$ are independently selected from the group consisting of $CR^3$ and N, provided that at most 3 of $A^1$, $A^2$, $A^3$, $A^4$, $A^5$ and $A^6$ are N;

$B^1$, $B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, CN or $NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2; or a pharmaceutically acceptable salt thereof, and/or ii) an isoxazoline compound of formula (III):

(III)

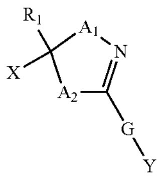

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$A_1$ is oxygen; and $A_2$ is oxygen, $NR_2$ or $CR_7R_8$;

G is G-1 or G-2;

G-1

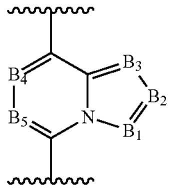

-continued

G-2

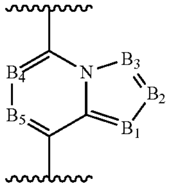

$B^1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13;

Y-1

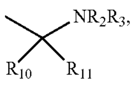

Y-2

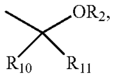

Y-3

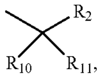

Y-4

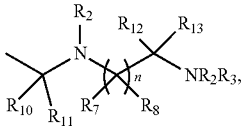

Y-5

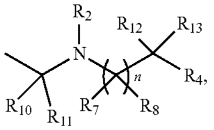

Y-6

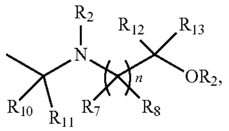

Y-7

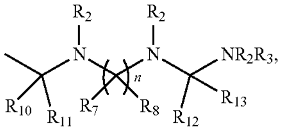

Y-8

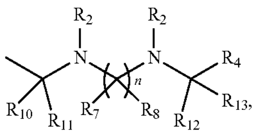

-continued

Y-9

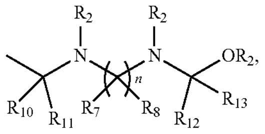

Y-10

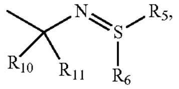

Y-11

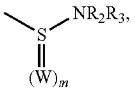

Y-12

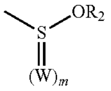

or

Y-13

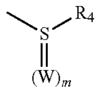

$R_2$, $R_3$ are independently hydrogen, alkyl, haloalkyl, thioalkyl, alkylthioalkyl, hydroxyalkyl, alkoxyakyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$—$R_{10}OC(O)$—;

$R_4$, $R_5$ and $R_6$ are independently hydrogen, alkyl, haloalkyl, thioalkyl, alkylthioalkyl, hydroxyalkyl, alkoxyakyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxyakyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxyalkyl, alkenyl, haloalkenyl, alkynyl or haloalkynyl; or $R_{10}$ together with $R_{11}$ form =O, =S or =$NR_2$; or $R_{12}$ together with $R_{13}$ form =O, =S or =$NR_2$;

W is O, S or $NR_2$;

n is 1-4; and m is 0, 1 or 2; or a pharmaceutically acceptable salt thereof, and/or iii) an isoxazoline compound of formula (IV)

(IV)

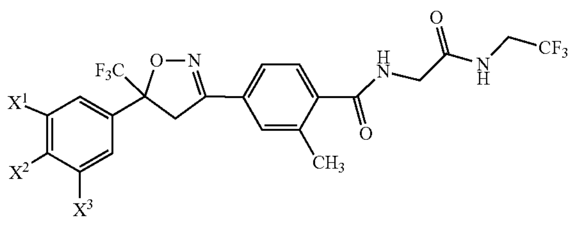

wherein $X^1$, $X^2$ and $X^3$ are independently H, halogen, $C_1$-$C_3$alkyl or $C_1$-$C_3$haloalkyl, or a pharmaceutically acceptable salt thereof; and/or iv) an isoxazoline compound of formula (V)

(V)

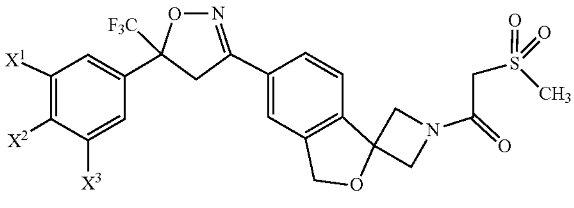

wherein $X^1$, $X^2$ and $X^3$ are independently H, halogen, $C_1$-$C_3$alkyl or $C_1$-$C_3$haloalkyl, or a pharmaceutically acceptable salt thereof; and/or v) an isoxazoline compound of formula (VI):

(VI)

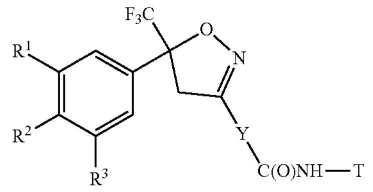

wherein $R^1$, $R^2$ and $R^3$ are independently H, Cl, F or $CF_3$;

Y is the diradical group

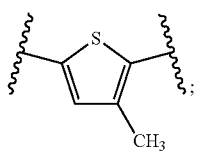 [SMILES: *c1cc(C)c(*)s1]

;

and

T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof; and/or vi) an isoxazoline compound of formula (VII):

(VII)

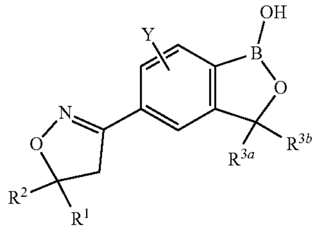

wherein Y is hydrogen, fluoro, chloro or bromo;

$R^1$ is phenyl substituted with 2-4 substituents selected from halogen, methyl, difluoromethyl, trifluoromethyl, methoxy, trifluoromethoxy or trifluoroethoxy;

$R^2$ is methyl, fluoromethyl, trifluoromethyl or perfluoroethyl;

$R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally at least one pharmaceutically acceptable additive, excipient or mixtures thereof.

The compound of formula (III) is disclosed in U.S. Pat. No. 7,662,972 and in published U.S. Patent Application No. US 2011/0059988 A1, both incorporated herein by reference. The compound of formula (IV) is disclosed in U.S. Pat. No. 8,466,115 B2, which is incorporated herein by reference. The compound of formula (VI) is described in U.S. Pat. No. 8,383,659, which is also incorporated herein by reference. The compound of formula (VII) is described in U.S. Pat. No. 8,853,186 B2, which is incorporated herein by reference.

In another embodiment, the present invention provides for extended release injectable formulations for the treatment and/or prevention (prophylaxis) of parasitic infections and infestations of animals comprising:

a) an antiparasitic effective amount of at least one isoxazoline compound of formula (II):

(II)

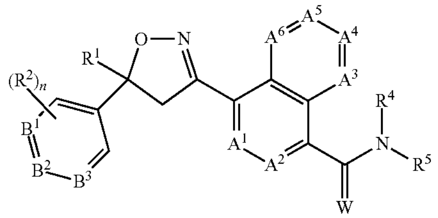

wherein:

$A^1$, $A^2$, $A^3$, $A^4$, $A^5$ and $A^6$ are independently selected from the group consisting of $CR^3$ and N, provided that at most 3 of $A^1$, $A^2$, $A^3$, $A^4$, $A^5$ and $A^6$ are N;

$B^1$, $B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl; $R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, CN or $NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2 or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of an isoxazoline compound of formula (IIa):

(IIa)

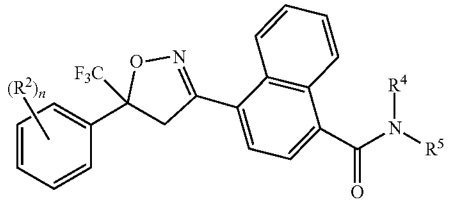

or a pharmaceutically acceptable salt thereof wherein $R^2$ independently is halogen, $C_1$-$C_6$ alkyl or $C_1$-$C_6$ haloalkyl $R^4$ is H or $C_1$-$C_6$ alkyl;

$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl (e.g., —$CH_2C(O)NHCH_2CF_3$); and n is 0, 1 or 2 or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for an extended release injectable formulations for the treatment and/or prophylaxis of parasitic infections and infestations of animals comprising:

a) an antiparasitic effective amount of an isoxazoline active agent of formula (IIb)

(IIb)

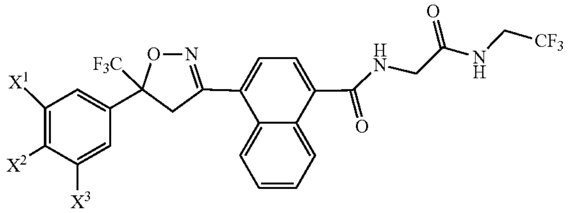

wherein $X^1$, $X^2$ and $X^3$ are each independently H, halogen, $C_1$-$C_3$alkyl or $C_1$-$C_3$haloalyl or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of an isoxazoline compound of formula (IIc):

(IIc)

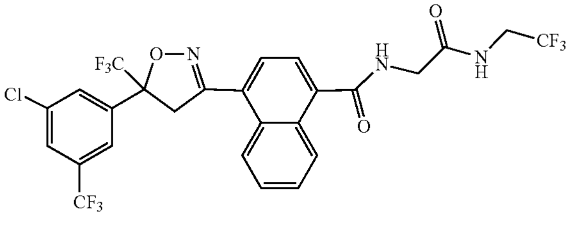

or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of an isoxazoline compound of formula (IId):

(IId)

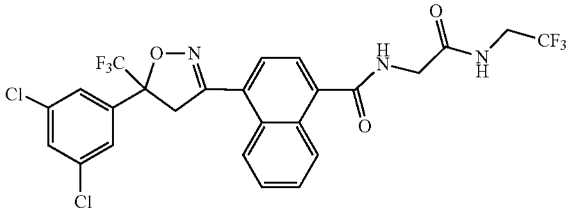

or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of an isoxazoline compound of formula (IIe):

(IIe)

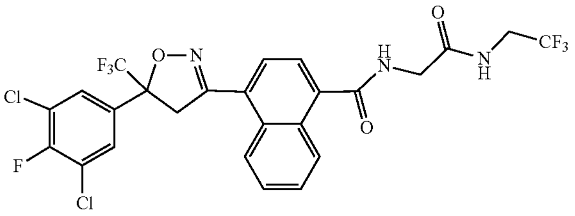

or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of an isoxazoline compound of formula (IIf):

(IIf)

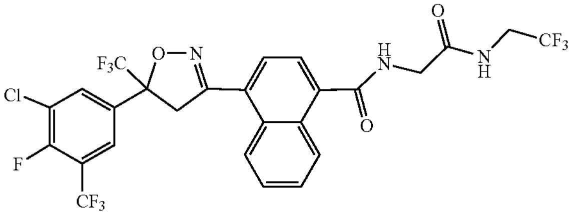

or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of at least one isoxazoline compound of formula (III):

(III)

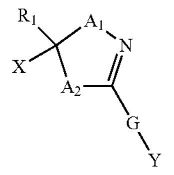

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$A_1$ is oxygen; and $A_2$ is oxygen, $NR_2$ or $CR_7R_8$;

G is G-1 or G-2;

G-1

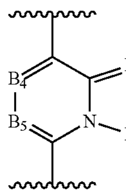

G-2

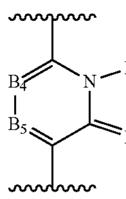

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13;

Y-1

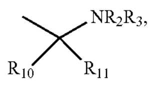

Y-2

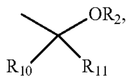

Y-3

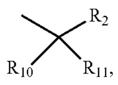

Y-4

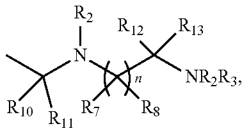

Y-5

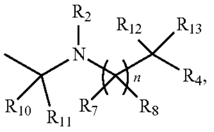

Y-6

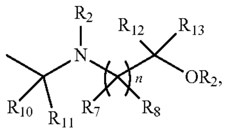

Y-7

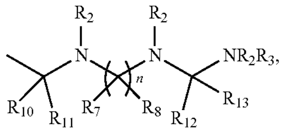

Y-8

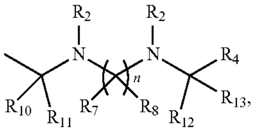

Y-9

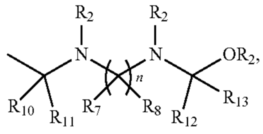

Y-10

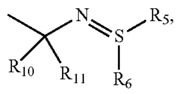

Y-11

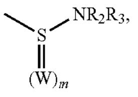

-continued

Y-12

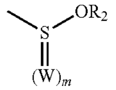

or

Y-13

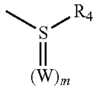

$R_2$, $R_3$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$—$R_{10}OC(O)$—;

$R_4$, $R_5$ and $R_6$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxyalkyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl) amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxyalkyl, alkenyl, haloalkenyl, alkynyl or haloalkynyl; or $R_{10}$ together with $R_{11}$ form =O, =S or =$NR_2$; or $R_{12}$ together with $R_{13}$ form =O, =S or =$NR_2$;

W is O, S or $NR_2$;

n is 1-4; and m is 0, 1 or 2; or a pharmaceutically acceptable salt thereof, b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of at least one isoxazoline compound of formulae III-1.001 to III-1.025 and III-2.001-III-2.018:

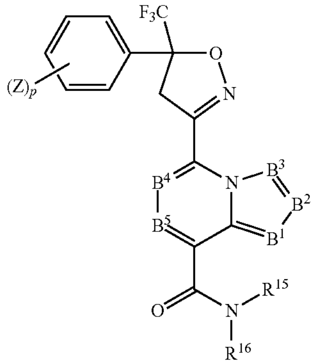

Compounds III-1.001 to III-1.025

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 1.001 | 3,5-$Cl_2$ | C—H | C—H | C—H | C—H | N | H | $CH_2C(O)NHCH_2CF_3$ |
| 1.002 | 3,5-$Cl_2$ | C—H | C—H | C—H | C—H | N | H | $CH_2CF_3$ |
| 1.003 | 3,5-$(CF_3)_2$ | C—H | C—H | C—H | C—H | N | $CH_3$ | $CH_2CO_2CH_3$ |
| 1.004 | 3,5-$(CF_3)_2$ | C—H | C—H | C—H | C—H | N | $CH_3$ | $CH_2CO_2H$ |
| 1.005 | 3,5-$(CF_3)_2$ | C—H | C—H | C—H | C—H | N | $CH_3$ | $CH_2C(O)NHCH_2CF_3$ |
| 1.006 | 3,5-$(CF_3)_2$ | C—H | C—H | C—H | C—H | N | H | $CH_2C(O)NHCH_2CF_3$ |
| 1.007 | 3,5-$(CF_3)_2$ | C—H | C—H | C—H | C—H | N | H | $CH_2CH_2SCH_3$ |
| 1.008 | 3,5-$(CF_3)_2$ | C—H | C—H | C—H | C—H | C—H | H | $CH_2C(O)NHCH_2CF_3$ |
| 1.009 | 3,5-$(CF_3)_2$ | C—H | C—H | C—H | C—H | C—H | H | $CH_2CH_2SCH_3$ |
| 1.010 | 3,5-$(CF_3)_2$ | C—H | C—H | C—H | C—H | C—H | H | $CH_2CF_3$ |
| 1.011 | 3,5-$Cl_2$ | C—H | C—H | C—H | C—H | C—H | H | $CH_2C(O)NHCH_2CF_3$ |
| 1.012 | 3,5-$Cl_2$ | C—H | C—H | C—H | C—H | C—H | H | $CH_2CF_3$ |
| 1.013 | 3,5-$Cl_2$ | C—H | C—H | C—H | C—H | C—H | H | $CH_2CH_2SCH_3$ |
| 1.014 | 3-Cl,5-$CF_3$ | C—H | C—H | C—H | C—H | C—H | H | $CH_2C(O)NHCH_2CF_3$ |
| 1.015 | 3-Cl,5-$CF_3$ | C—H | C—H | C—H | C—H | C—H | H | $CH_2CF_3$ |
| 1.016 | 3-Cl,5-$CF_3$ | C—H | C—H | C—H | C—H | C—H | H | $CH_2CH_2SCH_3$ |
| 1.017 | 3,5-$Cl_2$ | C—H | C—H | C—Me | C—H | C—Me | H | $CH_2C(O)NHCH_2CF_3$ |
| 1.018 | 3,5-$Cl_2$ | C—H | C—H | C—Me | C—H | C—Me | H | $CH_2CF_3$ |
| 1.019 | 3,5-$Cl_2$ | C—H | C—H | C—Me | C—H | C—Me | H | $CH_2CH_2SCH_3$ |
| 1.020 | 3,5-$(CF_3)_2$ | C—H | C—H | C—Me | C—H | C—Me | H | $CH_2C(O)NHCH_2CF_3$ |
| 1.021 | 3,5-$(CF_3)_2$ | C—H | C—H | C—Me | C—H | C—Me | H | $CH_2CF_3$ |
| 1.022 | 3,5-$(CF_3)_2$ | C—H | C—H | C—Me | C—H | C—Me | H | $CH_2CH_2SCH_3$ |
| 1.023 | 3-Cl,5-$CF_3$ | C—H | C—H | C—Me | C—H | C—Me | H | $CH_2C(O)NHCH_2CF_3$ |
| 1.024 | 3-Cl,5-$CF_3$ | C—H | C—H | C—Me | C—H | C—Me | H | $CH_2CF_3$ |
| 1.025 | 3-Cl,5-$CF_3$ | C—H | C—H | C—Me | C—H | C—Me | H | $CH_2CH_2SCH_3$ |

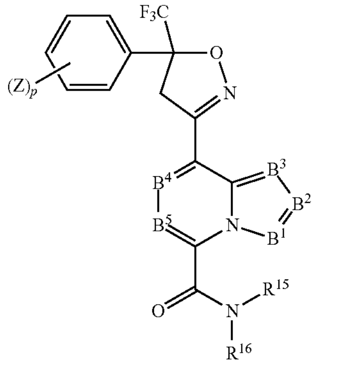

Compounds III-2.001 to III-2.018

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 2.001 | 3,5-$Cl_2$ | C—H | C—H | N | C—H | C—H | H | $CH_2C(O)NHCH_2CF_3$ |
| 2.002 | 3,5-$Cl_2$ | C—H | C—H | N | C—H | C—H | H | $CH_2CF_3$ |
| 2.003 | 3,5-$Cl_2$ | C—H | C—H | N | C—H | C—H | H | $CH_2CH_2SCH_3$ |
| 2.004 | 3,5-$(CF_3)_2$ | C—H | C—H | N | C—H | C—H | H | $CH_2C(O)NHCH_2CF_3$ |
| 2.005 | 3,5-$(CF_3)_2$ | C—H | C—H | N | C—H | C—H | H | $CH_2CF_3$ |
| 2.006 | 3,5-$(CF_3)_2$ | C—H | C—H | N | C—H | C—H | H | $CH_2CH_2SCH_3$ |
| 2.007 | 3-Cl,5-$CF_3$ | C—H | C—H | N | C—H | C—H | H | $CH_2C(O)NHCH_2CF_3$ |
| 2.008 | 3-Cl,5-$CF_3$ | C—H | C—H | N | C—H | C—H | H | $CH_2CF_3$ |
| 2.009 | 3-Cl,5-$CF_3$ | C—H | C—H | N | C—H | C—H | H | $CH_2CH_2SCH_3$ |
| 2.010 | 3,5-$Cl_2$ | C—H | C—H | C—H | C—H | C—H | H | $CH_2C(O)NHCH_2CF_3$ |
| 2.011 | 3,5-$Cl_2$ | C—H | C—H | C—H | C—H | C—H | H | $CH_2CF_3$ |
| 2.012 | 3,5-$Cl_2$ | C—H | C—H | C—H | C—H | C—H | H | $CH_2CH_2SCH_3$ |
| 2.013 | 3,5-$(CF_3)_2$ | C—H | C—H | C—H | C—H | C—H | H | $CH_2C(O)NHCH_2CF_3$ |
| 2.014 | 3,5-$(CF_3)_2$ | C—H | C—H | C—H | C—H | C—H | H | $CH_2CF_3$ |
| 2.015 | 3,5-$(CF_3)_2$ | C—H | C—H | C—H | C—H | C—H | H | $CH_2CH_2SCH_3$ |
| 2.016 | 3-Cl,5-$CF_3$ | C—H | C—H | C—H | C—H | C—H | H | $CH_2C(O)NHCH_2CF_3$ |
| 2.017 | 3-Cl,5-$CF_3$ | C—H | C—H | C—H | C—H | C—H | H | $CH_2CF_3$ |
| 2.018 | 3-Cl,5-$CF_3$ | C—H | C—H | C—H | C—H | C—H | H | $CH_2CH_2SCH_3$ |

or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of e isoxazoline compound of formula (IV)

(IV)

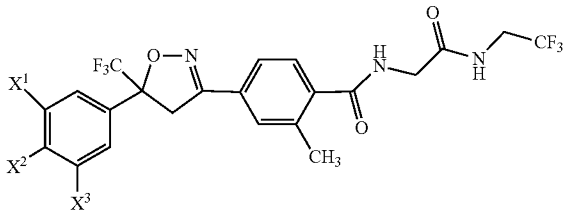

wherein $X^1$, $X^2$ and $X^3$ are independently H, halogen, $C_1$-$C_3$alkyl or $C_1$-$C_3$haloalkyl, or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of e isoxazoline compound of formula (IVa)

(IVa)

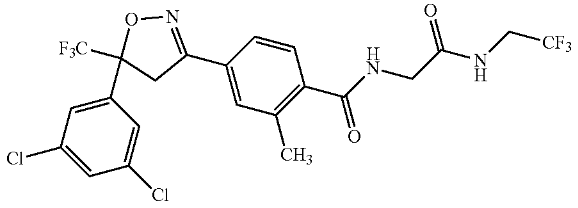

or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

iv) an antiparasitic effective amount of an isoxazoline compound of formula (V)

(V)

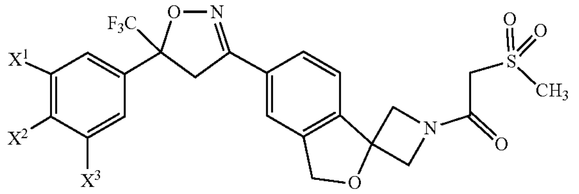

wherein $X^1$, $X^2$ and $X^3$ are independently H, halogen, $C_1$-$C_3$alkyl or $C_1$-$C_3$haloalkyl, or a pharmaceutically acceptable salt thereof;

b) at least one pharmaceutically acceptable polymer;

c) at least one pharmaceutically acceptable solvent;

d) optionally, an antioxidant;

e) optionally, a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

iv) an antiparasitic effective amount of an isoxazoline compound of formula (Va)

(Va)

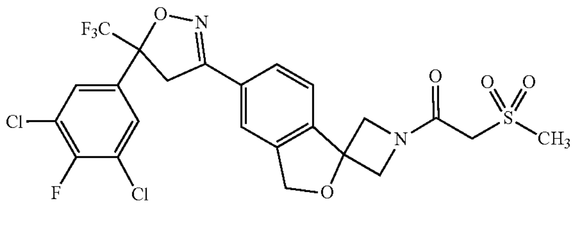

or a pharmaceutically acceptable salt thereof;

b) at least one pharmaceutically acceptable polymer;

c) at least one pharmaceutically acceptable solvent;

d) optionally, an antioxidant;

e) optionally, a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of at least one isoxazoline compound of formula (VI):

(VI)

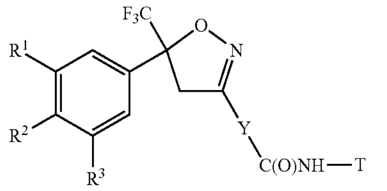

wherein $R^1$, $R^2$ and $R^3$ are independently H, Cl, F or $CF_3$; Y is the diradical group

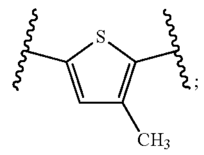

and

T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof b) at least one pharmaceutically acceptable polymer;

c) at least one pharmaceutically acceptable solvent;

d) optionally, an antioxidant; and e) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising a) an antiparasitic effective amount of an isoxazoline compound of formula (VIa):

(VIa)

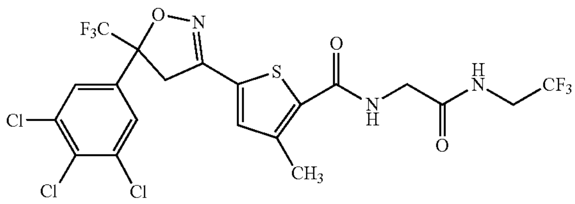

b) at least one pharmaceutically acceptable polymer;

c) at least one pharmaceutically acceptable solvent;

d) optionally, an antioxidant;

e) optionally, a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising a) an antiparasitic effective amount of at least one compound of formula (VII):

(VII)

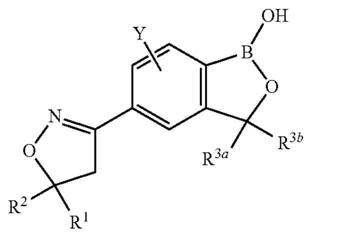

wherein

Y is hydrogen, fluoro, chloro or bromo;

$R^1$ is phenyl substituted with 2-4 substituents selected from halogen, methyl, difluoromethyl, trifluoromethyl, methoxy, trifluoromethoxy or trifluoroethoxy;

$R^2$ is methyl, fluoromethyl, trifluoromethyl or perfluoroethyl;

$R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof b) at least one pharmaceutically acceptable polymer;

c) at least one pharmaceutically acceptable solvent;

d) optionally, an antioxidant;

e) optionally, a surfactant; and f) optionally, at least one pharmaceutically acceptable additive, excipient or mixtures thereof.

In another embodiment, the present invention provides for extended release injectable formulations for the treatment and/or prevention (prophylaxis) of parasitic infections and infestations of animals comprising:

a) an antiparasitic effective amount of an isoxazoline compound of formula (VIIa):

(VIIa)

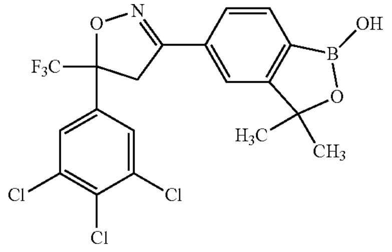

or a pharmaceutically acceptable salt thereof;

b) at least one pharmaceutically acceptable polymer;

c) at least one pharmaceutically acceptable solvent;

d) optionally, an antioxidant;

e) optionally a surfactant; and f) optionally, at least one pharmaceutically acceptable additive, excipient or mixtures thereof.

In another embodiment, the extended release injectable formulations of present invention comprise an antiparasitic effective amount of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula IIc).

In another embodiment, the pharmaceutically acceptable polymer in the extended release injectable formulations described above may be a copolymer of polylactides and polyglycolides, and the solvent may be a single solvent, such as, for example a cyclic carbonate (e.g., ethylene carbonate or propylene carbonate) or a mixture of solvents comprising, for example, a cyclic carbonate, a glycerol ester (e.g., glycerol triacetate), and, optionally, a poloxamer (for example, P-124), which can function either as a solvent or a surfactant. In yet a further embodiment, the extended release formulations described above an antioxidant is present, such as, butylated hydroxytoluene.

The compounds of formula (I) through formula (VIIa) can exist as stereoisomers since there is a chiral center in the molecule. The individual stereoisomers are encompassed by the structural formulas depicted herein. The various stereoisomers include enantiomers, diastereomers and atopisomers. One of skill in the art will understand that one stereoisomer may be more active and/or may exhibit beneficial properties relative to the other enantiomer. In addition, the skilled person in the art knows how to separate, enrich, and/or selectively prepare a stereoisomer of the isoxazoline compounds described herein. The isoxazoline compounds described herein contain a chiral quaternary carbon atom in the five-membered isoxazoline ring (shown by the asterisk (*)); therefore, the compounds will contain at least two possible stereoisomers. As an example for the compounds of formula (IIc), the two possible stereoisomers resulting from the quaternary carbon are shown as formula (R)-IIc and (S)-IIc:

(S)-IIc

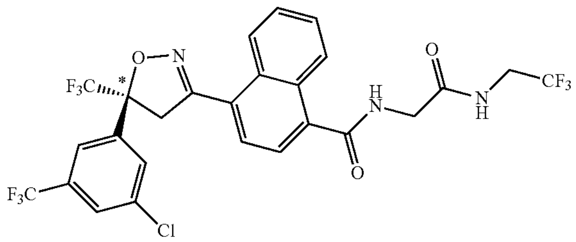

(R)-IIc

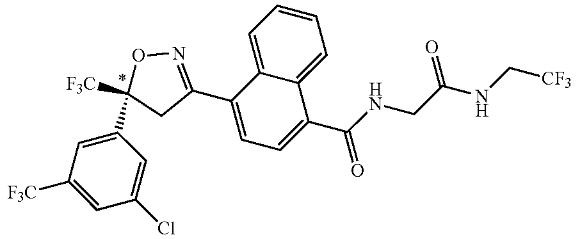

The compound of formula (S)-IIc above has the (S) configuration at the chiral carbon atom and the compound of formula (R)-IIc has the (R) configuration.

Molecular depictions drawn herein follow standard conventions for depicting stereochemistry. To indicate stereo configuration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereo configuration is intended to be specified.

Hence, in an another embodiment, the extended release injectable formulations of present invention comprise an antiparasitic effective amount of at least one isoxazoline of Formula (I), Formula (II), Formula (IIa), Formula (IIb), Formula (IIc), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa) which is enriched in one enantiomer, or a pharmaceutically acceptable salt thereof.

In one embodiment, the extended release injectable formulations comprise an antiparasitic effective amount of at least one isoxazoline of Formula (I), Formula (II), Formula (IIa), Formula (IIb), Formula (IIc), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), which is enriched an enantiomer that displays significant in vitro and in vivo activity with a favorable toxicity profile (the eutomer) whereas a compound or composition enriched in the other enantiomer displays significantly less in vitro and in vivo activity (the distomer), or a pharmaceutically acceptable salt thereof. In one embodiment of the invention, the more biologically active enantiomer of the compound of Formula IIc is believed to be compound of Formula (S)-IIc shown above, which has the (S)-configuration at the chiral carbon atom. Similarly, the more biologically active enantiomers of isoxazoline compounds of formulae Formula (I), Formula (II), Formula (IIa), Formula (IIb), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa) are believed to have the (S) configuration at the chiral carbon of the isoxazoline ring.

In an embodiment, the compounds of formulae Formula (I), Formula (II), Formula (IIa), Formula (IIb), Formula (IIc), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa) present in the compositions of the invention are enriched in one enantiomer over the other enantiomer in a weight:weight ratio of at least 1.5:1. In another embodiment, the compounds of Formula (I), Formula (II), Formula (IIa), Formula (IIb), Formula (IIc), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa) present in the compositions of the invention are enriched in one enantiomer in a weight:weight ratio of at least 2:1, at least 5:1 or at least 10:1.

In another embodiment, the compounds of Formula (I), Formula (II), Formula (IIa), Formula (IIb), Formula (IIc), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa) present in the compositions of the invention are essentially pure enantiomers. Thus, in another embodiment, the invention provides extended release injectable compositions that comprise the essentially pure enantiomers of the compounds of Formula (I), Formula (II), Formula (IIa), Formula (IIb), Formula (IIc), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa).

In one embodiment, the composition of the invention comprises a compound of formula (I), that is substantially enriched in an enantiomer. The term "substantially enriched" is meant wherein the weight:weight ratio is at least about 1.5:1 or higher in favor of the desired enantiomer. In another embodiment, the extended release injectable compositions of the invention comprise a compound of formula (I), that is substantially enriched in the (S)-enantiomer. In another embodiment, the extended release injectable compositions of the invention comprise a compound of formula (I) that is substantially enriched in the (R)-enantiomer.

In another embodiment of the invention, the compositions comprise a compound of formula (I), that is enriched in the (S)-enantiomer in a weight:weight ratio of at least about 2:1, (S) to (R), or greater. In yet another embodiment, the compositions of the invention comprise a compound of formula (I) that is enriched in the (S)-enantiomer in a weight:weight ratio of at least about 5:1, (S) to (R), or greater. In still another embodiment, the compositions of the invention comprise a compound of formula (I), that is enriched in the (S)-enantiomer in a weight:weight ratio of at least about 10:1, (S) to (R), or greater. In still another embodiment, the compositions of the invention comprise a compound of formula (I), that is essentially the pure (S)-enantiomer.

In another embodiment of the invention, the compositions comprise a compound of formula (I), that is enriched in the (R)-enantiomer in a weight:weight ratio is at least approximately 2:1, (R) to (S), or greater. In yet another embodiment, the compositions of the invention comprise a compound of formula (I), that is enriched in the (R)-enantiomer in a weight:weight ratio of at least about 5:1, (R) to (S), or greater. In still another embodiment, the compositions of the invention comprise a compound of formula (I), that is enriched in the (R)-enantiomer in a weight:weight ratio of at least about 10:1, (R) to (S), or greater. In still another embodiment, the compositions of the invention comprise a compound of formula (I) that is essentially the pure R-enantiomer.

In one embodiment, the composition of the invention comprises a compound of formula (II), (IIa), (IIb), (IIc), (IId), (IIe) or (IIf) that is substantially enriched in an enantiomer. In another embodiment, the extended release injectable compositions of the invention comprise a compound of formula (II), (IIa), (IIb), (IIc), (IId), (IIe) or (IIf) that is substantially enriched in the (S)-enantiomer. In another embodiment, the extended release injectable compositions of the invention comprise a compound of formula (II), (IIa), (IIb), (IIc), (IId), (IIe) or (IIf) that is substantially enriched in the (R)-enantiomer.

In another embodiment of the invention, the compositions comprise a compound of formula (II), (IIa), (IIb), (IIc), (IId), (IIe) or (IIf) that is enriched in the (S)-enantiomer in a weight:weight ratio of at least about 2:1, (S) to (R), or greater. In yet another embodiment, the compositions of the invention comprise a compound of formula (II), (IIa), (IIb), (IIc), (IId), (IIe) or (IIf) that is enriched in the (S)-enantiomer in a weight:weight ratio of at least about 5:1, (S) to (R), or greater. In still another embodiment, the compositions of the invention comprise a compound of formula (II), (IIa), (IIb), (IIc), (IId), (IIe) or (IIf) that is enriched in the (S)-enantiomer in a weight:weight ratio of at least about 10:1, (S) to (R), or greater. In still another embodiment, the compositions of the invention comprise a compound of formula (II), (IIa), (IIb), (IIc), (IId), (IIe) or (IIf) that is essentially the pure (S)-enantiomer.

In another embodiment of the invention, the compositions comprise a compound of formula (II), (IIa), (IIb), (IIc), (IId), (IIe) or (IIf) that is enriched in the (R)-enantiomer in a weight:weight ratio is at least approximately 2:1, (R) to (S), or greater. In yet another embodiment, the compositions of the invention comprise a compound of formula (II), (IIa), (IIb), (IIc), (IId), (IIe) or (IIf) that is enriched in the (R)-enantiomer in a weight:weight ratio of at least about 5:1, (R) to (S), or greater. In still another embodiment, the compositions of the invention comprise a compound of formula (II), (IIa), (IIb), (IIc), (IId), (IIe) or (IIf) that is enriched in the (R)-enantiomer in a weight:weight ratio of at least about 10:1, (R) to (S), or greater. In still another embodiment, the compositions of the invention comprise a compound of formula (II), (IIa), (IIb), (IIc), (IId), (IIe) or (IIf) that is essentially the pure (R)-enantiomer.

In one embodiment, the composition of the invention comprises a compound of formula (IIc) that is substantially enriched in an enantiomer. In another embodiment, the extended release injectable compositions of the invention comprise a compound of formula (IIc) that is substantially enriched in the (S)-enantiomer. In another embodiment, the extended release injectable compositions of the invention comprise a compound of formula (IIc) that is substantially enriched in the (R)-enantiomer.

In another embodiment, this invention comprises racemic mixtures, for example, approximately equal amounts of the enantiomers of Formulae (I), Formula (II), Formula (IIa), Formula (IIb), Formula (IIc), Formula (IId), Formula (IIe), Formula (IIf), Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VI) or Formula (VIIa).

When enantiomerically enriched, one enantiomer is present in greater amounts than the other, and the extent of enrichment may be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers). In some embodiments, the compositions of the invention comprise compounds that have at least a 50% enantiomeric excess. In other embodiments, the compositions of the invention comprise compounds that have at least a 75% enantiomeric excess, at least a 90% enantiomeric excess, or at least a 94% enantiomeric excess of the more active isomer. Of particular note are enantiomerically pure embodiments of the more active isomer (the eutomer).

Compounds of this invention can exist as one or more conformational isomers due to restricted rotation about the amide bond bonded to the aryl or heteroaryl ring (e.g. the amide bonded to the naphthyl group in Formula (IIc)). This invention comprises mixtures of conformational isomers. In addition, this invention includes compounds that are enriched in one conformer relative to others.

It will be appreciated that in addition to the chiral carbon atom in the isoxazoline ring of the compounds of formulae (I) to (VIIa), certain compounds may include other chiral centers in one or more substituents. Thus, these compounds will have a greater number of possible stereoisomers (e.g. diastereomers). All possible stereoisomers are encompassed in the extended release injectable compositions of the invention.

Accordingly, in one embodiment of the invention, the compositions comprise a compound of Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), that is enriched in the (S)-enantiomer in a weight:weight ratio is at least approximately 2:1, (S) to (R), or greater. In yet another embodiment, the compositions of the invention comprise a compound of Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), that is enriched in the (S)-enantiomer in a weight:weight ratio of at least about 5:1, (S) to (R), or greater. In still another embodiment, the compositions of the invention comprise a compound of Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), that is enriched in the (S)-enantiomer in a weight: weight ratio of at least approximately 10:1, (S) to (R), or greater. In still another embodiment, the compositions of the invention comprise a compound of Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), that is essentially the pure (S)-enantiomer.

In another embodiment of the invention, the compositions comprise a compound of Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), that is enriched in the (R)-enantiomer in a weight:weight ratio is at least approximately 2:1, (R) to (S), or greater. In yet another embodiment, the compositions of the invention comprise a compound of Formula (III), Formula (III-1.1001) to Formula (III-1.025), Formula (III-2.001) to Formula (III-018), Formula (IV), Formula (IVa), Formula (V), Formula (Va), Formula (VI), Formula (VIa), Formula (VII) or Formula (VIIa), that is enriched in the (R)-enantiomer in a weight:weight ratio of at least about 5:1, (R) to (S), or greater. In still another embodiment, the compositions of the invention comprise a compound of Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), that is enriched in the (R)-enantiomer in a weight:weight ratio of at least approximately 10:1, (R) to (S), or greater. In still another embodiment, the compositions of the invention comprise a compound of Formula (III), Formula (III-1.1001) to Formula (III-1.025), Formula (III-2.001) to Formula (III-2.018), Formula (IV), Formula (IVa), Formula (V), Formula (Va), Formula (VI), Formula (VIa), Formula (VII) or Formula (VIIa), that is essentially the pure (R)-enantiomer.

In another embodiment, the extended release injectable formulations of present invention comprise an antiparasitic effective amount of at least one isoxazoline disclosed in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 WO 2008/122375, WO 2014/439475 $A_1$ and WO2012 120135$A_1$, all of which are incorporated herein by reference in their entirety.

In yet another embodiment, the extended release injectable formulations of present invention comprise an antiparasitic effective amount of at least one isoxazoline compound described in WO 2009/02451$A_2$ and WO 2011/075591$A_1$, both incorporated herein by reference in their entirety.

In one embodiment, the compositions of the invention may comprise about 5 to about 50% (w/w) of an isoxazoline active agent. In another embodiment, the compositions may comprise about 5 to about 30% (w/w) of the isoxazoline active agent. In yet other embodiments, the compositions may include about 5 to about 20% (w/w) or about 5 to about 15% (w/w) of the isoxazoline active agent. In another embodiment, the compositions of the invention may comprise about 10 to about 40% (w/w) or 10 to about 30% (w/w) of an isoxazoline active agent.

In another embodiment, the compositions may comprise about 10 to about 20% of an isoxazoline active agent. In yet another embodiment, the compositions of the invention may comprise about 15% to about 40% (w/w), about 15% to about 35% (w/w) or about 15% to about 30% (w/w) of an isoxazoline compound. In yet another embodiment, the compositions of the invention will comprise about 20 to about 30% (w/w), about 20 to about 25% (w/w) or about 25 to about 30% (w/w) of the isoxazoline active agent.

In one embodiment, the compositions of the invention comprise about 1 to about 40% (w/w) of a pharmaceutically acceptable polymer, including a biodegradable polymer. In other embodiments, the compositions comprise about 1 to about 30% (w/w) or about 1 to about 20% (w/w) of a pharmaceutically acceptable polymer. In another embodiment, the compositions comprise about 1 to about 15% (w/w) or about 1 to about 10% (w/w) of a pharmaceutically acceptable polymer. In another embodiment, the compositions comprise about 5 to about 20% (w/w) or about 5 to about 15% (w/w) of a pharmaceutically acceptable polymer. In another embodiment, the compositions comprise about 10 to about 20% (w/w) or about 10 to about 15% (w/w) of a pharmaceutically acceptable polymer. In another embodiment, the compositions comprise about 7 to about 13% (w/w) or about 8 to about 15% (w/w) of a pharmaceutically acceptable polymer. In yet another embodiment, the compositions of the invention comprise about 1 to about 7% (w/w), about 1 to about 5% (w/w) or about 3 to about 7% (w/w) of a pharmaceutically acceptable polymer.

In one embodiment, the compositions of the invention may comprise about 30% to about 90% (w/w) of a solvent or mixture of solvents. In another embodiment, the compositions of the invention may comprise about 40% to about 90% (w/w) of a solvent or mixture of solvents. In yet another embodiment, the compositions comprise about 40% to about 80% (w/w), about 50% to about 80% (w/w) or about 45% to about 80% (w/w) of a solvent or a mixture of solvents. In yet another embodiment, the compositions of the invention comprise about 60% to about 80% (w/w) or about 65% to about 80% (w/w) of a solvent or a mixture of solvents. In still another embodiment, the compositions may comprise about 65% to about 75% (w/w) or about 70% to about 80% (w/w) of a solvent or a mixture of solvents.

In another embodiment, the compositions of the invention may comprise about 0.01% to about 10% (w/w) of a pharmaceutically acceptable additive, excipient or mixtures thereof. In other embodiments, the compositions may comprise about 0.01% to about 5% (w/w), about 0.1% to about 10% (w/w) or about 0.1% to about 5% (w/w) of a pharmaceutically acceptable additive, excipient or mixtures thereof.

In another embodiment, the compositions of the invention may comprise about 0.01% to about 5% (w/w) of an antioxidant. In other embodiments, the compositions may comprise about 0.01% to about 3% (w/w) or about 0.01 to about 2% (w/w) of an antioxidant.

The pharmaceutically acceptable polymers in the extended release injectable formulations, include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, pseudo poly(amides), polyhydroxyalcanoates, polyhydroxybutyrates, polyhydroxyvalerates, polyalkylene oxalates, polyalkylene succinates, poly(malic acid), poly (amino acids), poly(methyl vinyl ether), poly(maleic anhydride), chitin, chitosan, and copolymers, terpolymers, or combinations or mixtures therein including copolymers of polylactides, polycaprolactones, polyglycolides (e.g., poly (lactide-co-glycolide) and copolymers of polyethylene glycol or methoxy polyethylene glycol with one Or more of polycaprolactone, polylactide or any of the other polymers/polymer groups mentioned above. Also included are derivatives of pharmaceutically acceptable polymers such as hydroxylated derivatives including polycaprolactone diols and the like.

In one embodiment, the pharmaceutically acceptable polymer is a biodegradable polymer. In another embodiment, the pharmaceutically acceptable biodegradable polymer can have one or more or all of the following characteristics: be bioerodible by cellular action, biodegradable by action of non-living body fluid components, soften when exposed to heat but return to the original state when cooled and are capable of substantially dissolving or dispersing in a water-miscible carrier or solvent to form a solution or dispersion. Upon contact with an aqueous fluid the polymer is capable of assisting in the formation of the film coated or encapsulated liquid or solid (which will contain the active agent in the present invention). The kinds of polymers suitable for the present composition generally include any having the foregoing characteristics. Examples of biodegradable polymers include, but are not limited to, polylactides, polycaprolactones, polyglycolides, polyorthoesters, polyurethanes, polyphasphazenes, pseudo poly(amides), and copolymers thereof.

It will be apparent to the skilled person that the molecular weight of a polymer is not a discreet number but can be presented in a molecular weight range. The average molecular weight of a polymer may be found by techniques familiar to persons of skill in the art, for example, size exclusion chromatography with molecular weight standards, or the like. The molecular weight range of a polymer can impact the physical characteristics of the material and the way that it interacts with the active agent. Accordingly the molecular weight range of the polymer may impact the characteristics of the extended release compositions of the invention. For example, in some embodiments depending on the active agent and solvents included, one may see an earlier release of the isoxazoline active agent when the weight average molecular weight range is from about 5 to about 20 kDa (kilo daltons) or from about 7 to about 15 kDa. A later release of the isoxazoline active agent may be observed when the weight average molecular weight is between about 30 to about 70 kDa (e.g., about 40 to about 70 kDa or about 45 to about 60 kDa) or from about 90 to about 200 kDa (e.g., about 100 to about 150 or about 105 to about 130 kDa). In some embodiments, a combination of polymers having different average molecular weights may provide a release rate that combines the effect of the different polymers used.

Inherent viscosity (IV) in polymer chemistry is a viscometric method for measuring molecular weight. It is defined as the ratio of the natural logarithm of the relative viscosity to the mass concentration of the polymer and is based on the flow time of a polymer solution through a narrow capillary. As used herein with respect to the molecular weight range of a pharmaceutically acceptable polymer, the term "low molecular weight" (LMW) refers to polymer with an inherent viscosity in the range of 0.05-0.29 dL/g; the term "medium molecular weight" refers to a polymer with an inherent viscosity in the range of 0.3-0.55 dL/g; and high molecular weight refers to a polymer with an inherent viscosity in the range of 0.55-1.0 dL/g. In another embodiment, the pharmaceutically acceptable polymer in the extended release formulations of the invention will have an inherent viscosity of about 0.10-0.20 dL/g. In another embodiment, the pharmaceutically acceptable polymer in the extended release formulations will have an inherent viscosity of about 0.35-0.50.

In some embodiments, the extended release injectable formulations of the invention comprise polylactides, polycaprolactones, polyglycolides and copolymers thereof. In another embodiment, the compositions include a poly(lactide-co-glycolide) copolymer ("PLGA"). PLGA copolymers may have different molecular weight ranges and may also have different weight:weight ratios of lactide to glycolide. This ratio, may affect the properties of the copolymer and the way that it interacts with the active agent. Since a lactide group contains an additional methyl group in the sidechain compared with a glycolide, this change may affect the conformation of the polymer and change the way in which the polymer interacts with the isoxazoline active agent (and/or other active agent combined with the isoxazoline). Although not bound by theory, in one embodiment, the compositions of the invention having a higher lactide to glycolide ratio (e.g. 75:25 compared with 50:50) result in an increase in hydrogen bonding between the active agent and the polymer, leading to better solubility of the active agent in vivo.

This effect improves the injection site reaction and allows for the extendable release injectable compositions to include a higher amount of the active agent, which will translate to a longer duration of efficacy.

In one embodiment of the invention, when the pharmaceutically acceptable polymer is PLGA, the ratio of lactide to glycolide is about 30:70 to about 99:1. In another embodiment of the invention where the pharmaceutically acceptable polymer is PLGA, the ratio of lactide to glycolide is about 40:60 to about 80:15. In another embodiment of the invention where the pharmaceutically acceptable polymer is PLGA, the ratio of lactide to glycolide is about 40:60 to about 60:40. In another embodiment of the invention where the pharmaceutically acceptable polymer is PLGA, the ratio of lactide to glycolide is about 70:30 to about 80:20. In another embodiment of the invention, where the pharmaceutically acceptable polymer is PLGA, the ratio of lactide to glycolide is about 50:50. In another embodiment of the invention, where the pharmaceutically acceptable polymer is PLGA, the ratio of lactide to glycolide is about 75:25.

In some embodiments, the amount of PLGA contained in the extended release injectable formulation of the invention is about 1% to about 30% (w/w), In another embodiment, the compositions comprise about 1 to about 20% (w/w) of PLGA. In another embodiment, the compositions comprise about 5 to about 20%, about 8% to about 20% (w/w) or about 10 to about 20% (w/w). In another embodiment, the compositions comprise about 5 to about 15% (w/w) of PLGA. In other embodiments, the amount of PLGA contained in the extended release injectable formulation of the invention is from about 3% to about 15% (w/w) or is from about 10% to about 15% (w/w). In yet another embodiment, the compositions comprise about 7 to about 13% or about 8 to about 15% (w/w) of PLGA.

In some embodiments, the weight:weight ratio of—PLGA to the isoxazoline active agent is greater than or equal to about 1:1, for example, from about 1.1:1 to about 20:1; e.g., about 1:1 to about 10:1, about 1.1:1 to about 10:1 or about 2:1 to about 5:1. In other embodiments, the weight:weight ratio of PLGA to the isoxazoline active agent is about 1.2:1 to about 5:1. In another embodiment, the weight:weight ratio of PLGA to the isoxazoline active agent is about 1.2:1 to about 2:1. In yet another embodiment, the weight:weight ratio of PLGA to the isoxazoline active agent is about 1.2:1 to about 1.3:1.

In other embodiments the weight:weight ratio of PLGA to the isoxazoline active agent is about 1.5:1 to about 1:1.5. In other embodiments, the ratio of the isoxazoline active agent to PLGA is from about 1.25:1 to about 1:1:25.

The solvents used in the extended release injectable formulations of the invention may be a single or a blend of solvents. Non-limiting examples of these solvents include alcohols such as ethanol, 1-propanol, isopropanol, glycol ethers (e.g., including, but limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), liquid polyethylene glycols (PEGs) including, but not limited to, PEG 200, PEG 300 and PEG 400; propylene glycol, glycerol, glycerol esters including glycerol triacetate (triacetin), cyclic carbonates (e.g., ethylene carbonate and propylene carbonate), 2-pyrrolidone, N-methylpyrrolidone, dimethyl isosorbide (DMI), dimethylacetamide (DMA), dimethyl formamide (DMF), caprolactam, glycerol formal, acetone, dimethylsulfoxide (DMSO), ethyl acetate, ethyl lactate, benzyl benzoate, or a mixture of at least two of these solvents.

In one embodiment, the compositions of the invention may include one or more poloxamers as a solvent or surfactant. Poloxamers are a family of synthetic block copolymers of ethylene oxide and propylene oxide. Poloxamers may be liquid, a milky white paste or a powder and are represented by the following structure:

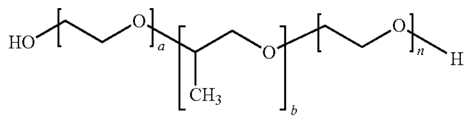

where a is an integer between 2 and 130 and b is an integer between 15 and 67 (see, U.S. Pat. No. 3,740,421). Poloxamer are available from commercial sources such as BASF and Croda. An example of a poloxamer is P-124 which is a solid at room temperature. In one embodiment, poloxamer P-124 has the values a=12 and b=20. Other poloxamers include P-128 (a=38 and b=29), P-181 (a=3 and b=30) P-188 (a=80 and b=27), P-237 (a=64 and b=37), P338 (a=141 and b=44) and P407 (a=101 and b=56). In some embodiments, the amount of poloxamer, when present, is from about 0.5% to about 20 (w/w). In other embodiments, the compositions may have, when present, about 1% to about 20% (w/w), about 1% to about 10% (w/w) or from about 1 to about 5% (w/w). In other embodiments, the amount of poloxamer, when present, is from about 1% to about 3% (w/w).

In one embodiment, the compositions of the invention comprise a solvent or mixture of solvents that is miscible with water. Solvents that are miscible with water are well known and include certain alcohols, liquid polyethylene glycols (PEGs), certain poloxamers, glycols and glycol ethers and polar aprotic solvents. Alcohols that are miscible with water include, but are not limited to ethanol, isopropanol, n-propanol, Solketal (isopropylidene glycerol) or glycerol formal. Polar aprotic solvents include, but are not limited to, amides such as dimethylacetamide, dimethylformamide, 2-pyrrolidone, N-alkylpyrrolidones such as N-methylpyrrolidone and N-octylpyrrolidone, dimethylisosorbide, dimethylsulfoxide, cyclic carbonates including propylene carbonate and ethylene carbonate, and certain ketones such as acetone and the like. Glycol ethers include, but are not limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like.

In one embodiment, the extended release formulations of the invention comprise a polar protic solvent including, but not limited to, an alcohol such as ethanol, isopropanol or a glycol or glycol ether.

In another embodiment, the extended release injectable formulations of the invention comprise a polar aprotic solvent such as N-methylpyrrolidone, dimethyl isosorbide, dimethylacetamide or propylene carbonate.

In yet another embodiment of the invention, the compositions of the invention include non-water miscible solvents (e.g. not completely miscible with water, although they may have some solubility in water). Non-limiting examples of these solvents include 1-butanol, 2-butanol, 1-pentanol, 3-pentanol, benzyl alcohol, methylethylketone (MEK), triacetin, lipids, triglycerides including medium chain triglycerides such $C_8$-$C_{10}$ triglycerides such as capric/caprilic triglycerides, propylene glycol derivatives (e.g. propylene glycol monolaurate), caprylocaproyl polyoxyl-8 glycerides (Labrasol) (non-ionic water dispersible surfactant, isopropyl myristate, oils such as castor oil, soybean oil or other vegetable oils or derivatives thereof such as epoxidized or hydrogenated vegetable oils such as epoxidized soybean oil or hydrogenated castor oil, or a mixture of at least two of these solvents.

In another embodiment, the composition of the invention may include neutral oils as a solvent. Neutral oils are triglycerides of fractionated plant fatty acids with chain lengths of $C_8$ to $C_{10}$. Two commercially available products are known as MIGLYOL® 810 and MIGLYOL®812.

In another embodiment, the neutral oil is a triglyceride of fractionated plant fatty acids with chain lengths of $C_8$ and $C_{10}$ combined with linoleic acid (about 4-5%). A commercially available product is known as MIGLYOL® 818. In yet another embodiment, the neutral oil is a glycerin ester of fractionated plant fatty acids with chain lengths of $C_8$ and $C_{10}$ combined with succinic acid. A commercially available product is known as MIGLYOL® 829. In yet another embodiment, the neutral oil is a propylene glycol fatty acid ester. In one embodiment, the neutral oil may be a propylene glycol diester of saturated plant fatty acids with chain lengths of $C_8$ and $C_{10}$. A commercially available product is known as MIGLYOL® 840 (propylene glycol dicaprylate/dicaprate). In yet another embodiment, the solvent may be a mixture of two or more neutral oils.

It will be appreciated that blends of solvents may be used as the solvent of the extended release injectable formulations. In one embodiment, the compositions of the invention may contain a blend of a water-miscible solvent with a solvent that is not water miscible. For example, in one embodiment, the solvent may be a mixture of a cyclic carbonate such as propylene carbonate with triacetin. Of course, other blends of a water-miscible solvent and a non-water miscible solvent are possible. In one embodiment, the water-miscible solvent in the solvent blend may be a water-miscible alcohol such as ethanol or isopropanol, glycerol formal or Solketal, an amide such as 2-pyrrolidone, N-methylpyrrolidone, dimethylisosorbide or dimethylacetamide, a glycol such as propylene glycol, glycerol or a glycol ether.

In another embodiment, the non-water miscible solvent in the solvent blend may be triacetin, benzyl alcohol, a triglyceride including $C_5$-$C_{10}$ triglycerides such as capric/caprilic triglycerides, propylene glycol derivatives (e.g. propylene glycol monolaurate), caprylocaproyl polyoxyl-8 glycerides (Labrasol); a propylene glycol fatty acid diester, and the like.

In one embodiment, the solvent may be a blend of a water-miscible solvent and a non-water miscible solvent in a weight:weight ratio of between about 10 to 1 to about 1 to 10, water-miscible solvent to non-water miscible solvent. In another embodiment, the weight:weight ratio of the water-miscible solvent to non-water miscible solvent may be from about 5 to 1 to about 1 to 1. In another embodiment, the weight:weight ratio of the water-miscible solvent to non-water miscible solvent may be from about 3 to 1 to about 1 to 1. In another embodiment, the weight:weight ratio of the water-miscible solvent to non-water miscible solvent may be from about 3 to 1 to about 2 to 1 or about 2 to 1 to about 1 to 1.

In yet another embodiment, the solvent may be a blend of a water-miscible solvent and a non-water miscible solvent in a weight:weight ratio of about 1 to 2 or about 1 to 3, water-miscible solvent to non-water miscible solvent. In another embodiment, the weight:weight ratio of the water-miscible solvent to non-water miscible solvent may be from about 1 to about 5, 1 to about 7.

In one embodiment, the solvent may be a blend of cyclic carbonate (e.g., propylene carbonate) and glycerol ester (e.g., triacetin) in a weight:weight ratio of between about 10 to 1 to about 1 to 1, cyclic carbonate (e.g., propylene carbonate) to glycerol ester (e.g., triacetin). In one embodiment, the solvent may be a blend of cyclic carbonate (e.g., propylene carbonate) and glycerol ester (e.g., triacetin) in a weight:weight ratio of between about 5 to 1 to about 1 to 1, cyclic carbonate (e.g. propylene carbonate) to glycerol ester (e.g., triacetin). In another embodiment, the solvent may be a blend of cyclic carbonate (e.g., propylene carbonate) and glycerol ester (e.g., triacetin) in a weight:weight ratio of between about 3 to 1 to about 1 to 1, cyclic carbonate (e.g. propylene carbonate) to glycerol ester (e.g., triacetin). In yet another embodiment, the solvent may be a blend of cyclic carbonate (e.g., propylene carbonate) and glycerol ester (e.g., triacetin) in a weight:weight ratio of between about 2 to 1 to about 1 to 1 or about 3:1 to about 2:1, cyclic carbonate (e.g. propylene carbonate) to glycerol ester (e.g., triacetin). In other embodiments, the range for the weight:weight ratio of cyclic carbonate (e.g. propylene carbonate) to glycerol ester (e.g., triacetin) is 1.5:1 to about 15:1 or from about 2:1 to about 6:1.

Surfactants may be present in the inventive formulations at concentrations of about 0.1% to about 10% (w/w), about 1% to about 10% (w/w) or about 5% to about 10% (w/w). More typically, surfactants may be present at concentrations of about 0.1% to about 5% (w/w) or about 1 to about 5% (w/w). Examples of surfactants that may be used in the compositions include, but are not limited to, glyceryl monooleate, polyoxyethylene sorbitan fatty acid esters, sorbitan esters30 including sorbitan monooleate (Span® 20), polyvinyl alcohol, polysorbates including polysorbate 20 and polysorbate 80, d-a-tocopheryl polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like).

Polyethylene glycol stearates (synonyms include macrogol stearates, polyoxylstearates, polyoxyethylene stearates, ethoxylated stearates; CAS No. 9004-99-3, 9005-08-7) are mixtures of mono- and distearate esters of mixed polyoxyethylene polymers. Polyethylene glycol hydroxystearate is a mixture of mono- and diesters of hydroxystearic acid with polyethylene glycols. One polyethylene glycol hydroxystearate that may be used in the compositions is polyethylene glycol 12-hydroxystearate. In another embodiment, the inventive formulations may include the surfactant polyethylene glycol 15 12-hydroxystearate (Kolliphor® HS 15 from BASF), a mixture of mono- and diesters of 12-hydroxystearic acid with 15 moles of ethylene oxide. Again, these compounds, as well as their amounts are well known in the art. In another embodiment of the invention, the inventive formulations may include polyoxyl 35 castor oil (Kolliphor® EL) as a surfactant. In other embodiments, the inventive formulations may include polyoxyl 40 hydrogenated castor oil (Kolliphor® RH 40) or polyoxyl 60 hydrogenated castor oil as surfactants. The formulations of the invention may also include a combination of surfactants.

The inventive formulations may contain other inert ingredients such as antioxidants, preservatives, or pH stabilizers. These compounds are well known in the formulation art. Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol, tert-butyl hydroquinone (TBHQ), and the like, may be added to the present formulation. The antioxidants are generally added to the formulation in amounts of from about 0.01 to about 5.0%, based upon total weight of the formulation, with about 0.05 to about 2.0% being especially preferred. In another embodiment, the formulation preferably contains about 0.05 to about 1.0% (w/w) of an antioxidant.

Preservatives, such as the parabens (methylparaben, ethylparaben, butylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, cetrimide, chlorhexidine, chlorobutanol, chlorocresol, cresol, imidurea, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate.

In certain embodiments the present invention provides for extended release injectable formulations for the treatment and/or prevention of parasitic infections and infestations of animals comprising:

a) about 5 to 30% (w/w) of an isoxazoline active agent, such as, for example, any of the isoxazoline compounds provided for in the embodiments above (e.g., a compound of any of Formulae I-VIIa);
b) about 1% to about 40 (w/w) pharmaceutically acceptable polymer;
c) about 40% to 95% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In certain embodiments the present invention provides for extended release injectable formulations for the treatment and/or prevention of parasitic infections and infestations of animals comprising:

a) about 5 to 30% (w/w) of an isoxazoline active agent, such as, for example, any of the isoxazoline compounds provided for in the embodiments above (e.g., a compound of any of Formulae I-VIIa);
b) about 1% to about 30 (w/w) pharmaceutically acceptable polymer;
c) about 40% to 95% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In another embodiment, the present invention provides for extended release injectable formulations for the treatment and/or prevention of parasitic infections and infestations of animals comprising:

a) about 15 to 30% (w/w) of an isoxazoline active agent, such as, for example, any of the isoxazoline compounds provided for in the embodiments above (e.g., a compound of any of Formulae I-VIIa);
b) about 10% to about 40 (w/w) pharmaceutically acceptable polymer;
c) about 30% to 85% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally, about 0.01% to about 5.0% (w/w) of a pharmaceutically acceptable additive, excipient or mixtures thereof.

In another embodiment, the present invention provides for extended release injectable formulations for the treatment and/or prevention of parasitic infections and infestations of animals comprising:

a) about 15 to 30% (w/w) of an isoxazoline active agent, such as, for example, any of the isoxazoline compounds provided for in the embodiments above (e.g., a compound of any of Formulae I-VIIa);
b) about 1% to about 30 (w/w) pharmaceutically acceptable polymer;
c) about 30% to 85% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally, about 0.01% to about 5.0% (w/w) of a pharmaceutically acceptable additive, excipient or mixtures thereof.

In certain other embodiments the present invention provides for extended release injectable formulations for the treatment and/or prevention of parasitic infections and infestations of animals comprising:

a) about 15 to 30% (w/w) of an isoxazoline active agent, such as, for example, any of the isoxazoline compounds provided for in the embodiments above (e.g., a compound of any of Formulae I-VIIa);
b) about 12% to about 38% (w/w) of a pharmaceutically acceptable biodegradable polymer;
c) about 40% to about 85% (w/w) of a pharmaceutically acceptable solvent or mixture of solvents;
d) optionally, about 0.01% to about 2.0% (w/w) of an antioxidant
e) optionally, about 0.1% to about 10% (w/w) of a surfactant; and
f) optionally about 0.01% to about 5.0% (w/w) of a pharmaceutically acceptable additive, excipient or mixtures thereof.

In certain other embodiments the present invention provides for extended release injectable formulations for the treatment and/or prevention of parasitic infections and infestations of animals comprising:

a) about 15 to 30% (w/w) of an isoxazoline active agent, such as, for example, any of the isoxazoline compounds provided for in the embodiments above (e.g., a compound of any of Formulae I-VIIa);
b) about 1% to about 20% (w/w) of a pharmaceutically acceptable biodegradable polymer;
c) about 40% to about 85% (w/w) of a pharmaceutically acceptable solvent or mixture of solvents;
d) optionally, about 0.01% to about 2.0% (w/w) of an antioxidant
e) optionally, about 0.1% to about 10% (w/w) of a surfactant; and
f) optionally about 0.01% to about 5.0% (w/w) of a pharmaceutically acceptable additive, excipient or mixtures thereof.

In another embodiment the present invention provides for extended release injectable formulations for the treatment and/or prevention of parasitic infections and infestations of animals comprising:

a) about 20 to 30% (w/w) of an isoxazoline active agent, such as, for example, any of the isoxazoline compounds provided for in the embodiments above (e.g., a compound of any of Formulae I-VIIa);
b) about 15% to about 40% (w/w) of a pharmaceutically acceptable biodegradable polymer;
c) about 50% to about 80% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In another embodiment the present invention provides for extended release injectable formulations for the treatment and/or prevention of parasitic infections and infestations of animals comprising:

a) about 20 to 30% (w/w) of an isoxazoline active agent, such as, for example, any of the isoxazoline compounds provided for in the embodiments above (e.g., a compound of any of Formulae I-VIIa);
b) about 1% to about 10% (w/w) of a pharmaceutically acceptable biodegradable polymer;
c) about 50% to about 80% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In another embodiment the present invention provides for extended release injectable formulations for the treatment and/or prevention of parasitic infections and infestations of animals comprising:

a) about 20 to 30% (w/w) of an isoxazoline active agent, such as, for example, any of the isoxazoline compounds provided for in the embodiments above (e.g., a compound of any of Formulae I-VIIa);
b) about 15% to about 38% (w/w) of a pharmaceutically acceptable biodegradable polymer;
c) about 60% to about 80% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally, about 0.01% to about 5.0% (w/w) of a pharmaceutically acceptable additive, excipient or mixtures thereof.

In another embodiment the present invention provides for extended release injectable formulations for the treatment and/or prevention of parasitic infections and infestations of animals comprising:

a) about 20 to 30% (w/w) of an isoxazoline active agent, such as, for example, any of the isoxazoline compounds provided for in the embodiments above (e.g., a compound of any of Formulae I-VIIa);
b) about 3% to about 7% (w/w) of a pharmaceutically acceptable biodegradable polymer;
c) about 60% to about 80% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally, about 0.01% to about 5.0% (w/w) of a pharmaceutically acceptable additive, excipient or mixtures thereof.

In other embodiments where the compositions comprise an isoxazoline active agent which is enriched in the more active enantiomer (the eutomer) the present invention provides for extended release injectable formulations for the treatment and/or prevention of parasitic infections and infestations of animals comprising:

a) about 5 to 20% (w/w) of an isoxazoline active agent, such as, for example, any of the isoxazoline compounds provided for in the embodiments above (e.g., a compound of any of Formulae I-VIIa) enriched in the (S)-enantiomer;
b) about 1% to about 30% (w/w) pharmaceutically acceptable polymer;
c) about 40% to 95% (w/w) of a pharmaceutically acceptable solvent or mixture of solvents;
d) optionally, about 0.01% to about 2.0% (w/w) of an antioxidant;
e) optionally, 0.1% to about 10% (w/w) of a surfactant; and
f) optionally, about 0.01% to about 5.0% (w/w) of a pharmaceutically acceptable additive, excipient or mixtures thereof.

In other embodiments where the compositions comprise an isoxazoline active agent which is enriched in the more active enantiomer (the eutomer) the present invention provides for extended release injectable formulations for the treatment and/or prevention of parasitic infections and infestations of animals comprising:

a) about 5 to 20% (w/w) of an isoxazoline active agent, such as, for example, any of the isoxazoline compounds provided for in the embodiments above (e.g., a compound of any of Formulae I-VIIa) enriched in the (S)-enantiomer;
b) about 1% to about 28% (w/w) pharmaceutically acceptable polymer;
c) about 40% to 95% (w/w) of a pharmaceutically acceptable solvent or mixture of solvents;
d) optionally, about 0.01% to about 2.0% (w/w) of an antioxidant;
e) optionally, 0.1% to about 10% (w/w) of a surfactant; and
f) optionally, about 0.01% to about 5.0% (w/w) of a pharmaceutically acceptable additive, excipient or mixtures thereof.

In certain other embodiments where the compositions comprise an isoxazoline active agent which is enriched in the more active enantiomer (the eutomer), the present invention provides for extended release injectable formulations for the treatment and/or prevention of parasitic infections and infestations of animals comprising:

a) about 5 to 15% (w/w) of an isoxazoline active agent, such as, for example, any of the isoxazoline compounds provided for in the embodiments above (e.g., a compound of any of Formulae I-VIIa) enriched in the (S)-enantiomer;
b) about 1% to about 20% (w/w) of a pharmaceutically acceptable biodegradable polymer;
c) about 50% to about 95% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally, about 0.01% to about 5.0% (w/w) of a pharmaceutically acceptable additive, excipient or mixtures thereof.

In certain other embodiments where the compositions comprise an isoxazoline active agent which is enriched in the more active enantiomer (the eutomer), the present invention provides for extended release injectable formulations for the treatment and/or prevention of parasitic infections and infestations of animals comprising:

a) about 5 to 15% (w/w) of an isoxazoline active agent, such as, for example, any of the isoxazoline compounds provided for in the embodiments above (e.g., a compound of any of Formulae I-VIIa) enriched in the (S)-enantiomer;
b) about 5% to about 20% (w/w) of a pharmaceutically acceptable biodegradable polymer;
c) about 60% to about 95% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In certain other embodiments where the compositions comprise an isoxazoline active agent which is enriched in the more active enantiomer (the eutomer), the present invention provides for extended release injectable formulations for the treatment and/or prevention of parasitic infections and infestations of animals comprising:

a) about 5 to 15% (w/w) of an isoxazoline active agent, such as, for example, any of the isoxazoline compounds provided for in the embodiments above (e.g., a compound of any of Formulae I-VIIa) enriched in the (S)-enantiomer;
b) about 1% to about 10% (w/w) of a pharmaceutically acceptable biodegradable polymer;
c) about 60% to about 95% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In certain other embodiments where the compositions comprise an isoxazoline active agent which is enriched in the more active enantiomer (the eutomer), the present invention provides for extended release injectable formulations for the treatment and/or prevention of parasitic infections and infestations of animals comprising:

a) about 5 to 15% (w/w) of an isoxazoline active agent, such as, for example, any of the isoxazoline compounds provided for in the embodiments above (e.g., a compound of any of Formulae I-VIIa) enriched in the (S)-enantiomer;
b) about 3% to about 20% (w/w) of a pharmaceutically acceptable biodegradable polymer;
c) about 70% to about 95% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In certain other embodiments where the compositions comprise an isoxazoline active agent which is enriched in the more active enantiomer (the eutomer), the present invention provides for extended release injectable formulations for the treatment and/or prevention of parasitic infections and infestations of animals comprising:

a) about 5 to 15% (w/w) of an isoxazoline active agent, such as, for example, any of the isoxazoline compounds provided for in the embodiments above (e.g., a compound of any of Formulae I-VIIa) enriched in the (S)-enantiomer;
b) about 1% to about 5% (w/w) of a pharmaceutically acceptable biodegradable polymer;
c) about 70% to about 95% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally about 0.01% to about 5.0% (w/w) of a pharmaceutically acceptable additive, excipient or mixtures thereof.

In another embodiment the present invention where the compositions comprise an isoxazoline active agent enriched in the more active enantiomer (the eutomer), the invention provides for extended release injectable formulations for the treatment and/or prevention of parasitic infections and infestations of animals comprising:

a) about 10 to 20% (w/w) of an isoxazoline active agent, such as, for example, any of the isoxazoline compounds provided for in the embodiments above (e.g., a compound of any of Formulae I-VIIa) enriched in the (S)-enantiomer;
b) about 8% to about 30% (w/w) of a pharmaceutically acceptable biodegradable polymer;
c) about 60% to about 90% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally, about 0.01% to about 5.0% (w/w) of a pharmaceutically acceptable additive, excipient or mixtures thereof.

In another embodiment the present invention where the compositions comprise an isoxazoline active agent enriched in the more active enantiomer (the eutomer), the invention provides for extended release injectable formulations for the treatment and/or prevention of parasitic infections and infestations of animals comprising:

a) about 10 to 20% (w/w) of an isoxazoline active agent, such as, for example, any of the isoxazoline compounds provided for in the embodiments above (e.g., a compound of any of Formulae I-VIIa) enriched in the (S)-enantiomer;
b) about 3% to about 7% (w/w) of a pharmaceutically acceptable biodegradable polymer;
c) about 60% to about 90% (w/w) of a pharmaceutically acceptable solvent or mixture of solvents;
d) optionally, about 0.01% to about 2.0% (w/w) of an antioxidant;
e) optionally, about 0.1% to about 10% (w/w) of a surfactant; and
f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 5 to 30% (w/w) of an isoxazoline active agent, such as, for example, any of the isoxazoline compounds provided for in the embodiments above (e.g., a compound of any of Formulae I-VIIa), such as, a compound of the formula:

(IIc)

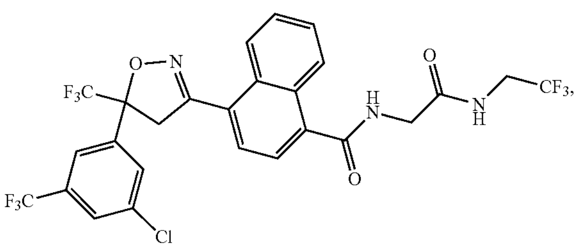

(IId)

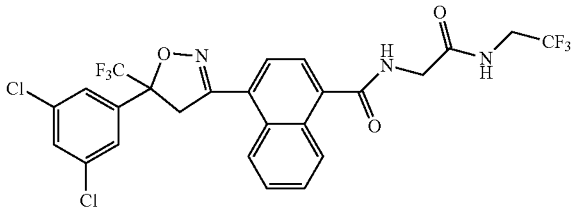

(IIe)

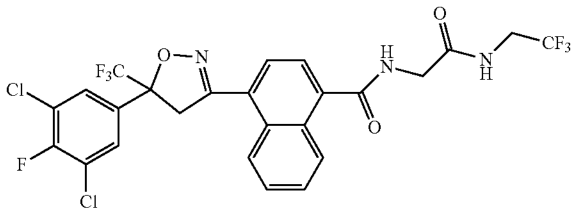

-continued (IIf)

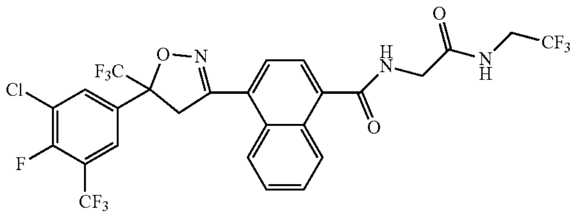

(IVa)

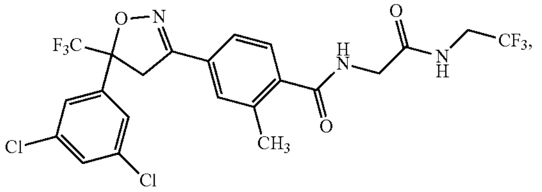

(Va)

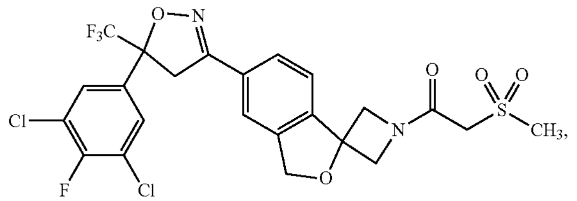

(VIa)

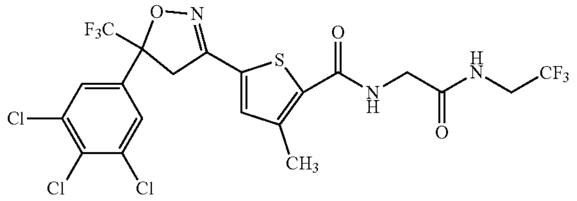

or (VIIa)

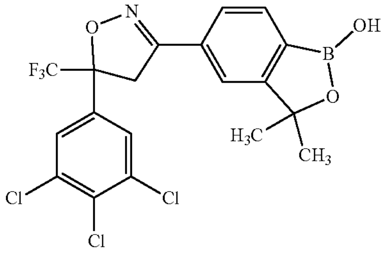

b) about 1% to about 40% (w/w) of a pharmaceutically acceptable polymer;

c) about 40% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 5 to 30% (w/w) of an isoxazoline active agent, such as, for example, any of the isoxazoline compounds provided for in the embodiments above (e.g., a compound of any of Formulae I-VIIa), such as, a compound of the formula:

(IIc)

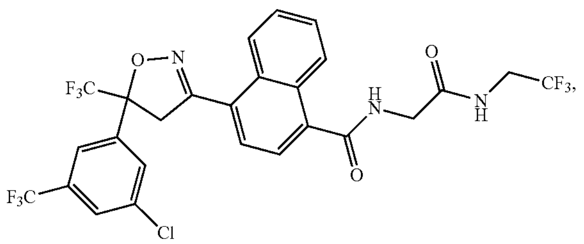

(IId)

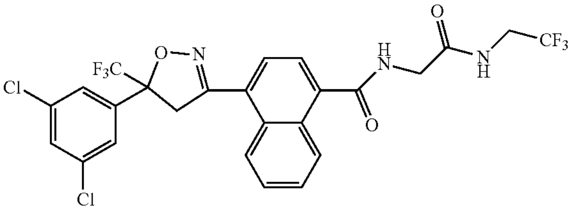

(IIe)

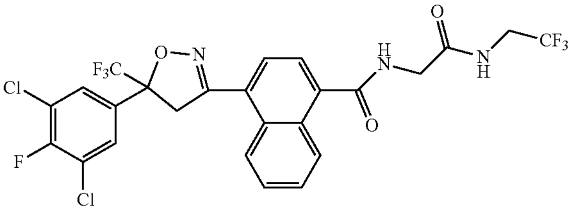

(IIf)

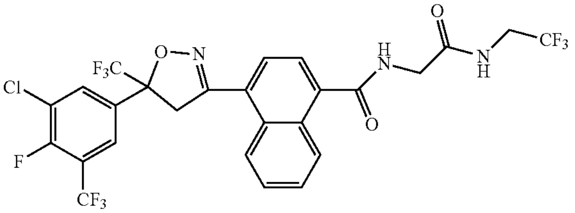

(IVa)

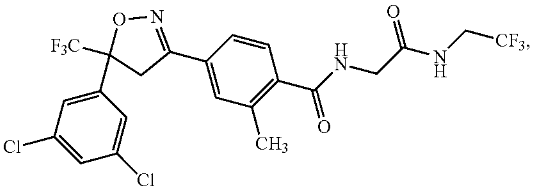

(Va)

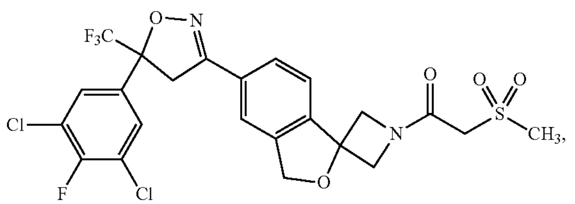

-continued (VIa)

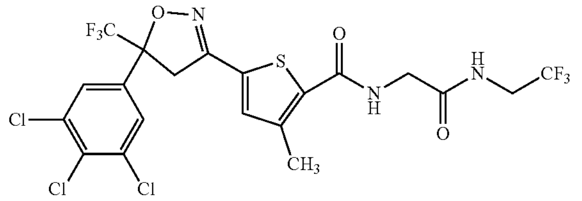

or (VIIa)

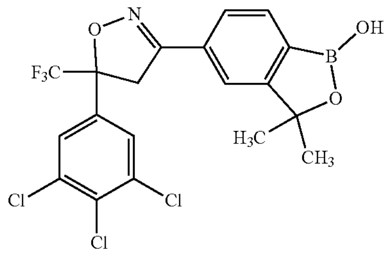

or a pharmaceutically acceptable salt thereof, b) about 1% to about 30% (w/w) of a pharmaceutically acceptable polymer;

c) about 40% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

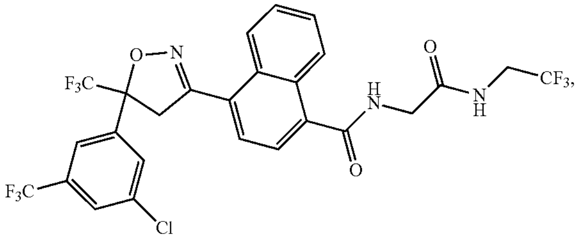

(IId)

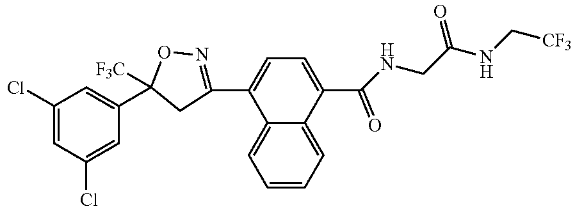

-continued (IIe)

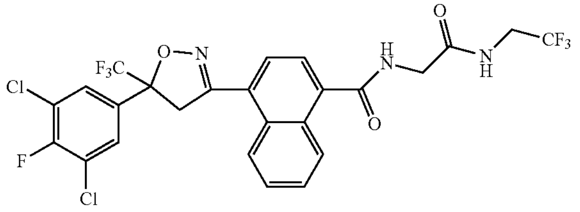

(IIf)

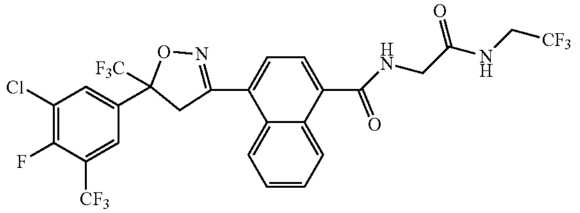

(IVa)

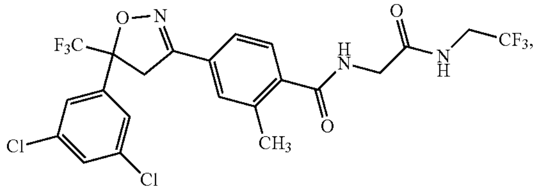

(Va)

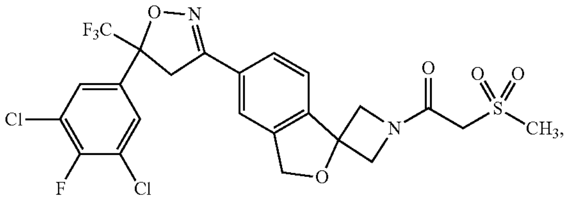

(VIa)

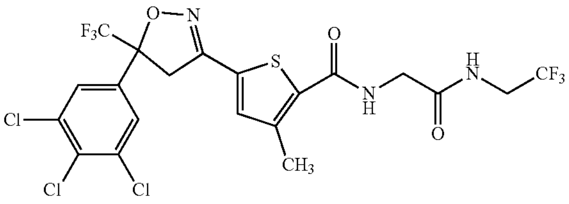

or (VIIa)

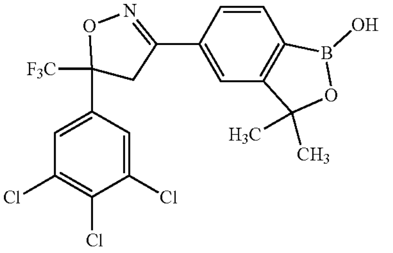

or a pharmaceutically acceptable salt thereof, b) about 10% to about 40% (w/w) of a pharmaceutically acceptable polymer;

c) about 30% to about 85% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

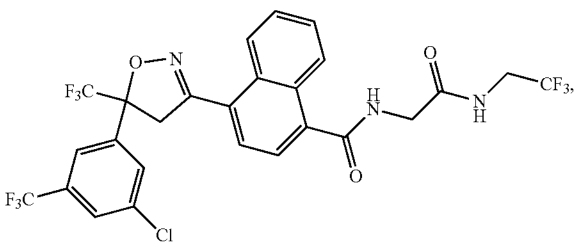

(IId)

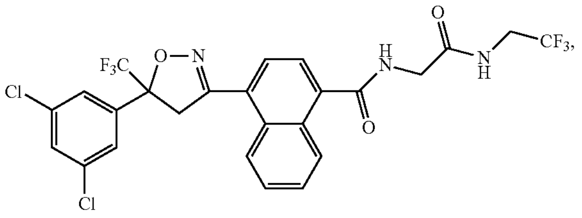

(IIe)

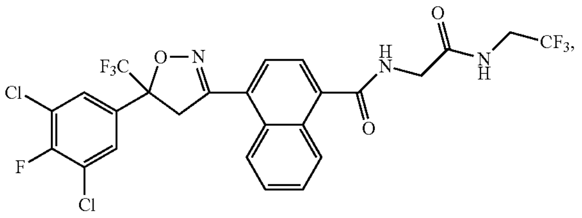

(IIf)

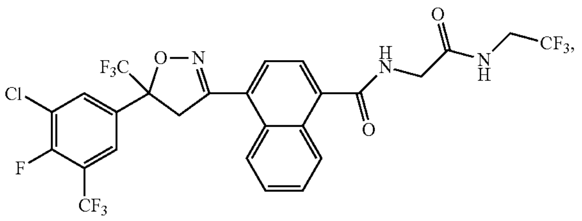

(IVa)

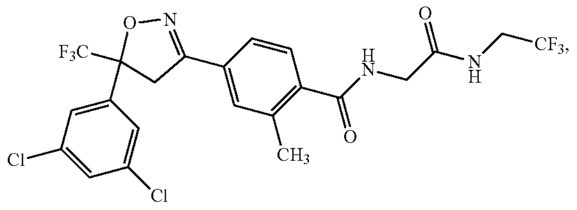

-continued (Va)

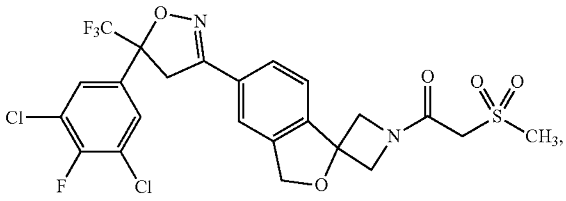

(VIa)

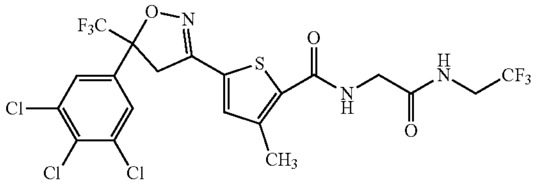

or (VIIa)

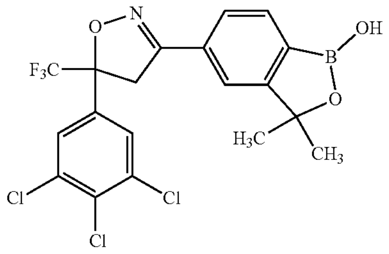

or a pharmaceutically acceptable salt thereof, b) about 1% to about 30% (w/w) of a pharmaceutically acceptable polymer;

c) about 30% to about 85% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 20 to 30% (w/w) of an isoxazoline active agent, such as, for example, any of the isoxazoline compounds provided for in the embodiments above (e.g., a compound of Formulae I-VIIa), such as, a compound of the formula:

(IIc)

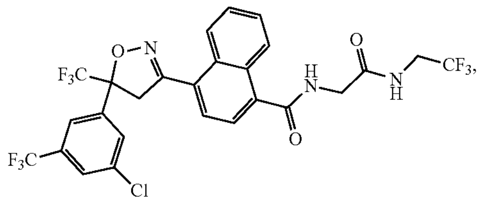

-continued (IId)

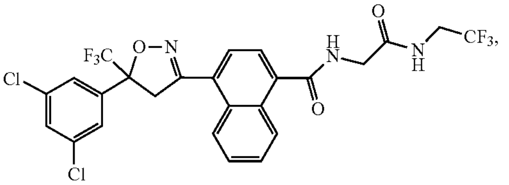

(IIe)

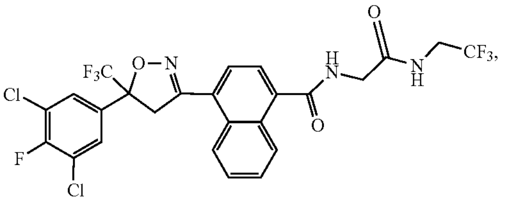

(IIf)

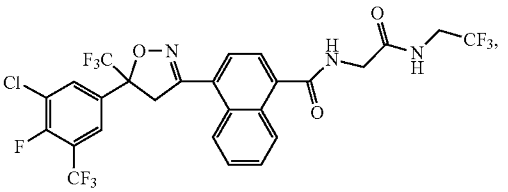

(IVa)

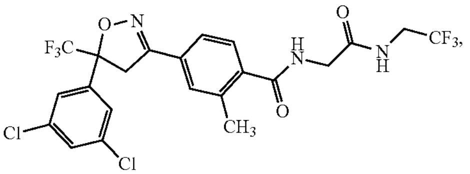

(Va)

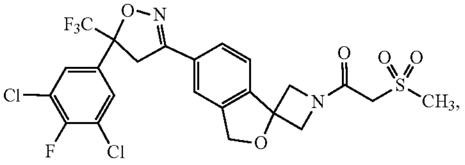

(VIa)

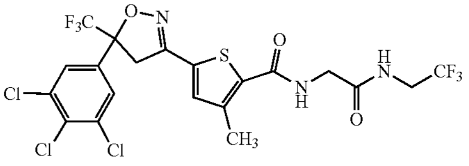

or (VIIa)

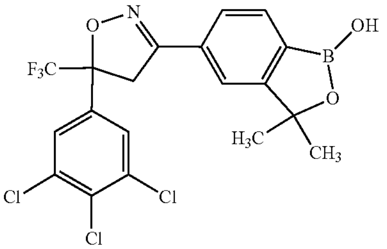

or a pharmaceutically acceptable salt thereof, b) about 15% to about 40% (w/w) of a pharmaceutically acceptable polymer;

c) about 50% to about 80% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 20 to 30% (w/w) of an isoxazoline active agent, such as, for example, any of the isoxazoline compounds provided for in the embodiments above (e.g., a compound of Formulae I-VIIa), such as, a compound of the formula:

(IIc)

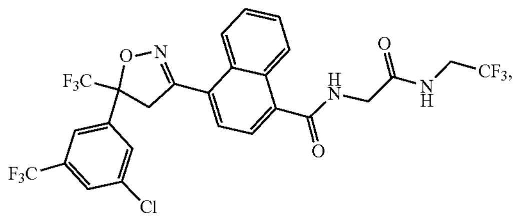

(IId)

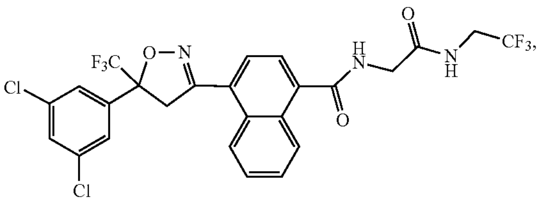

(IIe)

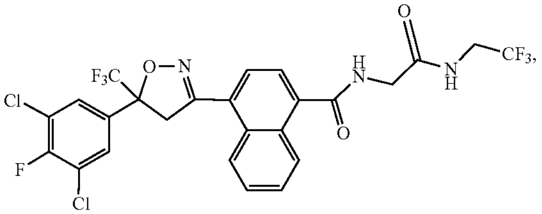

(IIf)

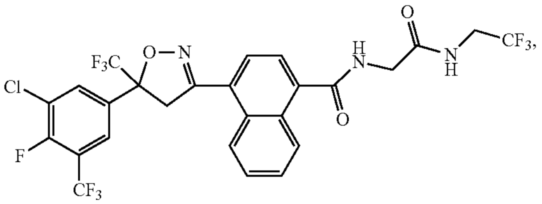

(IVa)

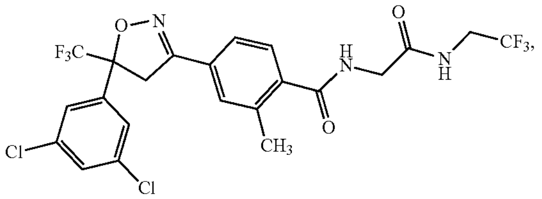

-continued (Va)

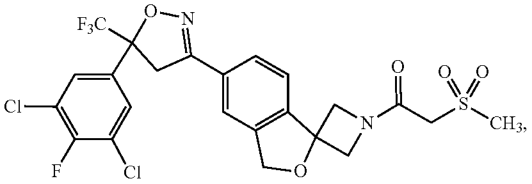

(VIa)

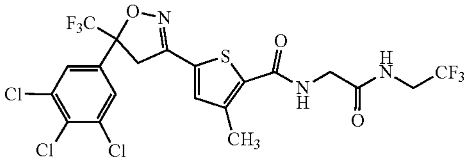

or (VIIa)

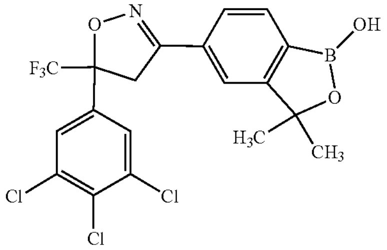

or a pharmaceutically acceptable salt thereof, b) about % to about 10% (w/w) of a pharmaceutically acceptable polymer;

c) about 50% to about 80% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

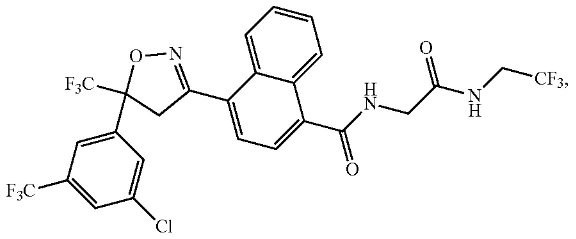

-continued (IId)

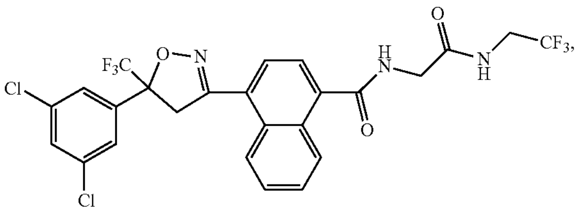

(IIe)

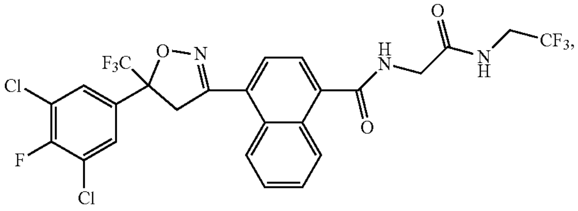

(IIf)

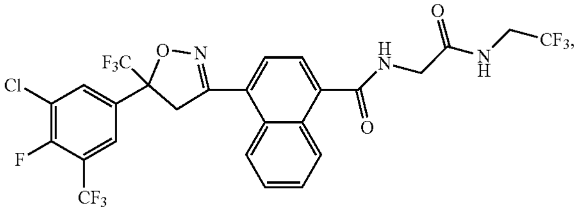

(IVa)

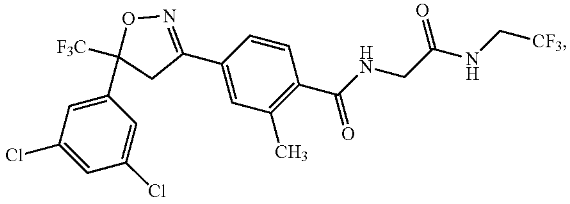

(Va)

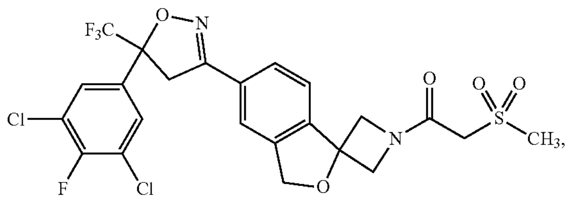

(VIa)

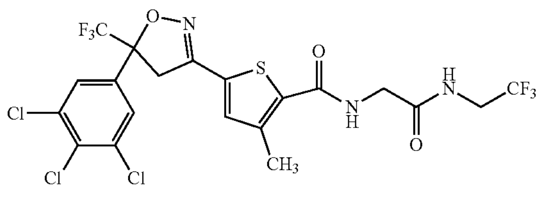

or

-continued (VIIa)

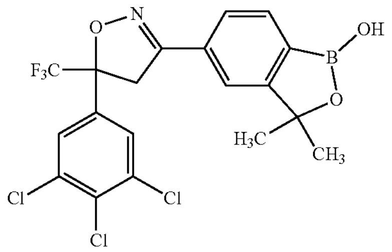

or a pharmaceutically acceptable salt thereof, b) about 10% to about 40% (w/w) of a pharmaceutically acceptable polymer;

c) about 60% to about 85% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

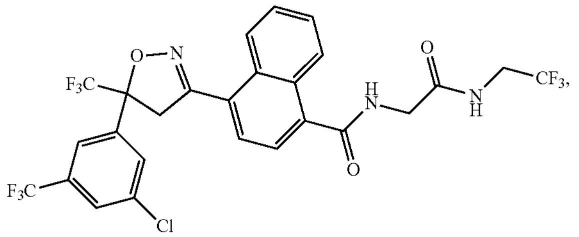

(IId)

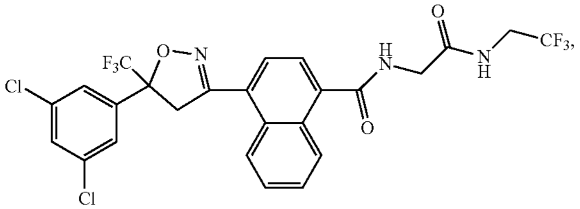

(IIe)

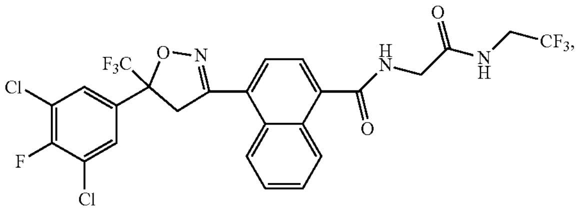

-continued (IIf)

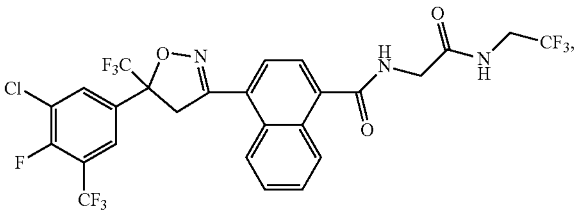

(IVa)

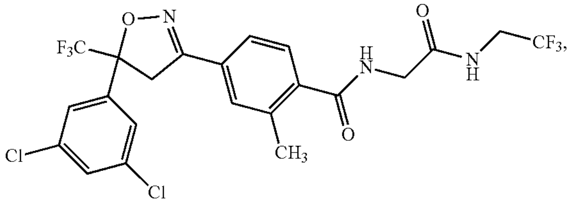

(Va)

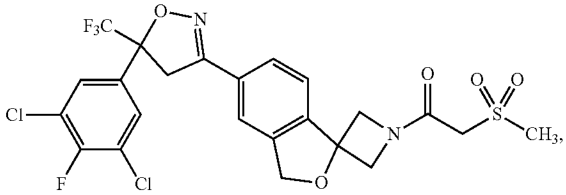

(VIa)

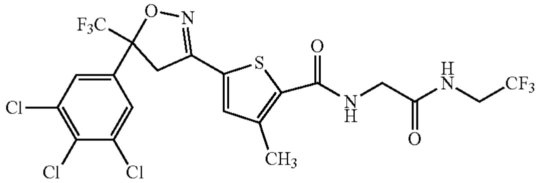

or (VIIa)

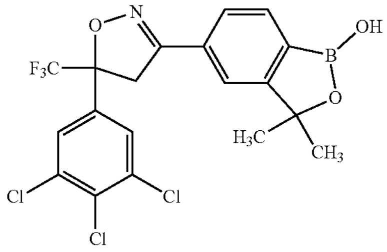

or a pharmaceutically acceptable salt thereof, b) about 3% to about 7% (w/w) of a pharmaceutically acceptable polymer;

c) about 60% to about 85% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In yet another embodiment the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

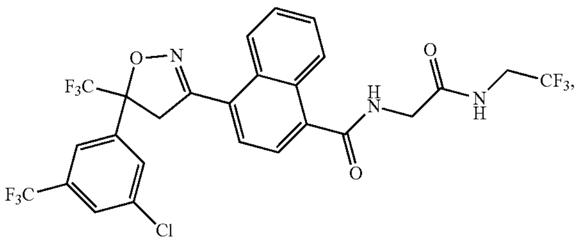

(IId)

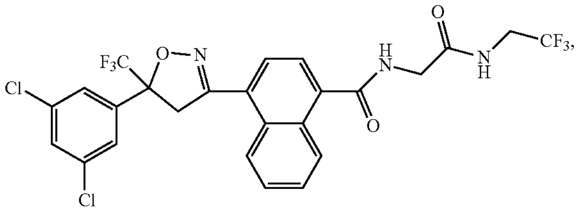

(IIe)

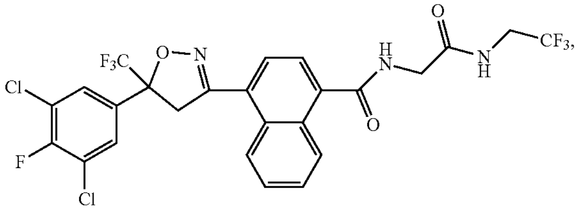

(IIf)

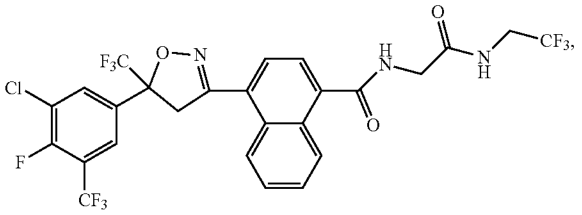

(IVa)

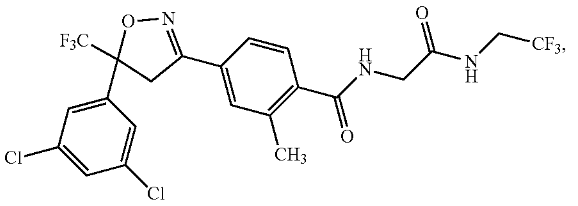

(Va)

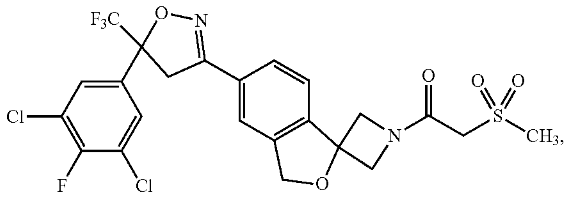

-continued (VIa)

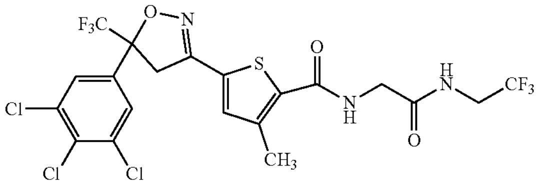

or (VIIa)

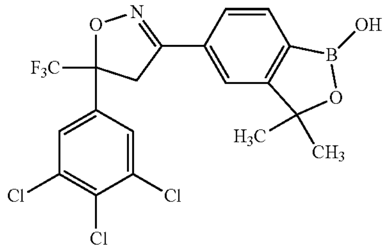

b) about 12% to about 38% (w/w) of a PLGA polymer;

c) about 55% to about 85% (w/w) of a mixture of a water miscible solvent and a water immiscible solvent;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In yet another embodiment the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

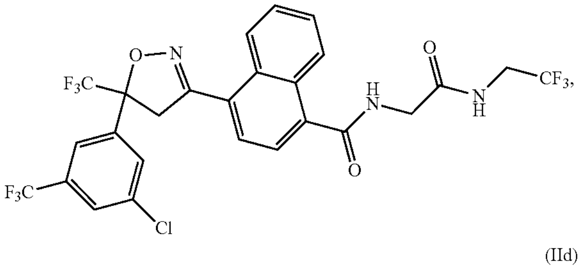

(IId)

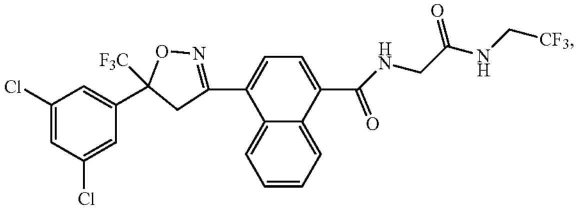

-continued (IIe)

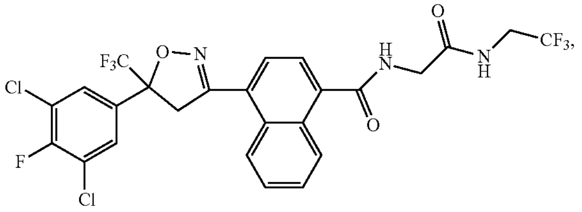

(IIf)

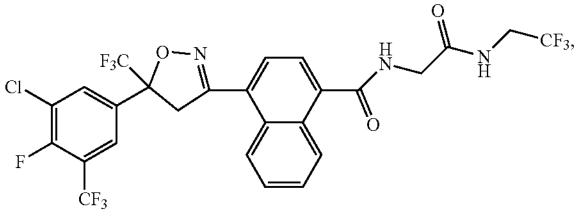

(IVa)

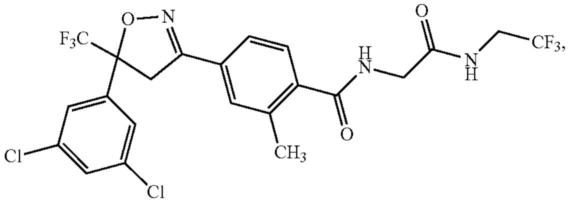

(Va)

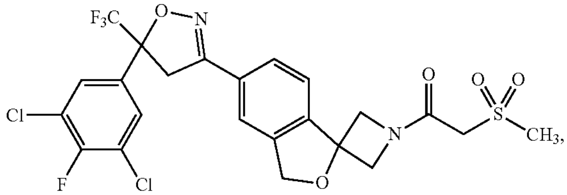

(VIa)

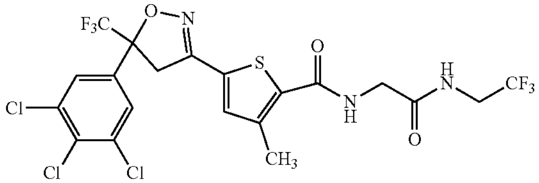

or (VIIa)

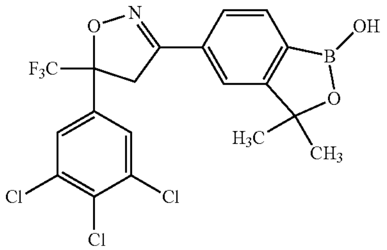

or a pharmaceutically acceptable salt thereof, b) about 1% to about 5% (w/w) of a PLGA polymer;

c) about 55% to about 85% (w/w) of a mixture of a water miscible solvent and a water immiscible solvent;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

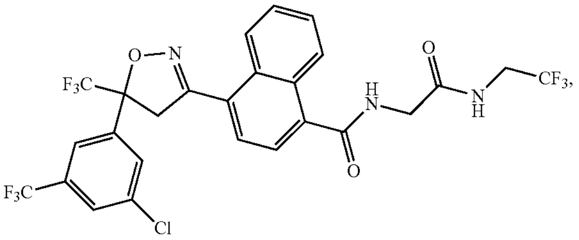

(IId)

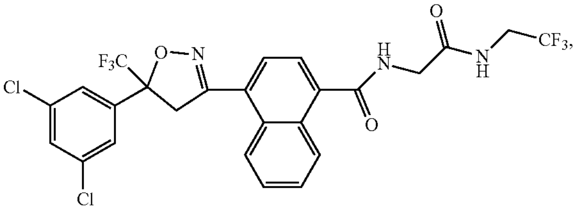

(IIe)

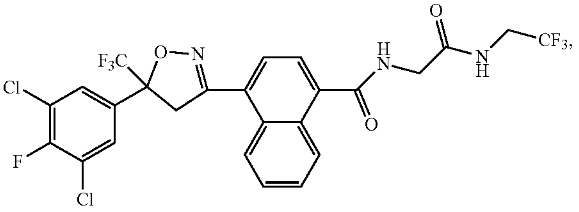

(IIf)

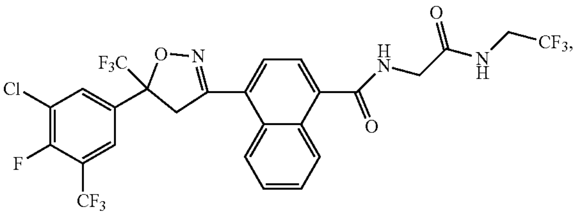

(IVa)

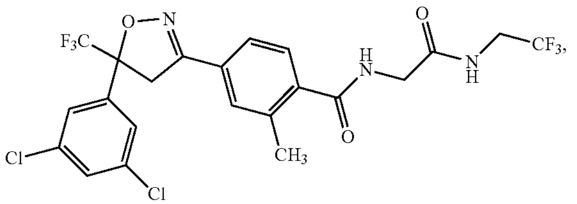

-continued (Va)

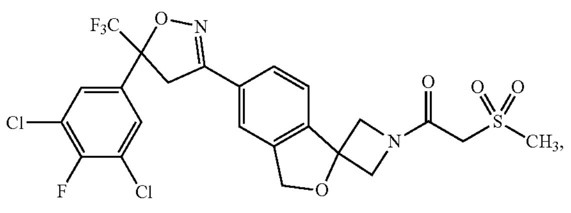

(VIa)

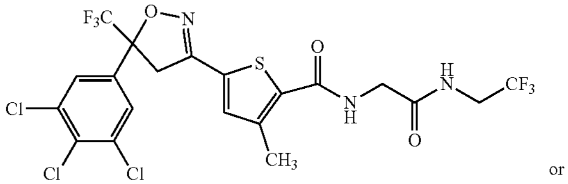

or (VIIa)

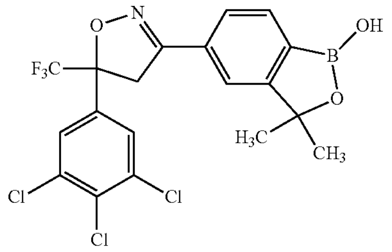

b) about 10% to about 35% (w/w) of a PLGA polymer;

c) about 60% to about 85% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol including ethanol, isopropanol, glycerol formal and Solketal; and an amide and the water immiscible solvent is selected from the group consisting of benzyl alcohol, a glycerol ester, a triglyceride and a propylene glycol ester;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 15 to 30% (w/w) of an isoxazoline active agent, such as, for example, any of the isoxazoline compounds provided for in the embodiments above (e.g., a compound of Formulae I-VIIa), such as, a compound of the formula:

(IIc)

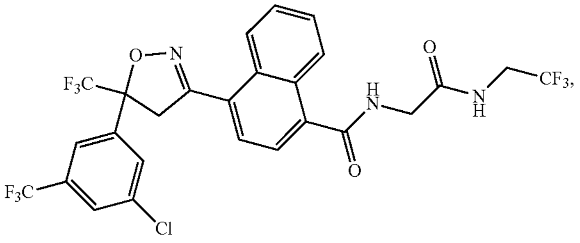

(IId)

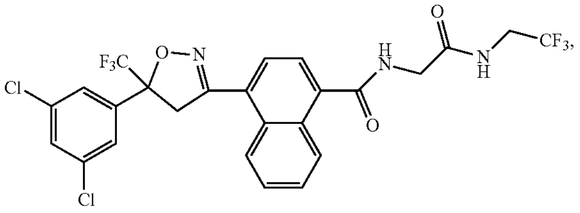

(IIe)

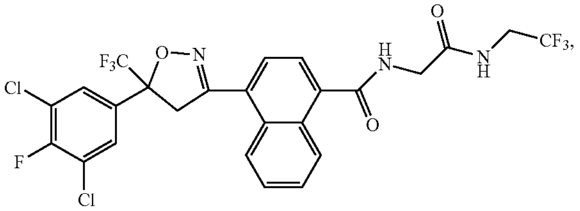

(IIf)

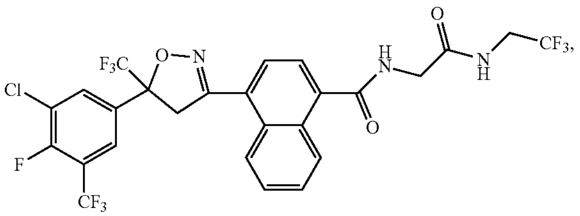

(IVa)

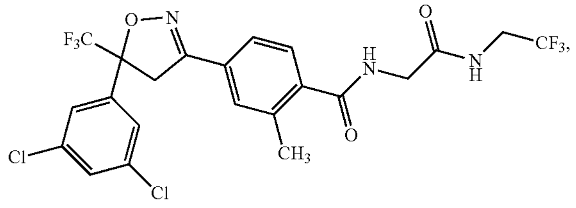

(Va)

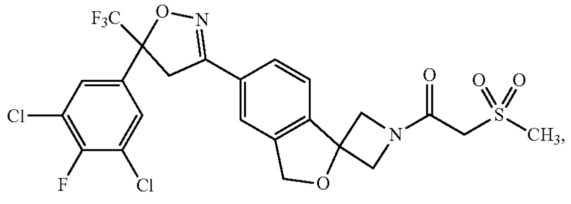

-continued (VIa)

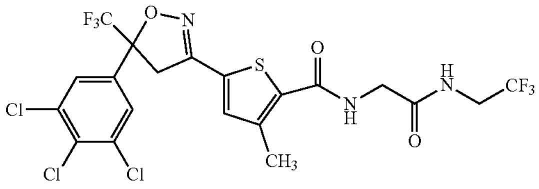

or (VIIa)

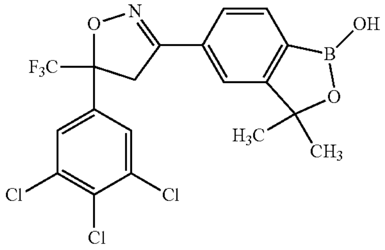

b) about 1% to about 7% (w/w) of a PLGA polymer;

c) about 60% to about 85% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol including ethanol, isopropanol, glycerol formal and Solketal; and an amide and the water immiscible solvent is selected from the group consisting of benzyl alcohol, a glycerol ester, a triglyceride and a propylene glycol ester;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 5 to 20% (w/w) of an isoxazoline active agent, such as, for example, any of the isoxazoline compounds provided for in the embodiments above (e.g., a compound of Formulae I-VIIa), such as, a compound of the formula:

(S)-IIc

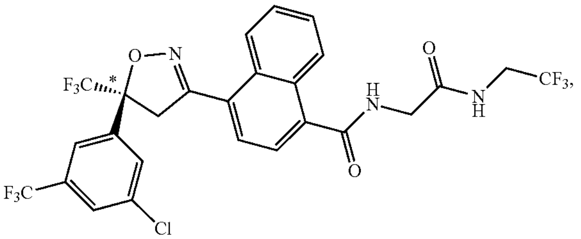

-continued (S)-IId

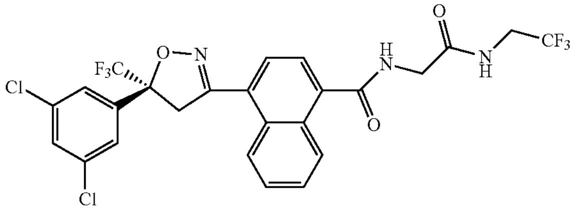

(S)-IIe

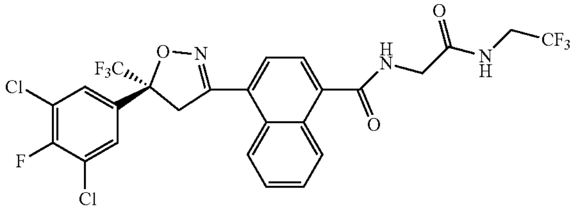

(S)-IIf

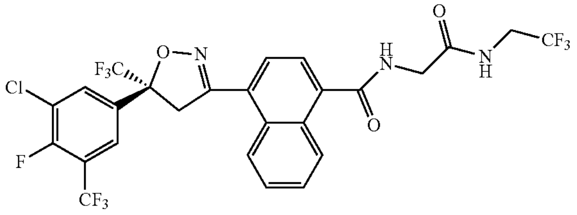

(S)-IVa

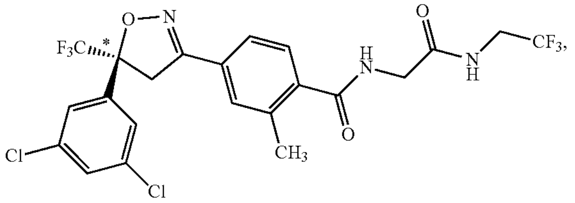

(S)-Va

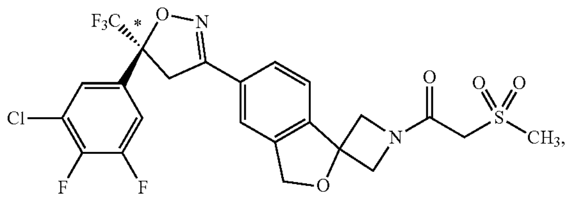

(S)-VIa

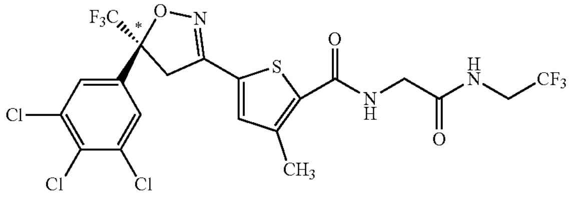

or

-continued (S)-VIIa

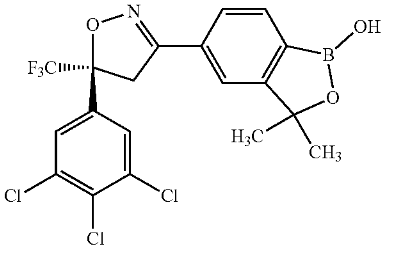

b) about 1% to about 28% (w/w) of a pharmaceutically acceptable polymer;

c) about 40% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 5 to 20% (w/w) of an isoxazoline active agent, such as, for example, any of the isoxazoline compounds provided for in the embodiments above (e.g., a compound of Formulae I-VIIa), such as, a compound of the formula:

(S)-IIc

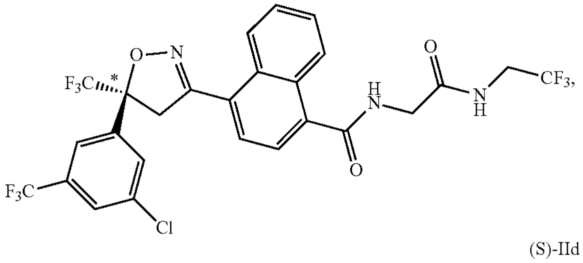

(S)-IId

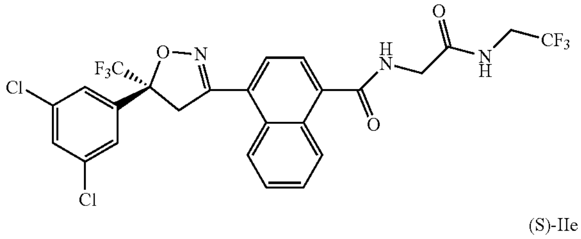

(S)-IIe

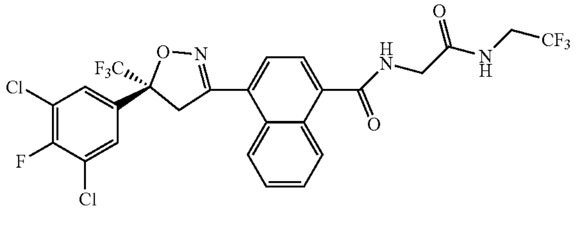

-continued (S)-IIf

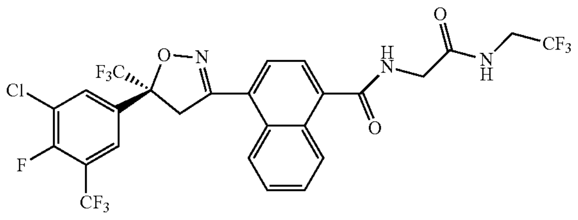

(S)-IVa

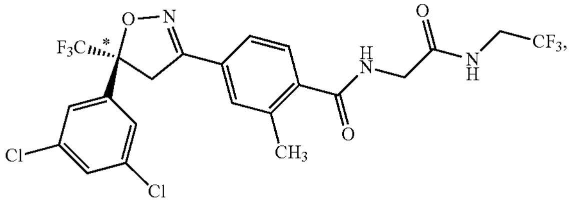

(S)-Va

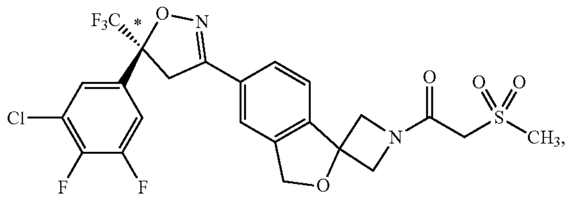

(S)-VIa

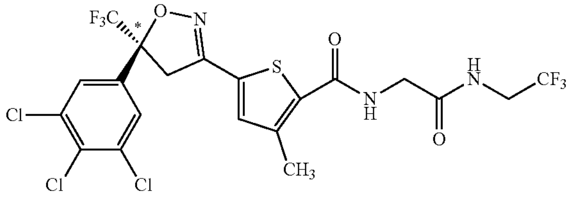

or (S)-VIIa

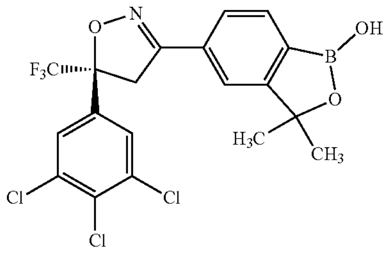

b) about 1% to about 30% (w/w) of a pharmaceutically acceptable polymer;

c) about 40% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In certain embodiments the present invention provides for extended release injectable formulations for the treatment and/or prophylaxis of parasitic infections and infestations of animals comprising:

a) about 5 to 15% (w/w) of an isoxazoline active agent, such as, for example, any of the isoxazoline compounds provided for in the embodiments above (e.g., a compound of Formulae I-VI), such as, a compound of the formula:

(S)-IIc

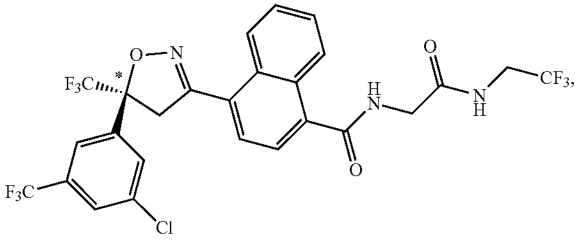

(S)-IId

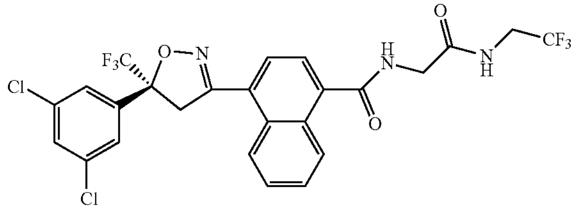

(S)-IIe

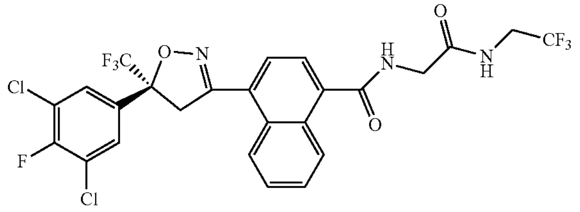

(S)-IIf

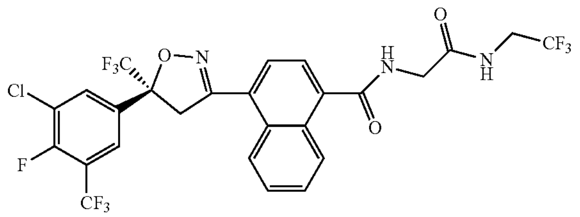

(S)-IVa

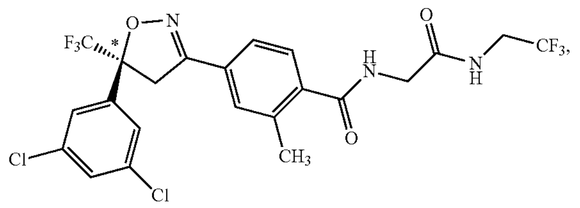

(S)-Va

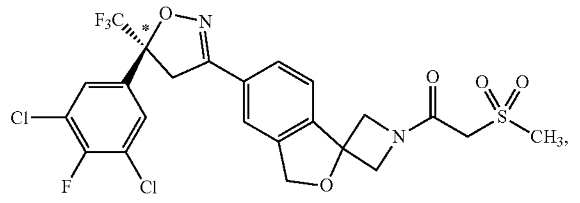

-continued (S)-VI

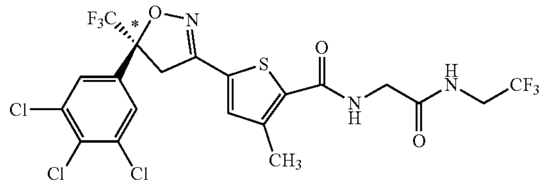

or (S)-VIIa

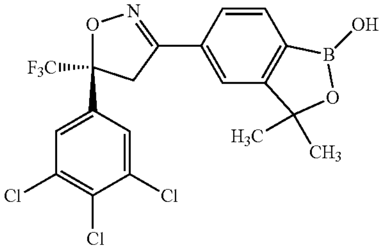

or a pharmaceutically acceptable salt thereof, b) about 1% to about 20% (w/w) of a pharmaceutically acceptable polymer;

c) about 50% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 5 to 15% (w/w) of an isoxazoline active agent, such as, for example, any of the isoxazoline compounds provided for in the embodiments above (e.g., a compound of Formulae I-VI), such as, a compound of the formula:

(S)-IIc

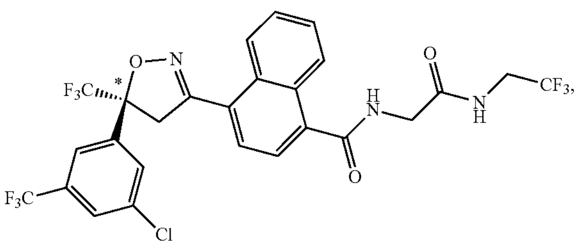

(S)-IId

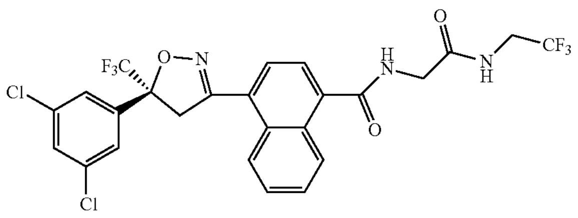

-continued (S)-IIe

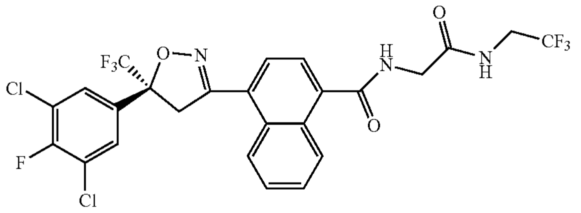

(S)-IIf

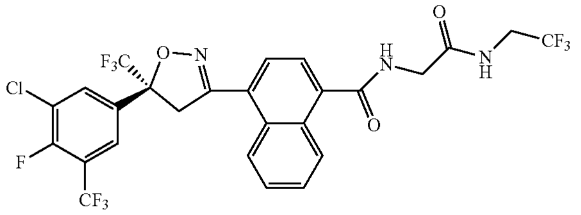

(S)-IVa

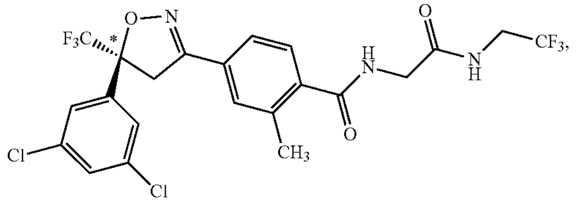

(S)-Va

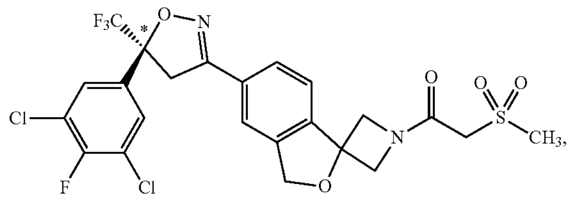

(S)-VI

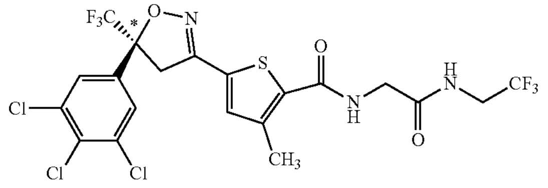

or (S)-VIIa

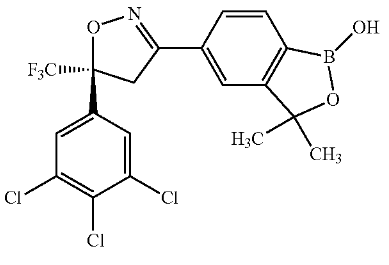

or a pharmaceutically acceptable salt thereof, b) about 5% to about 20% (w/w) of a pharmaceutically acceptable polymer;

c) about 60% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 5 to 15% (w/w) of an isoxazoline active agent, such as, for example, any of the isoxazoline compounds provided for in the embodiments above (e.g., a compound of Formulae I-VI), such as, a compound of the formula:

(S)-IIc

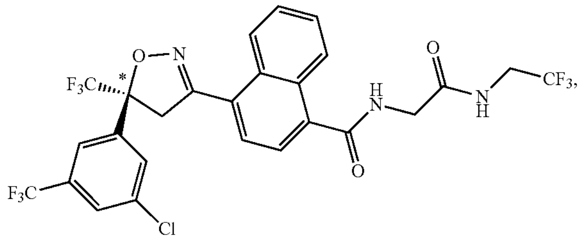

(S)-IId

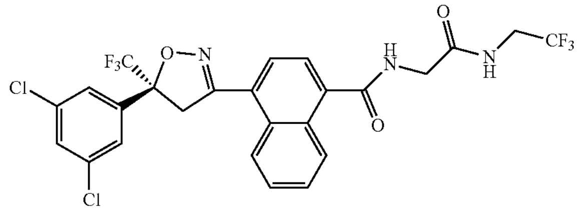

(S)-IIe

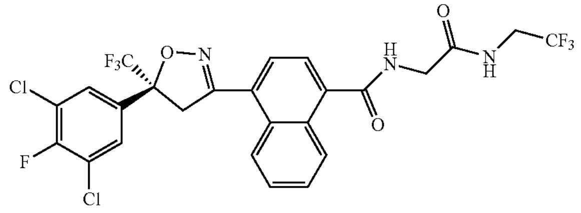

(S)-IIf

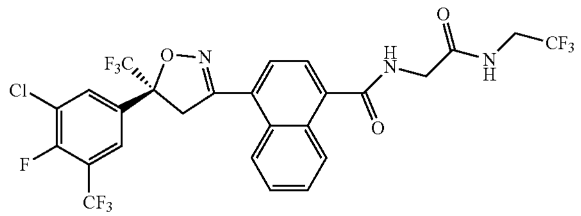

(S)-IVa

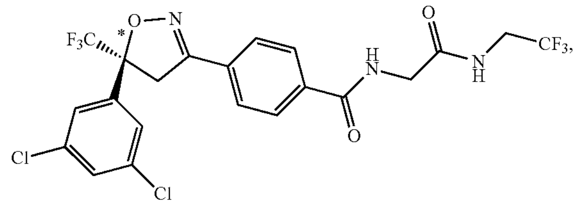

-continued (S)-Va

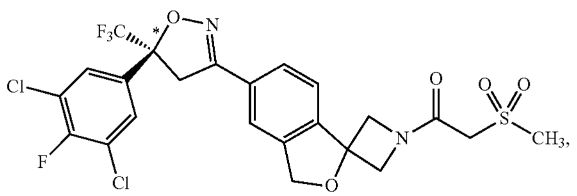

(S)-VI

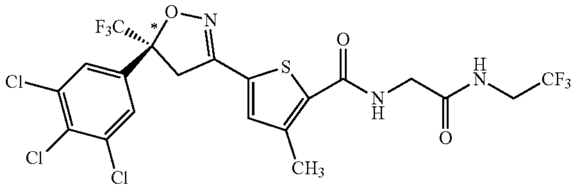

or (S)-VII

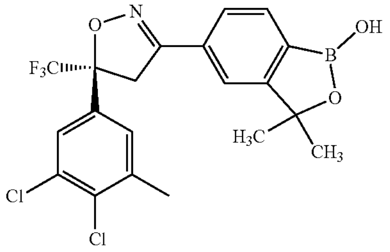

or a pharmaceutically acceptable salt thereof, b) about 1% to about 10% (w/w) of a pharmaceutically acceptable polymer;

c) about 60% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 5 to 15% (w/w) of an isoxazoline active agent, such as, for example, any of the isoxazoline compounds provided for in the embodiments above (e.g., a compound of Formulae I-VI), such as, a compound of the formula:

(S)-IIc

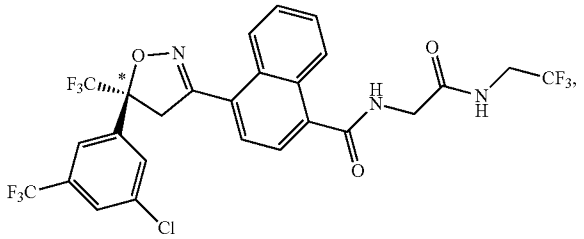

-continued (S)-IId

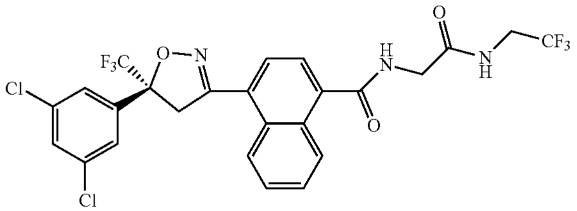

(S)-IIe

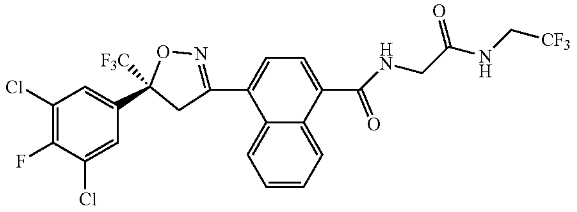

(S)-IIf

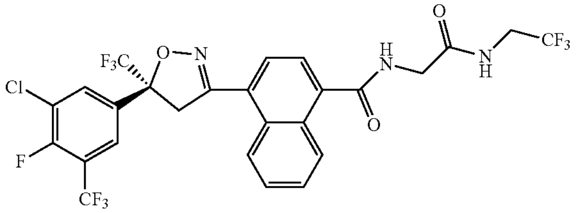

(S)-IVa

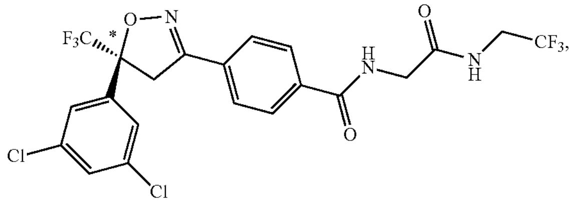

(S)-Va

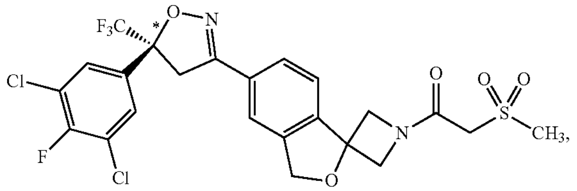

(S)-VI

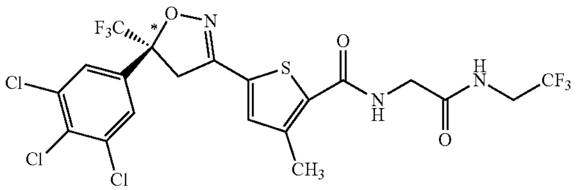

or

-continued (S)-VII

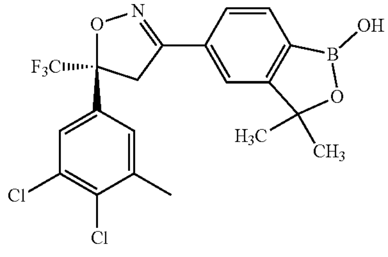

or a pharmaceutically acceptable salt thereof, b) about 3% to about 20% (w/w) of a pharmaceutically acceptable polymer;

c) about 70% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 5 to 15% (w/w) of an isoxazoline active agent, such as, for example, any of the isoxazoline compounds provided for in the embodiments above (e.g., a compound of Formulae I-VI), such as, a compound of the formula:

(S)-IIc

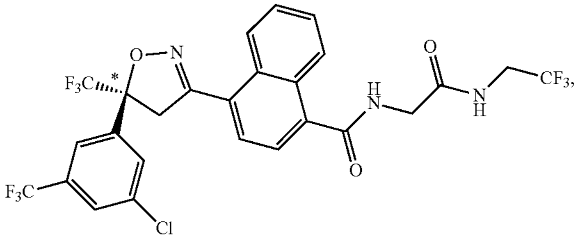

(S)-IId

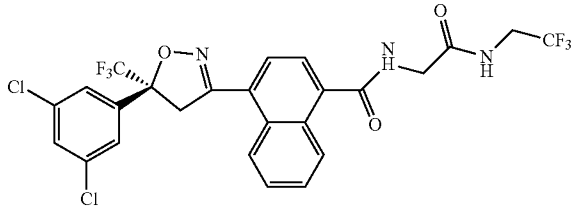

(S)-IIe

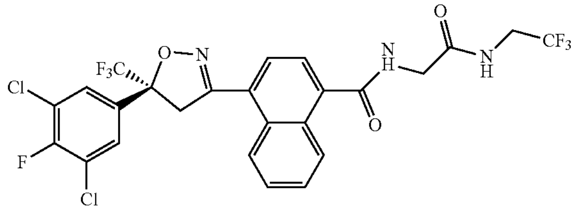

-continued (S)-IIf

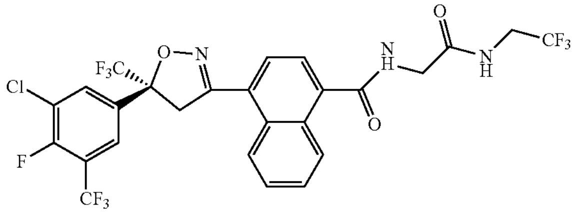

(S)-IVa

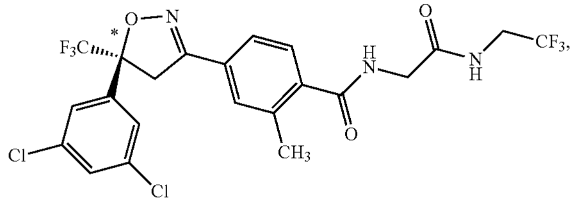

(S)-Va

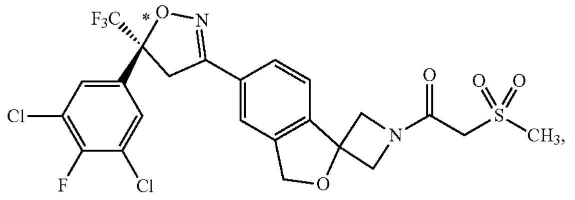

(S)-VI

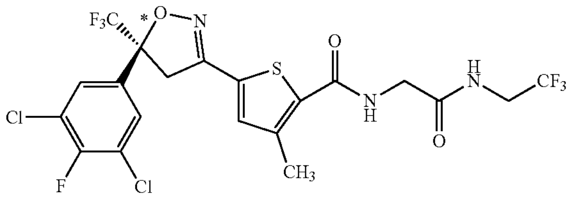

or (S)-VIIa

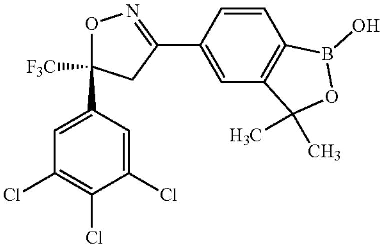

or a pharmaceutically acceptable salt thereof, b) about 1% to about 5% (w/w) of a pharmaceutically acceptable polymer;

c) about 70% to about 95% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 10 to 20% (w/w) of an isoxazoline active agent, such as, for example, any of the isoxazoline compounds provided for in the embodiments above (e.g., a compound of Formulae I-VI), such as, a compound of the formula:

(S)-IIc

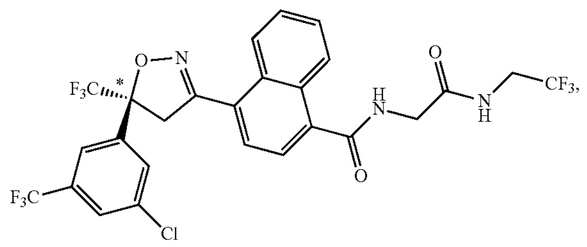

(S)-IId

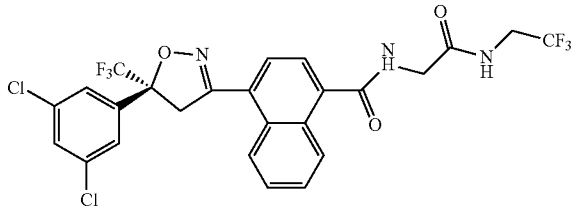

(S)-IIe

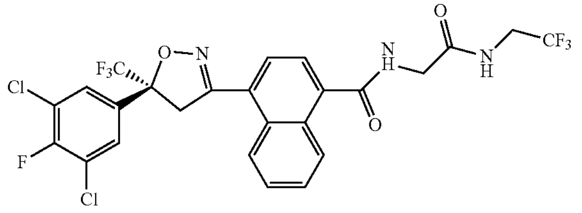

(S)-IIf

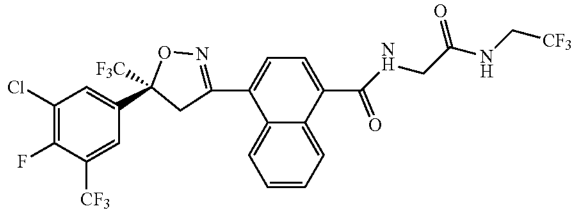

(S)-IVa

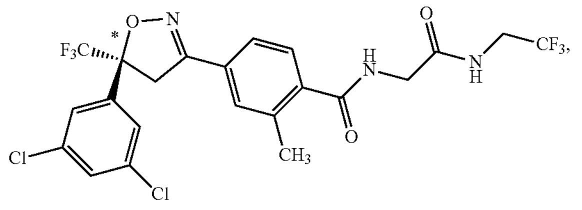

(S)-Va

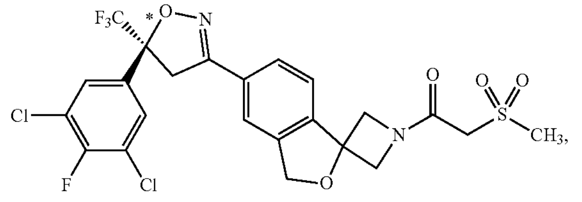

-continued (S)-VI

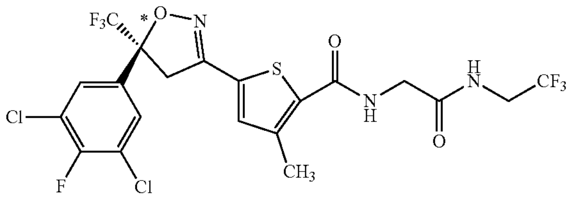

or (S)-VIIa

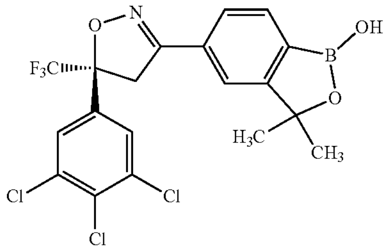

or a pharmaceutically acceptable salt thereof, b) about 8% to about 28% (w/w) of a pharmaceutically acceptable polymer;

c) about 60% to about 90% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

In another embodiment the present invention provides for extended release injectable formulations for the treatment and/or prophylaxis of parasitic infections and infestations of animals comprising:

a) about 10 to 20% (w/w) of an isoxazoline active agent, such as, for example, any of the isoxazoline compounds provided for in the embodiments above (e.g., a compound of Formulae I-VI), such as, a compound of the formula:

(S)-IIc

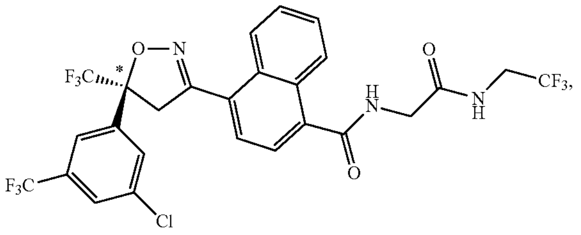

(S)-IId

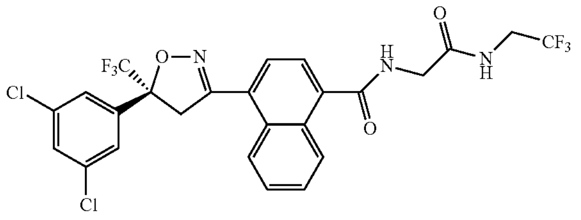

-continued (S)-IIe

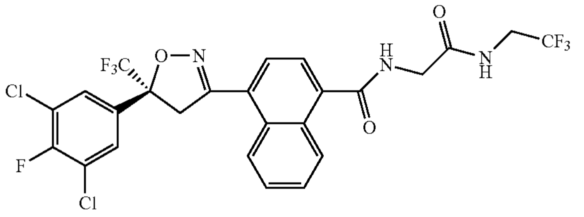

(S)-IIf

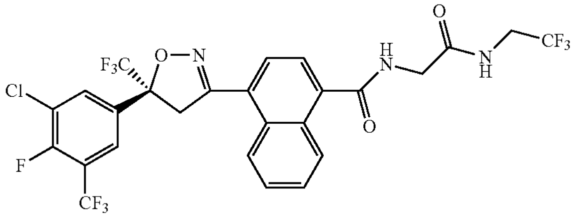

(S)-IVa

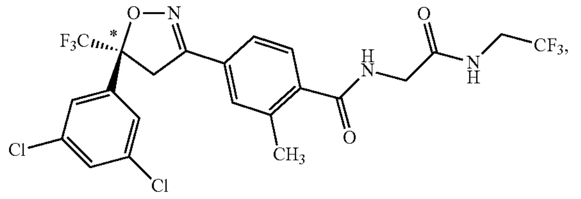

(S)-Va

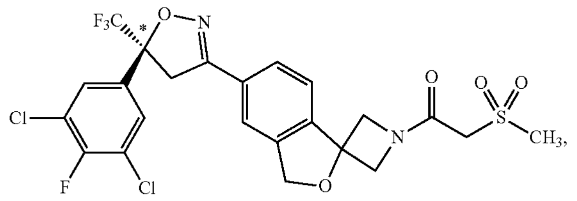

(S)-VI

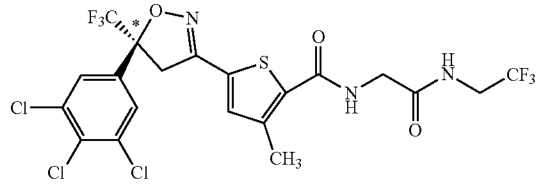

or (S)-VIIa

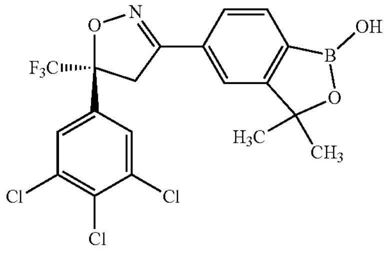

or a pharmaceutically acceptable salt thereof, b) about 3% to about 7% (w/w) of a pharmaceutically acceptable polymer;

c) about 60% to about 90% (w/w) of solvent or mixture of solvents;

d) optionally, about 0.01% to about 2.0% (w/w) of an antioxidant;

e) optionally, about 0.1% to about 10% (w/w) of a surfactant; and f) optionally, about 0.01% to about 5.0% (w/w) of a pharmaceutically acceptable additive, excipient or mixtures thereof.

Another embodiment of the present invention is an extended release injectable formulation for the treatment and/or prevention of parasitic infections and infestations of animals consisting essentially of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) a pharmaceutically acceptable polymer;

c) at least one solvent or a mixture of solvents;

d) optionally, an antioxidant;

e) optionally, a surfactant; and f) optionally, at least one pharmaceutically acceptable additive, excipient or mixtures thereof.

In another embodiment, the present invention provides an extended release injectable formulation for the treatment and/or prevention of parasitic infections and infestations of animals consisting essentially of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 1% to about 30% (w/w) of a PLGA polymer;

c) about 40% to about 98% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting essentially of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 1% to about 20% (w/w) of a PLGA polymer;

c) about 40% to about 98% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting essentially of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 5% to about 20% (w/w) of a PLGA polymer;

c) about 40% to about 90% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting essentially of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 5% to about 15% (w/w) of a PLGA polymer;

c) about 50% to about 95% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting essentially of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 1% to about 10% (w/w) of a PLGA polymer;

c) about 50% to about 95% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

Another embodiment of the present invention is an extended release injectable formulation for the treatment and/or prevention of parasitic infections and infestations of animals consisting of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) a pharmaceutically acceptable biodegradable polymer;

c) at least one solvent wherein said solvent is a polar solvent miscible in water;

d) optionally, an antioxidant;

e) optionally, about 0.1% to about 10% (w/w) of a surfactant; and f) optionally, at least one pharmaceutically acceptable additive, excipient or mixtures thereof.

In another embodiment, the present invention provides an extended release injectable formulation for the treatment and/or prevention of parasitic infections and infestations of animals consisting of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 1% to about 30% (w/w) of a PLGA polymer;

c) about 40% to about 98% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 1% to about 20% (w/w) of a PLGA polymer;

c) about 40% to about 98% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 5% to about 20% (w/w) of a PLGA polymer;

c) about 40% to about 90% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 1% to about 10% (w/w) of a PLGA polymer;

c) about 50% to about 98% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the present invention provides an extended release injectable formulation for the treatment and/or prevention of parasitic infections and infestations of animals consisting of:

a) an antiparasitic effective amount of at least one isoxazoline active agent, such as, for example, any of the isoxazoline compounds provided for in the embodiments above (e.g., a compound of any of Formulae I-VIIa), and optionally at least one additional active agent as identified in this application;

b) about 5% to about 15% (w/w) of a PLGA polymer;

c) about 50% to about 95% (w/w) of a mixture of a water miscible solvent and a water immiscible solvent, wherein the water miscible solvent is selected from the group consisting of a cyclic carbonate, dimethylisosorbide, dimethylsulfoxide, 2-pyrrolidone, N-methylpyrrolidone, N-octylpyrrolidone, a liquid polyethylene glycol, a poloxamer, an alcohol, Solketal and an amide and the water immiscible solvent is selected from the group consisting of benzyl alcohol, a glycerol ester, glycerol formal, a triglyceride, a propylene glycol ester and glycerol formal;

d) optionally, about 0.01% to about 2% (w/w) of an antioxidant;

e) optionally, about 0.1% to about 10% (w/w) of a surfactant; and f) optionally, about 0.1% to about 5% (w/w) of a pharmaceutically acceptable additive, excipient or mixtures thereof.

In another embodiment, the pharmaceutically acceptable polymer in the extended release injectable formulations described above may be a copolymer of a polylactides and polyglycolides and the solvent may be a single solvent, such as, for example a cyclic carbonate (e.g., ethylene carbonate or propylene carbonate) or a mixture of solvents comprising, for example, a cyclic carbonate, a glycerol ester (e.g., glycerol triacetate), and, optionally, a poloxamer (for example, P-124), which can function either as a solvent or a surfactant. In yet a further embodiment, the extended release injectable formulations, described above, may further include an antioxidant, such as, butylated hydroxytoluene (BHT).

Further embodiments of the invention are any of the extended release injectable formulations provided for above wherein: the ratio of PLGA to the isoxazoline active agent to the copolymer of polylactides and polyglycolides is about 1.5:1 to about 1:1.5 (weight:weight); the weight average molecular weight of the copolymer of polylactides and polyglycolides is about 5 kDa to about 20 kDa; and the concentration of the copolymer of polylactides and polyglycolides is about 8% (w/w) to about 20% (w/w) (e.g., 12.5% (w/w) or 13% (w/w)). In a further embodiment, any of the extended release injectable formulations provided for above may further comprise 0.5% (w/w) to about 20% (w/w) of poloxamer (e.g., about 1% (w/w) to about 3% (w/w)). In yet a further embodiment, the copolymer of polylactides and polyglycolides may have a lactide to glycolide ratio of about 75:25 (weight:weight).

The extended release formulations of the invention are prepared by adding to the solvent or solvent mixture, any non-polymer excipients (e.g. if present antioxidants, surfactants, etc.), followed by addition of the active ingredient(s) with mixing. When the active ingredient and non-active excipients are fully solubilized, the pharmaceutically acceptable polymer(s) are added with mixing until completely dissolved. Of course, the compositions may be prepared by other appropriate processes known in the art as long as the resulting formulation is a homogeneous liquid formulation suitable for use.

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. The term "consisting of" excludes any element, step or ingredient not specified in the claims.

Definitions

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "extended release" or "extended release formulation" or "extended release composition" as used herein means a dosage form that is formulated in such a manner to make the active agent(s) contained therein to be available over an extended period of time due to the interaction of the formulation components in combination with the natural pharmacokinetic or pharmacodynamic characteristics of the active agent(s). This definition is consistent with the use of the term known and accepted in the veterinary field as described in the article "*Terminology Challenges: Defining Modified Release Dosage Forms in Veterinary Medicine*" by Marilyn N. Martinez, Danielle Lindquist and Sanja Modric (Journal of Pharmaceutical Sciences, vol. 99, no. 8, August 2010).

For example, the extended release formulations according to the present invention would be understood to provide an efficacy of at least 90% against fleas and/or ticks for at least 3 months as described herein.

The term "animal" is used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

The term "essentially pure" is used herein to indicate that a compound or an enantiomer is at least about 90% (w/w) pure, at least about 95% (w/w), or at least about 98% (w/w) pure, or higher.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. "Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-$S(O)_2$—, wherein alkyl is as defined above. Similarly, the term "haloalkylsulfonyl" refers to haloalkyl-$S(O)_2$— where haloalkyl is as defined above.

The term alkylamino and dialkylamino refer to alkyl-NH— and $(alkyl)_2N$— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl) amino, or trialkylsilyl.

The terms "aralkyl" or "arylalkyl" refers to an aryl group that is bonded to the parent compound through a diradical alkylene bridge, $(-CH_2-)_n$, where n is 1-12 and where "aryl" is as defined above. "Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thienyl, furyl, pyrrolyl, imidazolyl, oxazolyl, isoxazolyl, isothiazolyl, pyrazolyl benzofuranyl, and benzothienyl. Heteroaryl rings may be unsubstituted or substituted by one or more moieties as described for aryl above. The term "heteroarylene" (where the heteroaryl group is a bridging group) should be construed accordingly.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfonyl, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like. The term "heterobicyclylene" (where the bicyclic heterocyclic group is a bridging group) should be construed accordingly.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl ($-CH_2Cl$), dichloromethyl ($-CHCl_2$), trichloromethyl ($-CCl_3$)).

By the term "enriched" is meant when the weight:weight ratio is at least approximately 1.05 or higher in favor of one enantiomer over the other. Preferably, the weight:weight ratio is at least approximately 1.05 or higher in favor of the enantiomer that displays significant in vitro and in vivo activity (the eutomer).

Stereoisomers and Polymorphic Forms

As noted above, it will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses compositions comprising the specific enantiomers or diastereomers of each compound as well as mixtures of different enantiomers and/or diastereomers of the compounds of the invention that possess the useful properties described herein. In addition, the invention encompasses compositions comprising one or more conformational isomers (e.g. rotamers) as well as mixtures of conformational isomers. Conformational isomers of the isoxazoline compounds may be produced by a restriction of rotation about the amide bond bonded to the aryl or heteroaryl ring (e.g. the amide bonded to the naphthyl group in Formula (IIc)). The optically active forms can be prepared by, for example, resolution of the racemic forms by selective crystallization techniques, by synthesis from optically active precursors, by chiral synthesis, by chromatographic separation using a chiral stationary phase or by enzymatic resolution.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents. In some embodiments, the compositions of the invention may include up to 15% (w/w), up to 20% (w/w), or up to 30% (w/w) of a particular solid form.

Salts

Also contemplated within the scope of the invention are acid or base salts, where applicable, of the compounds of the invention provided for herein.

The term "acid salt" contemplates salts of the compounds with all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, a-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base salt" contemplates salts of the compounds with all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

In another embodiment, the extended release injectable formulations of present invention comprise an effective amount of at least one isoxazoline or a pharmaceutically acceptable salt thereof in combination at least one other active agent. In one embodiment, the extended release injectable compositions comprise an effective amount of at least one isoxazoline compound of formula (I) to (VIIa), or a pharmaceutically acceptable salt thereof, in combination with at least one other active agent that is systemically-active.

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ectoparasiticidal and/or endoparasiticidal agents.

Veterinary pharmaceutical agents that may be included in the compositions of the invention are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodium thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, known in the art may be combined with the isoxazoline compounds in the extended release injectable compositions of the invention. Examples of such arylpyrazole compounds include but are not limited to fipronil, pyriprole, ethiprole and those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, GA).

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 $A_1$, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" $12^{th}$ ed., S. Budavari, Ed., Merck & Co., Inc. Whitehouse Station, New Jersey (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859, 657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In yet another embodiment, the invention provides the extended release formulations of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula IIc) in combination with a macrocyclic lactone active agent.

In yet another embodiment, the invention provides the extended release formulations of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula IIc) in combination with ivermectin, eprinomectin, selamectin, milbemycin oxime or moxidectin.

In another embodiment, the invention provides the extended release formulations of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide enriched in the (S)-enantiomer or as the substantially pure (S)-enantiomer (Compound of formula (S)-IIc) in combination with a macrocyclic lactone active agent.

In yet another embodiment, the invention provides the extended release formulations of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide enriched in the (S)-enantiomer or as the substantially pure (S)-enantiomer (Compound of formula (S)-IIc) in combination with ivermectin, eprinomectin, selamectin, milbemycin oxime or moxidectin.

In another embodiment of the invention, the invention comprises an extended release injectable formulation comprising an isoxazoline compound in combination with systemically-acting compounds from a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

In an embodiment, the extended release injectable formulations of present invention comprise an effective amount of at least one isoxazoline of Formula (I) to (VI), or a pharmaceutically acceptable salt thereof, in combination with methoprene or pyriproxyfen.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the extended release formulations of the present invention. These include pyrethrins (which include cinerin I, cinerin II, jasmolin I, jasmolin II, pyrethrin I, pyrethrin II and mixtures thereof) and pyrethroids, and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox. In one embodiment, the compositions can include permethrin in combination with an isoxazoline active agent.

In some embodiments, the extended release injectable formulations of the present invention may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the extended release injectable formulations of the present invention may include an imidazothiazole compounds including, but not limited to, tetramisole, levamisole and butamisole. In still other embodiments, the extended release formulations of the present invention may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the extended release injectable formulations of the present invention may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, a-santonin and kainic acid.

In other embodiments, the extended release injectable formulations of the present invention of the invention may include antitrematodal agents. Suitable antitrematodal agents include, but are not limited to, the miracils such as miracil D and mirasan; praziquantel, epsiprantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the extended release formulations of the present invention of the invention including, but not limited to, praziquantel, epsiprantel, and arecoline in various salt forms, bunamidine, niclosamide, nitroscanate, paromomycin and paromomycin II.

In yet other embodiments, the extended release injectable formulations of the present invention may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, piperonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a- tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with an isoxazoline compounds in the extended release formulations of the present invention can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126 (Pt 1):79-86). In another embodiment, the depsipeptide is PF1022A or a derivative thereof.

In another embodiment, the extended release injectable formulations of the present invention may comprise an active agent from the neonicotinoid class of pesticides. The neonicotinoids bind and inhibit insect specific nicotinic acetylcholine receptors. In one embodiment, the neonicotinoid insecticidal agent that can be combined with an isoxazoline compound to form an extended release injectable formulation of the invention is imidacloprid.

Imidacloprid is a well-known neonicotinoid active agent and is the key active ingredient in the topical parasiticide products Advantage®, Advantage® II, K9 Advantix®, and K9 Advantix® II sold by Bayer Animal Health and the oral soft-chewable formulation Advantus™ from Piedmont Animal Health. Agents of this class are described, for example, in U.S. Pat. No. 4,742,060 or in EP 0 892 060.

In another embodiment, the extended release injectable formulations of the present invention may comprise nitenpyram, another active agent of the neonicotinoid class of pesticides. Nitenpyram has the following chemical structure and is the active ingredient in the oral product CAPSTAR™ Tablets sold by Novartis Animal Health.

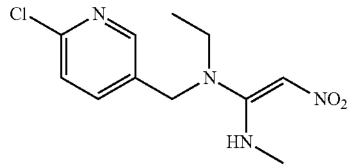 [SMILES: CCN(Cc1ccc(Cl)nc1)/C(=C/[N+](=O)[O-])NC]

Nitenpyram is active against adult fleas when given daily as an oral tablet. Nitenpyram works by interfering with normal nerve transmission and leads to the death of the insect.

Nitenpyram has a very fast onset of action against fleas. For example, CAPSTAR™ Tablets begin to act against fleas in as early as 30 minutes after administration and is indicated for use as often as once a day. However, nitenpyram is only known to be effective when administered orally as a systemic parasiticide, as with CAPSTAR™ Tablets.

In certain embodiments, an insecticidal agent that can be combined with the extended release formulations of the present invention is a semicarbazone, such as metaflumizone.

In another embodiment, the extended release injectable formulations of the present invention may advantageously include a combination of isoxazoline compounds known in the art. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelmintic, anti-parasitic and insecticidal agents) may be added to the extended release formulations of the present invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The formulations may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the. the extended release formulations of the present invention These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The compositions of the invention may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964,621, which is incorporated herein by reference.

The extended release injectable formulations of the present invention may also be combined with paraherquamide compounds and derivatives of these compounds, including derquantel (see Ostlind et al., *Research in Veterinary Science,* 1990, 48, 260-61; and Ostlind et al., *Medical and Veterinary Entomology,* 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In another embodiment of the invention, the compositions may include a spinosyn active agent produced by the soil actinomycete Saccharopolyspora *spinosa* (see, for example Salgado V. L. and Sparks T. C., "*The Spinosyns: Chemistry, Biochemistry, Mode of Action, and Resistance*," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, the additional active agent is included in the extended release formulations of the present invention in an amount of between about 0.1 pg and about 1000 mg. More typically, the additional active agent may be included in an amount of about 10 μg to about 500 mg, about 1 mg to about 300 mg, about 10 mg to about 200 mg or about 10 mg to about 100 mg.

In other embodiments of the invention, the additional active agent may be included in the composition to deliver a dose of about 5 μg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 μg/kg to about 200 μg/kg or about 0.1 mg/kg to about 1 mg/kg of weight of animal. In still another embodiment of the invention, the additional active agent is included in a dose between about 0.5 mg/kg to about 50 mg/kg.

In one embodiment, the extended release injectable formulations of the present invention, which include at least an isoxazoline active agent, a pharmaceutically acceptable polymer and a solvent, have been surprisingly discovered to be stable and effective against a broad spectrum of ectoparasites, and possibly also endoparasites if another active is included, for an extended period of time; e.g., a period from three (3) up to twelve (12) months or longer, while exhibiting favorable properties with respect to the site of injection.

Dosage forms may contain from about 0.5 mg to about 5 g of a combination of active agents. More typically, the amount of active agent(s) in the compositions of the invention will be from about 1 mg to about 3 g. In another embodiment, the amount of active agent(s) in the compositions will be from about 20 mg to about 3 g. In another embodiment, the amount of active agent(s) present in the compositions will be from about 20 mg to about 2 g, about 20 mg to about 1.5 g or about 20 mg to about 1 g. In other embodiments, the amount of active agent(s) in the compositions will be from about 20 mg to about 500 mg, about 30 mg to about 200 mg or about 50 mg to about 200 mg. In still another embodiment, the amount of active agent(s) present in the compositions will be from about 50 mg to about 2 g, about 50 mg to about 1 g or about 50 mg to about 500 mg. In yet another embodiment of the invention, the about of active agent(s) present will be from about 100 mg to about 2 g, about 100 mg to about 1 g or about 100 mg to about 500 mg.

In another embodiment, the amount of active agent(s) present in an amount of from about 1 mg to about 500 mg of an active agent, about 1 mg to about 100 mg or about 1 mg to about 25 mg. In still other embodiments, the amount of the active agent present in the compositions is about 10 mg about 50 mg or about 10 mg to about 100 mg. In other embodiments, the amount of active agent present in the compositions is about 50 mg to about 200 mg, about 100 mg to about 300 mg, about 100 mg to about 400 mg, about 200 mg to about 500 mg, about 300 mg to about 600 mg, about 400 mg to about 800 mg, or about 500 mg to about 1000 mg.

The compositions of the invention are made by mixing the appropriate amount of the active agents, pharmaceutically acceptable polymer, a solvent and, optionally, an antioxidant, pharmaceutically acceptable additive and/or excipient to form a formulation of the invention. In some embodiments the formulations of the present invention can be obtained by following the method of making these forms described above by the description of making these forms found in general formulation text known to those in the art, e.g. *Remington—The Science and Practice of Pharmacy* (*21st Edition*) (2005), *Goodman & Gilman's The Pharmacological Basis of Therapeutics* (*11th Edition*) (2005) and *Ansel's Pharmaceutical Dosage Forms and Drug* 25 *Delivery Systems* (*8th Edition*), edited by Allen et al., Lippincott Williams & Wilkins, (2005).

Methods of Treatment

In another aspect of the invention, a method for preventing or treating a parasite infestation/infection in an animal is provided, comprising administering to the animal an extended release injectable formulation comprising an effective amount of at least one isoxazoline compound, a pharmaceutically acceptable polymer and a solvent. The formulations of the invention have long-lasting efficacy against ectoparasites (e.g. fleas and ticks) and in certain embodiments in which the compositions include an additional active agent they may also be active against endoparasites that harm animals.

In one embodiment of the invention, methods for the treatment or prevention of a parasitic infestation or infection in a domestic animal are provided, which comprise administering an extended release injectable formulation comprising an effective amount of at least one isoxazoline active agent to the animal. Ectoparasites against which the methods and compositions of the invention are effective include, but are not limited to, fleas, ticks, mites, mosquitoes, flies and lice. In certain embodiments wherein the inventive formulations include one or more additional active agents that are active against internal parasites the compositions and methods of the invention may also be effective against endoparasites including, but not limited to, cestodes, nematodes, hookworms and roundworms of the digestive tract of animals and humans.

In one embodiment for treatment against ectoparasites, the ectoparasite is one or more insect or arachnid including those of the genera *Ctenocephalides, Rhipicephalus, Dermacentor, Ixodes, Amblyomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor* and/or *Ixodes*. The ectoparasites treated include but are not limited to fleas, ticks, mites, mosquitoes, flies, lice, blowfly and combinations thereof. Specific examples include, but are not limited to, cat and dog fleas (*Ctenocephalides* sp. such as *Ctenocephalides felis, Ctenocephalides canis*, and the like), ticks (*Rhipicephalus* sp., *Ixodes* sp., *Dermacentor* sp., *Amblyomma* sp. and the like), and mites (*Demodex* sp., *Sarcoptes* sp., *Otodectes* sp. and the like), lice (*Trichodectes* sp., *Cheyletiella* sp., *Linognathus* sp., and the like), mosquitoes (*Aedes* sp., *Culex* sp., *Anopheles* sp., and the like) and flies (*Haematobia* sp.

including *Haematobia irritans, Musca* sp., *Stomoxys* sp. including *Stomoxys calcitrans, Dermatobia* sp., *Cochliomyia* sp., and the like).

Additional examples of ectoparasites include but are not limited to the tick genus *Rhipicephalus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In some embodiments of the invention, the composition can also be used to treat against endoparasites such as those helminths selected from the group consisting of Anaplocephala, *Ancylostoma, Necator, Ascaris, Capillaria, Cooperia, Dipylidium, Dirofilaria, Echinococcus, Enterobius, Fasciola, Haemonchus, Oesophagostomum, Ostertagia, Toxocara, Strongyloides, Toxascaris, Trichinella, Trichuris, Angiostrongylus* and *Trichostrongylus*, among others.

In one embodiment, the invention provides methods for the treatment and prevention of parasitic infections and infestations of animals (either wild or domesticated), including livestock and companion animals such as cats, dogs, horses, birds including chickens, sheep, goats, pigs, deer, turkeys and cattle, with the aim of ridding these hosts of parasites commonly encountered by such animals.

In an embodiment, the invention provides methods and compositions for the treatment or prevention of parasitic infections and infestations in companion animals including, but not limited to, cats and dogs. The methods and compositions are particularly effective for preventing or treating parasitic infestations of cats and dogs with fleas and ticks.

In another embodiment, the methods and compositions of the invention are used for the treatment or prevention of parasitic infections and infestations in cattle or sheep. When treating livestock animals such as cattle or sheep, the methods and compositions are particularly effective against *Rhipicephalus* (formerly *Boophilus*) *microplus, Haematobia irritans* (horn fly), *Stomoxys calcitrans* (stable fly), and sheep myiasis such as *Lucilia sericata, Lucilia cuprina* (known as blowfly strike in Australia, New Zealand and South Africa).

The terms “treating” or “treat” or “treatment” are intended to mean the administration of an extended release formulation of the present invention to an animal that has a parasitic infestation for the eradication of the parasite or the reduction of the number of the parasites infesting the animal undergoing treatment. It is noted that the compositions of the invention may be used to prevent such a parasitic infestation.

The terms “prevent”, “prevention” or “prophylaxis” are intended to mean the administration of the extended release formulations of the present invention to the animal before the parasitic infection or infestation has occurred in order to keep said infection or infestation from occurring.

The formulations of the invention are administered in parasiticidally effective amounts which are which are suitable to control the parasite in question to the desired extent, as described below. In each aspect of the invention, the compounds and compositions of the invention can be applied against a single pest or combinations thereof.

By “antiparasitic effective amount” is intended a sufficient amount of a composition of the invention to eradicate or reduce the number of parasites infesting the animal. In some embodiments, an effective amount of the active agent achieves at least 70% efficacy (% reduction vs. control) against the target parasite. In other embodiments, an effective amount of the active agent achieves at least 80%, or at least 90% efficacy against the target pests.

Preferably, an effective amount of the active agent will achieve at least 95%, at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In some embodiments for companion animals, the dose of the isoxazoline active agent administered from the extended release injectable formulations of the invention is between about 0.1 to about 50 mg per kg of body weight. More typically the dose of the isoxazoline active agent administered is about 0.5 to about 40 mg/kg or about 0.5 to about 30 mg/kg body weight. In another embodiment, the dose of the isoxazoline active agent administered is about 10 to about 40 mg/kg, about 15 to about 35 mg/kg or about 20 to about 30 mg/kg of body weight. In another embodiment, the dose of the isoxazoline active agent will be about 20 to about 25 mg/kg of body weight.

In other embodiments, the dose administered may be lower depending on the animal and the isoxazoline administered. For example, if the composition comprises the more active enantiomer of the isoxazoline compounds a lower dose may be administered. In some embodiments, the dose is from about 0.1 to about 30 mg/kg of body weight. In another embodiment, the dose may be from about 0.1 to about 20 mg/kg or about 0.1 to about 10 mg/kg of body weight. In other embodiments, the dose may be from about 1 to about 20 mg/kg of body weight or about 1 to about 10 mg/kg. In yet another embodiment, the dose may be from about 5 to about 20 mg/kg or about 10 to about 20 mg/kg of body weight. In another embodiment, the dose may be from about 10 to about 30 mg/kg of body weight.

In other embodiments for the treatment of livestock animals such as cattle or sheep, doses of the isoxazoline active agent administered may be about 0.1 to about 40 mg/kg of body weight.

More typically the doses administered will be about 1 to about 30 mg/kg, about 1 to about 20 mg/kg or about 1 to about 10 mg/kg of bodyweight. In yet another embodiment, the dose may be from about 10 to about 25 mg/kg, about 15 to about 30 mg/kg of body weight or about 20 to about 30 mg/kg of body weight.

In one embodiment of the method of use in dogs or cats, the extended release formulations of the present invention comprising an isoxazoline compound has an efficacy against fleas and/or ticks of at least about 90.0% or higher for about 3 months, or longer. In another embodiment, the extended release formulations of the present invention provide an efficacy against fleas and/or ticks of at least 95.0% or higher for about, 3 months or longer. In yet another embodiment, the extended release formulations of the invention provide an efficacy against fleas and/or ticks of at least 90% or higher for about 6 months or longer. In yet another embodiment, the extended release formulations of the invention provide an efficacy against fleas and/or ticks of at least 95% or higher for about 6 months or longer. In another embodiment, the extended release formulations of the invention provide an efficacy against fleas and/or ticks of at least 90% or higher for about 9 months or longer. In yet another embodiment, the extended release formulations of the invention provide an efficacy against fleas and/or ticks of at least 90% or higher for about 12 months or longer. In another embodiment, the extended release formulations of the present invention provide an efficacy against fleas and/or ticks in cats and dogs of at least about 90% for two months, or longer. In another embodiment, the extended release formulations of the present invention efficacy against fleas and/or ticks in cats and dogs of about 95% for about 3 months, or longer. In still another embodiment, the compositions provide an efficacy of about 95% for about 5 months or longer.

In another aspect of the invention, a kit for the treatment or prevention of a parasitic infestation in an animal is provided, which comprises an extended release formulation of the invention and a syringe or dosing device.

EXAMPLES

The invention is further described by the following non-limiting examples which further illustrate the invention, and are not intended, nor should they be interpreted to, limit the scope of the invention.

Formulation Examples

The following extended release injectable formulations were prepared by mixing the following ingredients. Unless indicated otherwise, the concentrations of each component is percent (%) weight per weight (w/w) and MW refers to weight average molecular weight.

Example 1

| | |
|---|---|
| Compound of formula (IIc) | 26% |
| Medium molecular weight (MMW) PLGA (50:50) | 1% |
| Propylene carbonate | 50.9% |
| Triacetin | 22.2% |
| BHT | 0.02%. |

Example 2

| | |
|---|---|
| Compound of formula (IIc) | 26% |
| Low molecular weight (LMW) PLGA (50:50) | 5% |
| Propylene carbonate | 48.0% |
| Triacetin | 21.0% |
| BHT | 0.02%. |

Example 3

| | |
|---|---|
| Compound of formula (IIc) | 26% |
| MMW PLGA (50:50) | 5% |
| Propylene carbonate | 48.0% |
| Triacetin | 21.0% |
| BHT | 0.02%. |

Example 4

| | |
|---|---|
| Compound of formula (IIc) | 20% |
| MMW PLGA (50:50) | 3% |
| Propylene carbonate | 53.9% |
| Triacetin | 23.1% |
| BHT | 0.02%. |

Example 5

| | |
|---|---|
| Compound of formula (IIc) | 26% |
| MMW PLGA (50:50) | 3% |
| Propylene carbonate | 49.7% |
| Triacetin | 21.3% |
| BHT | 0.02%. |

Example 6

| | |
|---|---|
| Compound of formula (IIc) | 20% |
| LMW PLGA (50:50) | 5% |
| Propylene carbonate | 52.5% |
| Triacetin | 22.5% |
| BHT | 0.02%. |

Example 7

| | |
|---|---|
| Compound of formula (S)-IIc | 20% |
| MMW PLGA (50:50) | 5% |
| Propylene carbonate | 52.5% |
| Triacetin | 22.5% |
| BHT | 0.02%. |

Example 8

| | |
|---|---|
| Compound of formula (S)-IIc | 10% |
| LMW PLGA (50:50) | 5% |
| Propylene carbonate | 59.5% |
| Triacetin | 25.5% |
| BHT | 0.02%. |

Example 9

| | |
|---|---|
| Compound of formula (S)-IIc | 10% |
| LMW PLGA (50:50) | 2.5% |
| Propylene carbonate | 61.25% |
| Triacetin | 26.25% |
| BHT | 0.02%. |

Example 10

| | |
|---|---|
| Compound of formula (IIc) | 20% |
| LMW PLGA (50:50) | 7% |
| Propylene carbonate | 51.1% |
| Triacetin | 21.9% |
| BHT | 0.02%. |

Example 11

| | |
|---|---|
| Compound of formula (IIc) | 20% |
| MMW PLGA (50:50) | 5% |
| Propylene carbonate | 52.5% |
| Triacetin | 22.5% |
| BHT | 0.02%. |

Example 12

| | |
|---|---|
| Compound of formula (IIc) | 20% |
| High molecular weight (HMW) PLGA (75:25) | 5% |
| Propylene carbonate | 52.5% |
| Triacetin | 22.5% |
| BHT | 0.02%. |

Example 13

| | |
|---|---|
| Compound of formula (IIc) | 15% |
| HMW PLGA (75:25) | 5% |
| Propylene carbonate | 56% |
| Triacetin | 24% |
| BHT | 0.02%. |

Example 14

| | |
|---|---|
| Compound of formula (IIc) | 20% |
| LMW PLGA (50:50) | 5% |
| Propylene carbonate | 75% |
| BHT | 0.02%. |

Example 15

| | |
|---|---|
| Compound of formula (IIc) | 20% |
| LMW PLGA (50:50) | 5% |
| Propylene carbonate | 73% |
| Poloxamer 124 | 2% |
| BHT | 0.02%. |

Example 16

| | |
|---|---|
| Compound of formula (IIc) | 20% |
| LMW PLGA (50:50) | 5% |
| Propylene carbonate | 55% |
| Poloxamer 124 | 20% |
| BHT | 0.02%. |

Example 17

| | |
|---|---|
| Compound of formula (IIc) | 20% |
| HMW PLGA (50:50) | 5% |
| Propylene carbonate | 52.5% |
| Triacetin | 22.5% |
| BHT | 0.02%. |

Example 18

| | |
|---|---|
| Compound of formula (IIc) | 20% |
| HMW PLGA (50:50) | 5% |
| Propylene carbonate | 51.1% |
| Triacetin | 21.9% |
| Poloxamer 124 | 2% |
| BHT | 0.02%. |

Example 19

| | |
|---|---|
| Compound of formula (IIc) | 12.5% |
| HMW PLGA (75:25) | 12.5% |
| Propylene carbonate | 52.5% |
| Triacetin | 22.5% |
| BHT | 0.02%. |

Example 20

| | |
|---|---|
| Compound of formula (S)-IIc | 12.5% |
| HMW PLGA (75:25) | 12.5% |
| Propylene carbonate | 52.5% |
| Triacetin | 22.5% |
| BHT | 0.02%. |

Example 21

| | |
|---|---|
| Compound of formula (IIc) | 12.5% |
| HMW PLGA (75:25) | 12.5% |
| Propylene carbonate | 52.5% |
| Triacetin | 22.5% |
| BHT | 0.02%. |

Example 22

| | |
|---|---|
| Compound of formula (IIc) | 12.5% |
| HMW PLGA (75:25) | 20% |
| Propylene carbonate | 47.5% |
| Triacetin | 20.3% |
| BHT | 0.02%. |

Example 23

| | |
|---|---|
| Compound of formula (IIc) | 12.5% |
| HMW PLGA (75:25) | 15% |
| Propylene carbonate | 50.7% |
| Triacetin | 21.8% |
| BHT | 0.02%. |

Example 24

| | |
|---|---|
| Compound of formula (IIc) | 12.5% |
| HMW PLGA (75:25) | 12.5% |
| Propylene carbonate | 51.1% |
| Triacetin | 21.9% |
| Poloxamer 124 | 2% |
| BHT | 0.02%. |

Example 25

| | |
|---|---|
| Compound of formula (IIc) | 12.5% |
| LMW PLGA (75:25) | 12.5% |
| Propylene carbonate | 52.5% |
| Triacetin | 22.5% |
| BHT | 0.02%. |

Example 26

| | |
|---|---|
| Compound of formula (IIc) | 12.5% |
| LMW PLGA (50:50) | 12.5% |
| Propylene carbonate | 52.5% |
| Triacetin | 22.5% |
| BHT | 0.02%. |

Efficacy Examples

The following examples demonstrate the efficacy of the extended release injectable compositions of the invention against ectoparasites in companion and farm animals.

Example 27

A study was conducted to determine the level of isoxazoline compound (IIc) in the plasma of dogs over time after a single subcutaneous injection of the extended release formulations of the invention. Accordingly, the extended release formulations of Examples 1, 2 and 3 were administered to dogs at a dose of at 25 mg/kg once at Day 0. The concentration of compound (IIc) in the plasma was measured intermittently to determine if the concentration of the compound was sufficient to control fleas. The concentration of compound (IIc) in the bloodstream has been strongly correlated with efficacy against fleas (see, for example, Letendre et al., *Veterinary Parasitology* 201 (2014) 190-197). Thus, the concentration of about 20 ng/ml of compound (IIc) is known to effectively control fleas on dogs ($EC_{90}$ 23 ng/ml). In the study, the concentration of compound (IIc) was found to be above 20 ng/ml for at least 180 days post treatment. Accordingly, the extended release formulations of Examples 1, 2 and 3 would be expected to be highly efficacious to control fleas in dogs for at least 180 days.

Example 28

In another study, the concentration of isoxazoline compound (IIc) in the plasma of dogs was measured after a single subcutaneous injection of the extended release formulations of Examples 4 and 5. The concentration of compound (IIc) was found to be above about 20 ng/ml for at least about 5 months (154 days) after treatment. Thus, the extended release formulations of Examples 4 and 5 would be expected to be highly efficacious against fleas on dogs for at least about five months.

Example 29

In separate study, the concentration of isoxazoline compound (IIc) in the plasma of dogs was measured after a single subcutaneous injection of the extended release formulations of Examples 4 and 5. The concentration of compound (IIc) was found to be above about 20 ng/ml for greater than seven months (238 days) after treatment.

Example 30

| | |
|---|---|
| Compound of formula (IIc) | 26% |
| PLGA (50:50) (MW~52 kDa) | 1% |
| Propylene carbonate | 22.16% |
| Triacetin | 50.8% |
| BHT | 0.02% |

Example 31

| | |
|---|---|
| Compound of formula (IIc) | 26% |
| PLGA (50:50) (MW~9 kDa) | 5% |
| Propylene carbonate | 20.95% |
| Triacetin | 48.03 |
| BHT | 0.02% |

Example 32

| | |
|---|---|
| Compound of formula (IIc) | 26% |
| PLGA (50:50) (MW~52 kDa) | 5% |
| Propylene carbonate | 20.95% |
| Triacetin | 48.03 |
| BHT | 0.02% |

Example 33

| | |
|---|---|
| Compound of formula (IIc) | 20% |
| PLGA (70:30) (MW~52 kDa) | 3% |
| Propylene carbonate | 53.89% |
| Triacetin | 23.09% |
| BHT | 0.02% |

Example 34

| | |
|---|---|
| Compound of formula (IIc) | 26% |
| PLGA (70:30) (MW~52 kDa) | 3% |
| Propylene carbonate | 49.69% |
| Triacetin | 21.29% |
| BHT | 0.02% |

Example 35

| | |
|---|---|
| Compound of formula (IIc) | 20% |
| PLGA (50:50) (MW ~9) | 5% |
| Propylene carbonate | 52.5% |
| Triacetin | 22.5% |
| BHT | 0.02% |

Example 36

| | |
|---|---|
| Compound of formula (S)-IIc | 20% |
| PLGA (50:50) (MW ~9) | 5% |
| Propylene carbonate | 52.5% |
| Triacetin | 22.5% |
| BHT | 0.02% |

Example 37

| | |
|---|---|
| Compound of formula (S)-IIc | 10% |
| PLGA (50:50) (MW ~9) | 5% |
| Propylene carbonate | 59.5% |
| Triacetin | 25.5% |
| BHT | 0.02% |

Example 38

| | |
|---|---|
| Compound of formula (S)-IIc | 10% |
| PLGA (50:50) (MW ~9) | 2.5% |
| Propylene carbonate | 61.25% |
| Triacetin | 26.25% |
| BHT | 0.02% |

Example 39

| | |
|---|---|
| Compound of formula (IIc) | 20% |
| PLGA (50:50) (MW ~ 9) | 7% |
| Propylene carbonate | 51.1% |
| Triacetin | 21.9% |
| BHT | 0.02% |

Example 40

| | |
|---|---|
| Compound of formula (IIc) | 20% |
| PLGA (50:50) (MW ~52) | 5% |
| Propylene carbonate | 52.5% |
| Triacetin | 22.5% |
| BHT | 0.02% |

Example 41

| | |
|---|---|
| Compound of formula (IIc) | 20% |
| PLGA (75:25) (MW ~111-115) | 5% |
| Propylene carbonate | 52.5% |
| Triacetin | 22.5% |
| BHT | 0.02% |

Example 42

| | |
|---|---|
| Compound of formula (IIc) | 15% |
| PLGA (75:25) (MW ~111-115) | 5% |
| Propylene carbonate | 56% |
| Triacetin | 24% |
| BHT | 0.02% |

Example 43

| | |
|---|---|
| Compound of formula (IIc) | 20% |
| PLGA (50:50) (MW ~9) | 5% |
| Propylene carbonate | 75% |
| BHT | 0.02% |

Example 44

| | |
|---|---|
| Compound of formula (IIc) | 20% |
| PLGA (50:50) (MW ~9) | 5% |
| Propylene carbonate | 73% |
| Poloxamer 124 | 2% |
| BHT | 0.02% |

Example 45

| | |
|---|---|
| Compound of formula (IIc) | 20% |
| PLGA (50:50) (MW ~9) | 5% |
| Propylene carbonate | 55% |
| Poloxamer 124 | 20% |
| BHT | 0.02% |

Example 46

| | |
|---|---|
| Compound of formula (IIc) | 12.5% |
| PLGA (75:25) (MW ~111-115) | 12.5% |
| Propylene carbonate | 52.5% |
| Triacetin | 22.5% |
| BHT | 0.02% |

Example 47

| | |
|---|---|
| Compound of formula (IIc) | 12.5% |
| PLGA (75:25) (MW ~111-115) | 20% |
| Propylene carbonate | 47.7% |
| Triacetin | 20.3% |
| BHT | 0.02% |

Example 48

| | |
|---|---|
| Compound of formula (IIc) | 12.5% |
| PLGA (75:25) (MW ~111-115) | 15% |
| Propylene carbonate | 50.7% |
| Triacetin | 21.8% |
| BHT | 0.02% |

Example 49

| | |
|---|---|
| Compound of formula (IIc) | 12.5% |
| PLGA (75:25) (MW ~111-115) | 12.5% |
| Propylene carbonate | 51.1% |
| Triacetin | 21.9% |
| Poloxamer 124 | 2% |
| BHT | 0.02% |

Example 50

| | |
|---|---|
| Compound of formula (IIc) | 12.5% |
| PLGA (75:25) (MW ~9) | 12.5% |
| Propylene carbonate | 52.5% |
| Triacetin | 22.5% |
| BHT | 0.02% |

Example 51

| | |
|---|---|
| Compound of formula (IIc) | 12.5% |
| PLGA (50:50) (MW ~9) | 12.5% |
| Propylene carbonate | 52.5% |
| Triacetin | 22.5% |
| BHT | 0.02% |

Example 52

| | |
|---|---|
| Compound of formula (S)-IIc | 12.5% |
| PLGA (75:25) (MW ~111-115) | 12.5% |
| Propylene carbonate | 52.5% |
| Triacetin | 22.5% |
| BHT | 0.02% |

Example 53

| | |
|---|---|
| Compound of formula (IIc) | 12.5% |
| PLGA (50:50) (MW ~9) | 12.5% |
| Propylene carbonate | 52.5% |
| Triacetin | 22.5% |
| BHT | 0.02% |

Example 54

| | |
|---|---|
| Compound of formula (S)-IIc | 12.5% |
| PLGA (50:50) (MW ~9) | 12.5% |
| Propylene carbonate | 52.5% |
| Triacetin | 22.5% |
| BHT | 0.02% |

Example 55

| | |
|---|---|
| Compound of formula (S)-IIc | 12.5% |
| PLGA (50:50) (MW ~52) | 12.5% |
| Propylene carbonate | 52.5% |
| Triacetin | 22.5% |
| BHT | 0.02% |

Example 56

| | |
|---|---|
| Compound of formula (S)-IIc | 12.5% |
| PLGA (50:50) (MW ~111-115) | 12.5% |
| Propylene carbonate | 52.5% |
| Triacetin | 22.5% |
| BHT | 0.02% |

Example 57

| | |
|---|---|
| Compound of formula (S)-IIc | 12.5% |
| PLGA (50:50) (MW ~9) | 12.5% |
| Propylene carbonate | 51.1% |
| Triacetin | 21.9% |
| Poloxamer-124 | 2% |
| BHT | 0.02% |

Example 58

| | |
|---|---|
| Compound of formula (S)-IIc | 12.5% |
| PLGA (75:25) (MW ~9) | 15% |
| Propylene carbonate | 50.7% |
| Triacetin | 21.8% |
| BHT | 0.02% |

Example 59

| | |
|---|---|
| Compound of formula (S)-IIc | 12.5% |
| PLGA (75:25) (MW ~9) | 12.5% |
| Propylene carbonate | 52.5% |
| Triacetin | 22.5% |
| BHT | 0.02% |

Example 60

| | |
|---|---|
| Compound of formula (S)-IIc | 12.5% |
| PLGA (50:50) (MW 9) | 12.5% |
| Propylene carbonate | 63.7% |
| Triacetin | 11.3% |
| BHT | 0.02% |

Example 61

| | |
|---|---|
| Compound of formula (S)-IIc | 12.5% |
| PLGA (50:50) (MW ~52) | 12.5% |
| Propylene carbonate | 51.1% |
| Triacetin | 21.9% |
| Poloxamer-124 | 2% |
| BHT | 0.02% |

Example 62

| | |
|---|---|
| Compound of formula (IIc) | 26% |
| PLGA (50:50) (MW ~52) | 1% |
| Propylene carbonate | 50.82% |
| Triacetin | 22.2% |
| BHT | 0.02% |

Example 63

| | |
|---|---|
| Compound of formula (IIc) | 26% |
| PLGA (50:50) (MW 9) | 5% |
| Propylene carbonate | 48.03% |
| Triacetin | 20.95% |
| BHT | 0.02% |

Example 64

| | |
|---|---|
| Compound of formula (IIc) | 26% |
| PLGA (50:50) (MW ~52) | 5% |
| Propylene carbonate | 48.03% |
| Triacetin | 20.95% |

Efficacy Example

Example 65

The following example demonstrates the efficacy of the long-acting injectable compositions of the invention against ectoparasites in companion animals (dogs).

The compositions for the following Treatment Groups in Table 1 were prepared. Except for the dose, all values in the table are % (w/w):

TABLE 1

| Group | Compound of Formula (S)-IIc | PLGA (75:25) (MW ~9)[1] | PLGA (75:25) (MW ~52)[1] | PC[2] | Tri-acetin | P-124[3] | BHT | Dose (mg/kg) |
|---|---|---|---|---|---|---|---|---|
| 1 | — | — | 12.5 | 61.21 | 26.27 | — | 0.02 | N/A |
| 2 | 12.5 | — | 12.5 | 51.05 | 21.92 | 2 | 0.02 | 12.5 |
| 3 | 12.5 | — | 12.5 | 52.46 | 22.52 | — | 0.02 | 12.5 |
| 4 | 12.5 | — | 15 | 49.31 | 21.17 | 2 | 0.02 | 12.5 |
| 5 | 12.5 | 15 | — | 50.71 | 21.77 | — | 0.02 | 12.5 |
| 6 | 12.5 | — | 12.5 | 51.06 | 21.92 | 2 | 0.02 | 6.25 |

[1]Weight average molecular weight (kDa)
[2]Propylene carbonate
[3]Poloxamer 124

Thirty beagles were studied to determine the effectiveness of the inventive extended release injectable compositions (compositions of Treatment Groups 2-6 above) against fleas (*Ctenocephalides felis*) for at least 180 days after treatment.

Six treatment groups of five dogs each were formed, each treatment group received one injection of the extended release formulation identified above (Group 1 being the control). All dogs were injected one at day 0. Each animal was infested with *C. felis* on Day 6, 34, 69 and 111. Fleas were counted upon removal on Days 7, 35, 70 and 112. Fleas were also counted for Groups 5 and 6 on Day 190. Percent reduction (also referred as efficacy) against fleas was 100% for all treatment Groups (i.e., Groups 2-6) through Day 112. Percent reduction on Day 190 against fleas was 96.9% for Group 5 and 100.0% for Group 6.

Blood Plasma Levels

Further, the plasma concentrations of the isoxazoline compound of formula (S)-IIc was determined by collecting a single blood samples for each of the animals as specific time points after the single subcutaneous rejection of the extended release compositions identified above.

The concentration of the compound of formula (S)-IIc was found to be above 50 ng/ml 183 days after treatment, thereby indicating that the compositions of Treatment Groups 2-6 would be effective against fleas and ticks.

The invention is further described by the following numbered paragraphs:

#1. An extended release injectable composition for the treatment or prevention of parasite infections or infestations in an animal comprising an antiparasitic effective amount of at least one isoxazoline active agent, a pharmaceutically acceptable polymer and a solvent or mixture of solvents.

#2 The extended release injectable composition according to paragraph #1 comprising:

a) an antiparasitic effective amount of at least one isoxazoline active agent, which is:

i) an isoxazoline compound of formula (I):

(I)

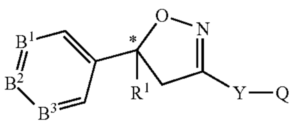

wherein:

$B^1$, $B^2$ and $B^3$ are each independently C—R or N;

each R is independently H, halogen, cyano, —$NO_2$, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino or alkoxycarbonyl;

$R^1$ is $C_1$-$C_3$alkyl or $C_1$-$C_3$haloalkyl;

Y is an optionally substituted phenylene, naphthylene, indanylene, a 5- or 6-membered heteroarylene or an 8-10-membered fused heterobicyclylene, wherein the optional substituents are selected from the group consisting of halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, CN or $NO_2$ and $NH_2$—C(═S)—;

Q is X—$NR^2R^3$, the group (—$CH_2$—)(—$CH_2$—)N—$R^3$, OH, $NH_2$, alkoxy, haloalkoxy, alkylamino, haloalkylamino, dialkylamino, halodialkylamino, thiol, alkylthio, haloalkylthio, alkylsulfinyl, haloalkylsulfinyl, alkylsulfonyl, haloalkylsulfonyl, or an optionally substituted 5- or 6-membered carbocyclyl, heterocyclyl or heteroaryl ring;

X is $(CH_2)_n$, $CH(CH_3)$, CH(CN), C(═O) or C(═S);

$R^2$ is H, alkyl, alkenyl, alkynyl, cycloalkyl, alkylcycloalkyl, cycloalkylalkyl, alkylcarbonyl or alkoxycarbonyl;

$R^3$ is H, $OR^7$, $NR^8R^9$ or $Q^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^4$; or $R^2$ and $R^3$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;

each $R^4$ is independently halogen; alkyl, cycloalkyl, alkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —$NH_2$, —CN or —$NO_2$; or $Q^2$ each $R^5$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —$NO_2$;

each $R^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN, —$NO_2$, phenyl or pyridinyl;

$R^7$ is H; or alkyl, alkenyl, alkynyl, cycloalkyl, alkylcycloalkyl or cycloalkylalkyl, each optionally substituted with one of more halogen;

$R^8$ is H, alkyl, alkenyl, alkynyl, cycloalkyl, alkylcycloalkyl, cycloalkylalkyl, alkylcarbonyl or alkoxycarbonyl;

$R^9$ is H; $Q^3$; or alkyl, alkenyl, alkynyl, cycloalkyl, alkylcycloalkyl or cycloalkylalkyl, each optionally substituted with one or more substituents independently selected from $R^4$; or $R^8$ and $R^9$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^5$;

$Q^2$ is independently a phenyl ring or a 5- or 6-membered heterocyclic ring, each ring optionally substituted with one or more substituents independently selected from $R^6$;

$Q^3$ is a phenyl ring or a 5- or 6-membered heterocyclic ring, each ring optionally substituted with one or more substituents independently selected from $R^6$; and n is 0, 1 or 2; and/or ii) an isoxazoline compound of formula (II):

(II)

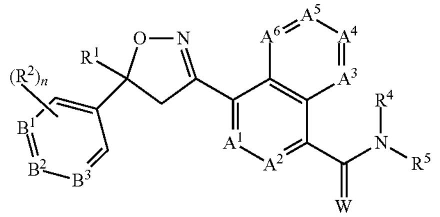

wherein:

$A^1$, $A^2$, $A^3$, $A^4$, $A^5$ and $A^6$ are independently selected from the group consisting of $CR^3$ and N, provided that at most 3 of $A^1$, $A^2$, $A^3$, $A^4$, $A^5$ and $A^6$ are N;

$B^1$, $B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, CN or $NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2; or a pharmaceutically acceptable salt thereof; and/or iii) an isoxazoline compound of formula (III):

(III)

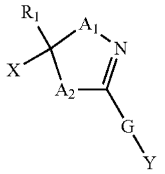

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$A^1$ is oxygen; and $A_2$ is oxygen, $NR_2$ or $CR_7R_8$;

G is G-1 or G-2;

G-1

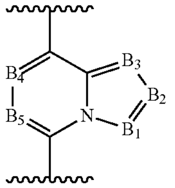

G-2

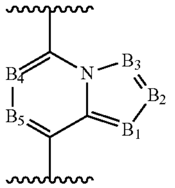

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13;

Y-1

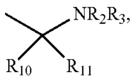

Y-2

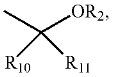

Y-3

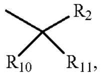

Y-4

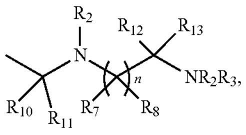

Y-5

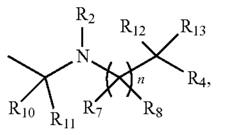

Y-6

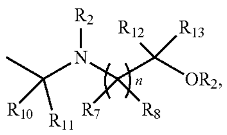

-continued

Y-7

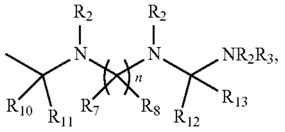

Y-8

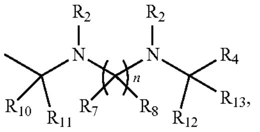

Y-9

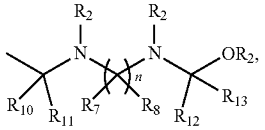

Y-10

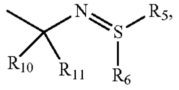

Y-11

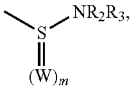

Y-12

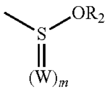

or

Y-13

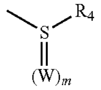

$R_2$, $R_3$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$—$R_{10}OC(O)$—;

$R_4$, $R_5$ and $R_6$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxyalkyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxyalkyl, alkenyl, haloalkenyl, alkynyl or haloalkynyl; or $R_{10}$ together with $R_{11}$ form =O, =S or =$NR_2$; or $R_{12}$ together with $R_{13}$ form =O, =S or =$NR_2$;

W is O, S or $NR_2$;

n is 1-4; and m is 0, 1 or 2; or a pharmaceutically acceptable salt thereof, and/or iv) an isoxazoline compound of formula (IV)

(IV)

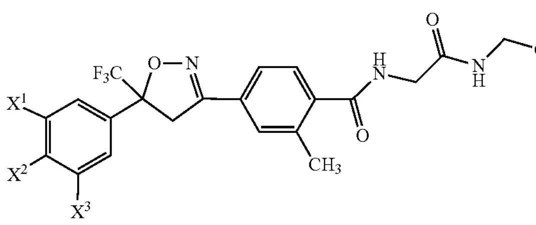

wherein $X^1$, $X^2$ and $X^3$ are independently H, halogen, $C_1$-$C_3$alkyl or $C_1$-$C_3$haloalkyl, or a pharmaceutically acceptable salt thereof; and/or iv) an isoxazoline compound of formula (V)

(V)

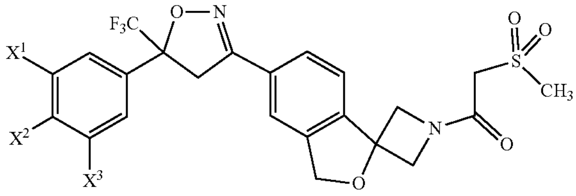

wherein $X^1$, $X^2$ and $X^3$ are independently H, halogen, $C_1$-$C_3$alkyl or $C_1$-$C_3$haloalkyl, or a pharmaceutically acceptable salt thereof; and/or v) an isoxazoline compound of formula (V):

(VI)

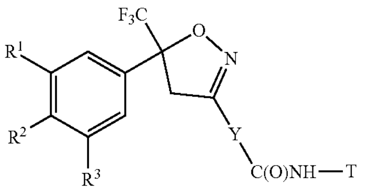

wherein $R^1$, $R^2$ and $R^3$ are independently H, Cl, F or $CF_3$;

Y is the diradical group

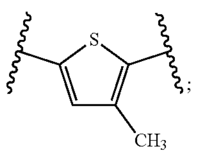 [SMILES: *c1cc(C)c(*)s1]

and

T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof; and/or vi) an isoxazoline compound of formula (VI):

(VII)

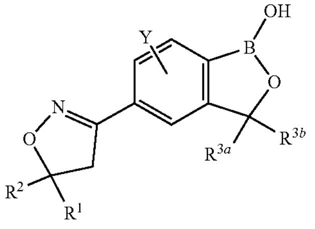

wherein Y is hydrogen, fluoro, chloro or bromo;

$R^1$ is phenyl substituted with 2-4 substituents selected from halogen, methyl, difluoromethyl, trifluoromethyl, methoxy, trifluoromethoxy or trifluoroethoxy;

$R^2$ is methyl, fluoromethyl, trifluoromethyl or perfluoroethyl;

$R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof;

b) at least one pharmaceutically acceptable polymer;

c) at least one solvent or a mixture of solvents;

d) optionally, an antioxidant; and e) optionally at least one pharmaceutically acceptable additive, excipient or mixtures thereof.

#3. The extended release injectable composition according to paragraph #2, wherein the isoxazoline active agent is a compound of formula (II).

#4. The extended release injectable composition according to paragraph #3, wherein in the isoxazoline active agent is a compound of the formula II).

(IIa)

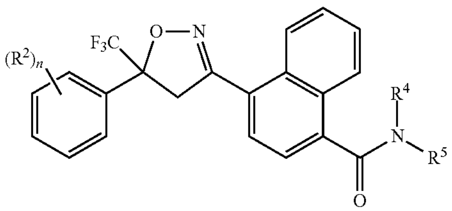

or a pharmaceutically acceptable salt thereof, wherein:

$R^2$ independently is halogen, $C_1$-$C_6$ alkyl or $C_1$-$C_6$ haloalkyl $R^4$ is H or $C_1$-$C_6$ alkyl;

$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl; and n is 0, 1 or 2.

#5. The extended release injectable composition according to paragraph #4, wherein in the isoxazoline active agent is a compound of formula (IIc), (IId), (IIe) or (IIf):

(IIc)

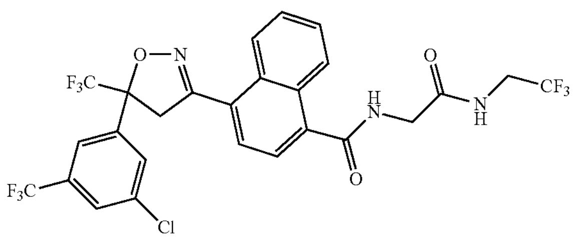

(IId)

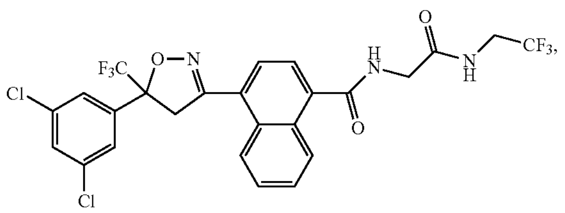

(IIe)

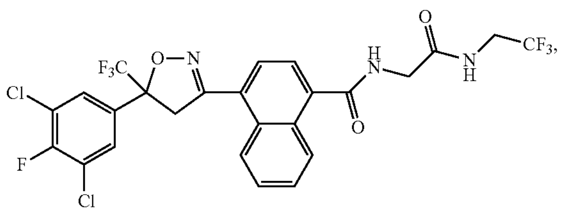

(IIf)

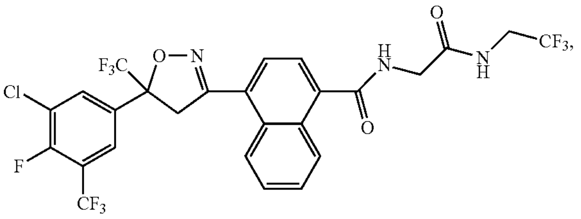

or a pharmaceutically acceptable salt thereof.

#6. The extended release injectable composition according to paragraph #1 or paragraph #2, wherein the isoxazoline active agent is enriched in an enantiomer.

#7. The extended release injectable composition according to paragraph #6, wherein in the isoxazoline active agent is a compound of formula (S)-IIc, (S)-IId, (S)-IIe or (S)-IIf:

(S)-IIc

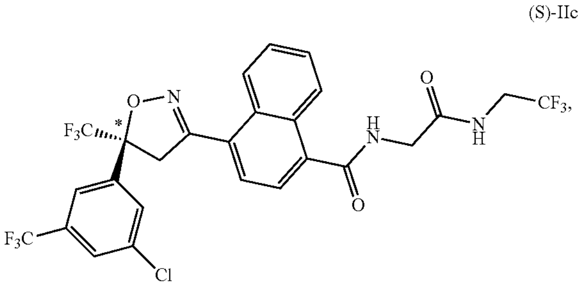

-continued (S)-IId

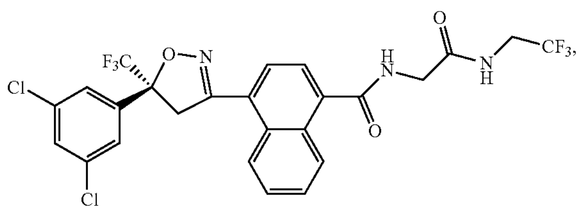

(S)-IIe

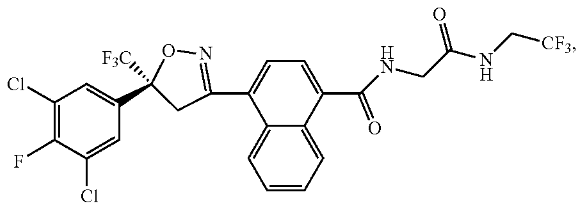

(S)-IIf

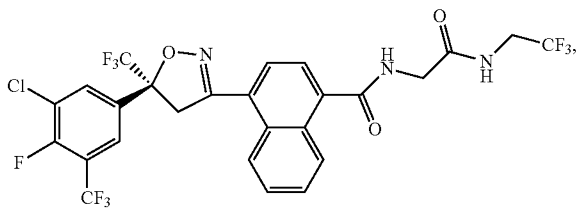

or a pharmaceutically acceptable salt thereof.

#8. The extended release injectable composition according to paragraph #2, wherein the isoxazoline active agent is a compound of formula (III):

(III)

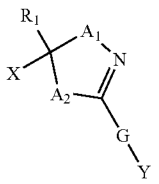

wherein:

$R_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$A^1$ is oxygen; and $A_2$ is oxygen, $NR_2$ or $CR_7R_8$;

G is G-1 or G-2;

G-1

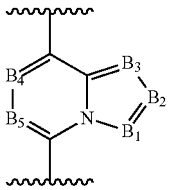

G-2

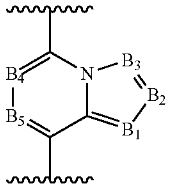

$B_1$, $B_2$, $B_3$, $B_4$ and $B_5$ are independently N or C—$R_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$; or Y is Y-1, Y-2, Y-3, Y-4, Y-5, Y-6, Y-7, Y-8, Y-9, Y-10, Y-11, Y-12 or Y-13;

Y-1

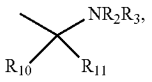

Y-2

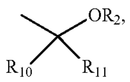

Y-3

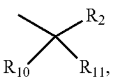

Y-4

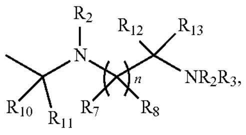

Y-5

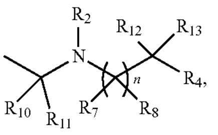

Y-6

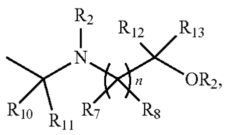

-continued

Y-7

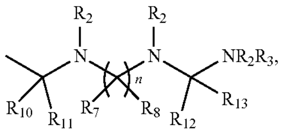

Y-8

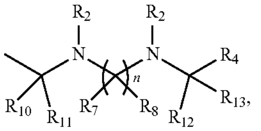

Y-9

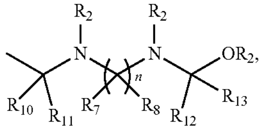

Y-10

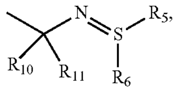

Y-11

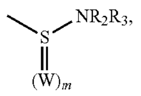

Y-12

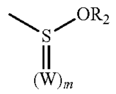

or

Y-13

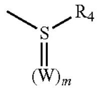

$R_2$, $R_3$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$—$R_{10}OC(O)$—;

$R_4$, $R_5$ and $R_6$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, aryl or heteroaryl;

$R_7$ and $R_8$ are independently hydrogen, alkyl, haloalkyl, thioalkyl, alkylthioalkyl, hydroxyalkyl, alkoxyalkyl, alkenyl, haloalkenyl, alkynyl or haloalkynyl;

$R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —$NO_2$;

$R_{10}$, $R_{11}$, $R_{12}$ and $R_{13}$ are each independently hydrogen, alkyl, haloalkyl, thioalkyl, alkylthioalkyl, hydroxyalkyl, alkoxyalkyl, alkenyl, haloalkenyl, alkynyl or haloalkynyl; or $R_{10}$ together with $R_{11}$ form =O, =S or =$NR_2$; or
$R_{12}$ together with $R_{13}$ form =O, =S or =$NR_2$;
W is O, S or $NR_2$;
n is 1-4; and
m is 0, 1 or 2; or a pharmaceutically acceptable salt thereof.

#9. The extended release injectable composition according to paragraph #8 wherein isoxazoline agent is a compound of formulae III-1.001 to III-1.025 or III-2.00-III-2.018:

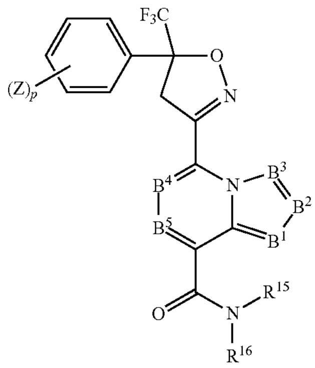

Compounds III-1.001 to III-1.025

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 1.001 | 3,5-$Cl_2$ | C—H | C—H | C—H | C—H | N | H | $CH_2C(O)NHCH_2CF_3$ |
| 1.002 | 3,5-$Cl_2$ | C—H | C—H | C—H | C—H | N | H | $CH_2CF_3$ |
| 1.003 | 3,5-$(CF_3)_2$ | C—H | C—H | C—H | C—H | N | CH3 | $CH_2CO_2CH_3$ |
| 1.004 | 3,5-$(CF_3)_2$ | C—H | C—H | C—H | C—H | N | CH3 | $CH_2CO_2H$ |
| 1.005 | 3,5-$(CF_3)_2$ | C—H | C—H | C—H | C—H | N | CH3 | $CH_2C(O)NHCH_2CF_3$ |
| 1.006 | 3,5-$(CF_3)_2$ | C—H | C—H | C—H | C—H | N | H | $CH_2C(O)NHCH_2CF_3$ |
| 1.007 | 3,5-$(CF_3)_2$ | C—H | C—H | C—H | C—H | N | H | $CH_2CH_2SCH_3$ |
| 1.008 | 3,5-$(CF_3)_2$ | C—H | C—H | C—H | C—H | C—H | H | $CH_2C(O)NHCH_2CF_3$ |
| 1.009 | 3,5-$(CF_3)_2$ | C—H | C—H | C—H | C—H | C—H | H | $CH_2CH_2SCH_3$ |
| 1.010 | 3,5-$(CF_3)_2$ | C—H | C—H | C—H | C—H | C—H | H | $CH_2CF_3$ |
| 1.011 | 3,5-$Cl_2$ | C—H | C—H | C—H | C—H | C—H | H | $CH_2C(O)NHCH_2CF_3$ |
| 1.012 | 3,5-$Cl_2$ | C—H | C—H | C—H | C—H | C—H | H | $CH_2CF_3$ |
| 1.013 | 3,5-$Cl_2$ | C—H | C—H | C—H | C—H | C—H | H | $CH_2CH_2SCH_3$ |
| 1.014 | 3-Cl,5-$CF_3$ | C—H | C—H | C—H | C—H | C—H | H | $CH_2C(O)NHCH_2CF_3$ |
| 1.015 | 3-Cl,5-$CF_3$ | C—H | C—H | C—H | C—H | C—H | H | $CH_2CF_3$ |
| 1.016 | 3-Cl,5-$CF_3$ | C—H | C—H | C—H | C—H | C—H | H | $CH_2CH_2SCH_3$ |
| 1.017 | 3,5-$Cl_2$ | C—H | C—H | C—Me | C—H | C—Me | H | $CH_2C(O)NHCH_2CF_3$ |
| 1.018 | 3,5-$Cl_2$ | C—H | C—H | C—Me | C—H | C—Me | H | $CH_2CF_3$ |
| 1.019 | 3,5-$Cl_2$ | C—H | C—H | C—Me | C—H | C—Me | H | $CH_2CH_2SCH_3$ |
| 1.020 | 3,5-$(CF_3)_2$ | C—H | C—H | C—Me | C—H | C—Me | H | $CH_2C(O)NHCH_2CF_3$ |
| 1.021 | 3,5-$(CF_3)_2$ | C—H | C—H | C—Me | C—H | C—Me | H | $CH_2CF_3$ |
| 1.022 | 3,5-$(CF_3)_2$ | C—H | C—H | C—Me | C—H | C—Me | H | $CH_2CH_2SCH_3$ |
| 1.023 | 3-Cl,5-$CF_3$ | C—H | C—H | C—Me | C—H | C—Me | H | $CH_2C(O)NHCH_2CF_3$ |
| 1.024 | 3-Cl,5-$CF_3$ | C—H | C—H | C—Me | C—H | C—Me | H | $CH_2CF_3$ |
| 1.025 | 3-Cl,5-$CF_3$ | C—H | C—H | C—Me | C—H | C—Me | H | $CH_2CH_2SCH_3$ |

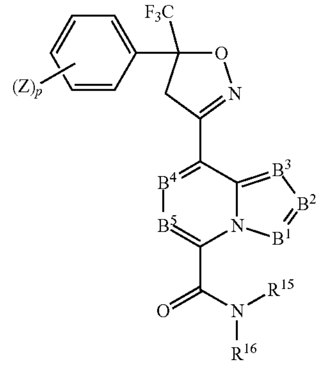

Compounds III-2.001 to III-2.018

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 2.001 | 3,5-$Cl_2$ | C—H | C—H | N | C—H | C—H | H | $CH_2C(O)NHCH_2CF_3$ |
| 2.002 | 3,5-$Cl_2$ | C—H | C—H | N | C—H | C—H | H | $CH_2CF_3$ |
| 2.003 | 3,5-$Cl_2$ | C—H | C—H | N | C—H | C—H | H | $CH_2CH_2SCH_3$ |
| 2.004 | 3,5-$(CF_3)_2$ | C—H | C—H | N | C—H | C—H | H | $CH_2C(O)NHCH_2CF_3$ |
| 2.005 | 3,5-$(CF_3)_2$ | C—H | C—H | N | C—H | C—H | H | $CH_2CF_3$ |
| 2.006 | 3,5-$(CF_3)_2$ | C—H | C—H | N | C—H | C—H | H | $CH_2CH_2SCH_3$ |
| 2.007 | 3-Cl,5-$CF_3$ | C—H | C—H | N | C—H | C—H | H | $CH_2C(O)NHCH_2CF_3$ |
| 2.008 | 3-Cl,5-$CF_3$ | C—H | C—H | N | C—H | C—H | H | $CH_2CF_3$ |
| 2.009 | 3-Cl,5-$CF_3$ | C—H | C—H | N | C—H | C—H | H | $CH_2CH_2SCH_3$ |
| 2.010 | 3,5-$Cl_2$ | C—H | C—H | C—H | C—H | C—H | H | $CH_2C(O)NHCH_2CF_3$ |
| 2.011 | 3,5-$Cl_2$ | C—H | C—H | C—H | C—H | C—H | H | $CH_2CF_3$ |
| 2.012 | 3,5-$Cl_2$ | C—H | C—H | C—H | C—H | C—H | H | $CH_2CH_2SCH_3$ |
| 2.013 | 3,5-$(CF_3)_2$ | C—H | C—H | C—H | C—H | C—H | H | $CH_2C(O)NHCH_2CF_3$ |
| 2.014 | 3,5-$(CF_3)_2$ | C—H | C—H | C—H | C—H | C—H | H | $CH_2CF_3$ |
| 2.015 | 3,5-$(CF_3)_2$ | C—H | C—H | C—H | C—H | C—H | H | $CH_2CH_2SCH_3$ |
| 2.016 | 3-Cl,5-$CF_3$ | C—H | C—H | C—H | C—H | C—H | H | $CH_2C(O)NHCH_2CF_3$ |
| 2.017 | 3-Cl,5-$CF_3$ | C—H | C—H | C—H | C—H | C—H | H | $CH_2CF_3$ |
| 2.018 | 3-Cl,5-$CF_3$ | C—H | C—H | C—H | C—H | C—H | H | $CH_2CH_2SCH_3$ |

or a pharmaceutically acceptable salt thereof.

#10. The extended release injectable composition according to paragraph #2, wherein isoxazoline active agent is a compound of formula (IVa):

(IVa)

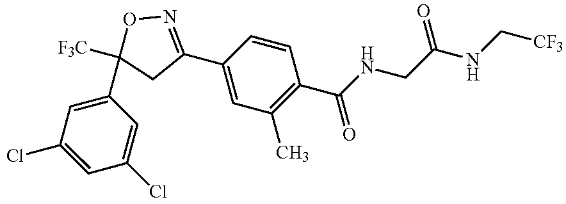

or a pharmaceutically acceptable salt thereof.

#11. The extended release injectable composition according to paragraph #2, wherein isoxazoline compound is a compound of formula (Va):

(Va)

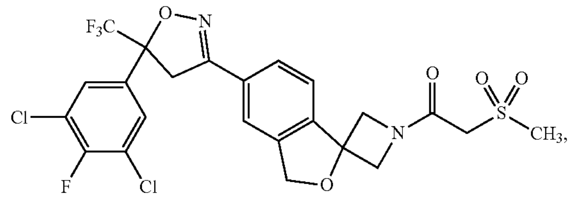

or a pharmaceutically acceptable salt thereof.

#12. The extended release injectable composition according to paragraph #2, wherein isoxazoline compound is a compound of formula (VIa):

(VIa)

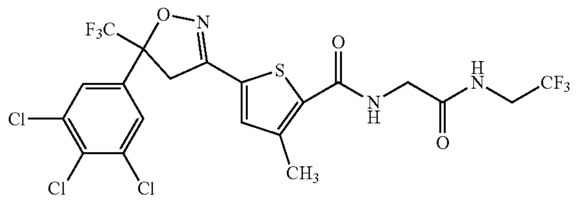

or a pharmaceutically acceptable salt thereof.

#13. The extended release composition of any one of paragraph #1 to paragraph #12, wherein the pharmaceutically acceptable polymer is selected from the group consisting of polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, copolymers thereof or terpolymers thereof, or combinations or mixtures thereof.

#14. The extended release composition according to paragraph #13, wherein the pharmaceutically acceptable polymer is a copolymer of polylactides and polyglycolides.

#15. The extended release composition according to paragraph #13, wherein the pharmaceutically acceptable polymer is a polycaprolactone, a polyamide, a polyanhydride or a polyorthoester.

#16. The extended release injectable composition of any one of paragraph #1 to paragraph #15, wherein the solvent is an alcohol, a liquid polyethylene glycol, propylene glycol, glycerol, a glycerol ester, a cyclic carbonate, 2-pyrrolidone, N-methylpyrrolidone, dimethyl isosorbide, dimethylacetamide, glycerol formal, a triglyceride, a propylene glycol diester, a poloxamer, or a mixture of at least two of these solvents.

#17. The extended release injectable composition of any one of paragraph #1 to paragraph #15, wherein the solvent is a mixture of a water-miscible solvent and a water-immiscible solvent.

#18. The extended release injectable composition according to paragraph #1 comprising:

a) about 5 to about 20% (w/w) or about 15 to 30% (w/w) of an isoxazoline compound of Formula (II):

(II)

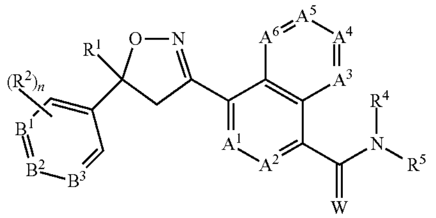

wherein:

$A^1$, $A^2$, $A^3$, $A^4$, $A^5$ and $A^6$ are independently selected from the group consisting of $CR^3$ and N, provided that at most 3 of $A^1$, $A^2$, $A^3$, $A^4$, $A^5$ and $A^6$ are N;

$B^1$, $B^2$ and $B^3$ are independently selected from the group consisting of $CR^2$ and N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —$NO_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —$NO_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —$NH_2$, —CN or —$NO_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —$NO_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —$NO_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —$NO_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$; $Q^3$ is a phenyl ring or a 5- or 6-membered heterocyclic ring, each ring optionally substituted with one or more substituents independently selected from $R^9$; and n is 0, 1 or 2 or a pharmaceutically acceptable salt thereof, b) about 1 to about 30% (w/w) or 1 to about 20% (w/w) of a pharmaceutically acceptable polymer which is a polycaprolactone, a polylactide, a polyglycolide or a polylactide and polyglycolide copolymer;

c) about 40 to about 85% (w/w) of solvent selected from a cyclic carbonate, dimethylisosorbide, a poloxamer, a glycerol ester, a triglyceride, a liquid polyethylene glycol and an alcohol, or a mixture thereof, d) optionally, about 0.01% to about 2.0% (w/w) of an antioxidant; and e) optionally about 0.01% to about 5.0% (w/w) of a pharmaceutically acceptable additive, excipient or mixtures thereof.

#19. The extended release injectable formulation according to paragraph #18, wherein the compound is a compound of formula (IIc):

(IIc)

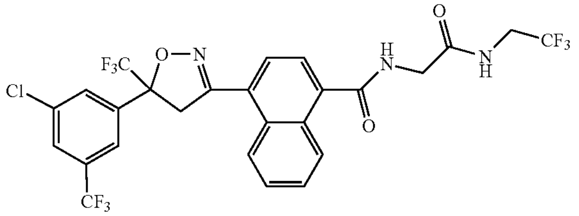

or a pharmaceutically acceptable salt thereof.

#20. The extended release injectable formulation according to paragraph #18, wherein the isoxazoline compound is:

(S)-IIc

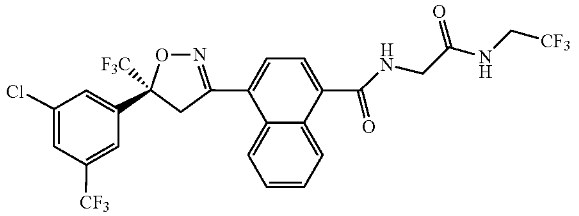

or a pharmaceutically acceptable salt thereof.

#21. The extended release formulation according to any one of paragraph #s 1-20, which further comprise an effective amount at least one additional pharmaceutically active agent.

#22. The extended release formulation according to paragraph #21, wherein the additional pharmaceutically active agent is a macrocyclic lactone.

#23. The extended release formulation according to paragraph #22, wherein the macrocyclic lactone is abamectin, dimadectin, doramectin, emamectin, eprinomectin, ivermectin, latidectin, lepimectin, selamectin, milbemectin, milbemycin D, milbemycin oxime, moxidectin or nemadectin.

#24. A method for treating or preventing parasites in an animal in need thereof for a period of 3 to 12 months which comprises administering the long acting injectable formulation according to paragraph #1 to said animal.

#25. The method according to paragraph #24 wherein the animal is a dog, cat, sheep or cattle.

#26. The method according to paragraph #24 wherein the parasites are treated or prevented for about 5 to 6 months.

#27. The method according to paragraph #24 wherein the parasites are treated or prevented for about 6 months or longer.

#28. The method according to paragraph #24 wherein the parasites are fleas and/or ticks.

#29. The use of an isoxazoline in the preparation of an extended release injectable formulation for the treatment or prevention of a parasite infestation or infection on or in an animal.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. An extended release injectable composition for the treatment or prevention of a parasitic infestation or infection in an animal comprising:

a) 5 to 20% (w/w) of an isoxazoline compound of Formula (IIc):

(IIc)

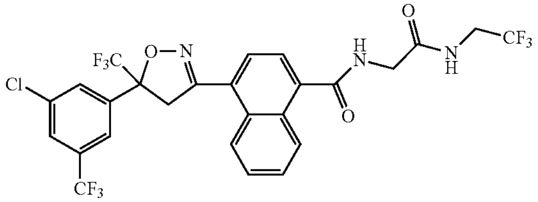

or a pharmaceutically acceptable salt thereof;

b) about 8% (w/w) to about 20% (w/w) of a pharmaceutically acceptable polymer which is a copolymer of polylactides and polyglycolides that has a lactide to glycolide ratio of 70:30 to 80:20 (weight:weight);

c) about 40 to about 85% (w/w) of a solvent which is a mixture comprising propylene carbonate and triacetin wherein the ratio of propylene carbonate to triacetin is about 2:1 to about 6:1 (w/w);

d) optionally, about 0.01% to 2.0% (w/w) of an antioxidant;

e) optionally, about 0.1% to 10% (w/w) of a surfactant; and f) optionally, about 0.01 to 5.0% (w/w) of a pharmaceutically acceptable additive, excipient or mixtures thereof.

2. The extended release injectable composition according to claim 1, wherein the isoxazoline compound is enriched in an enantiomer.

3. The extended release injectable composition according to claim 2, wherein in the isoxazoline compound is:

(S)-IIc

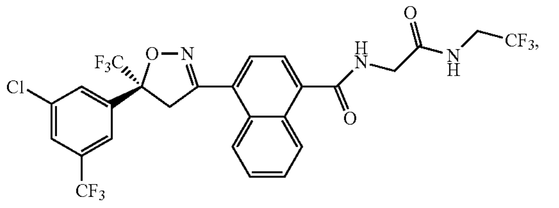

or a pharmaceutically acceptable salt thereof.

4. The extended release injectable composition according to claim 1 wherein the solvent mixture further comprises a poloxamer.

5. The extended release injectable composition according to claim 4, which comprises about 0.5 to about 20% (w/w) of the poloxamer.

6. The extended release injectable composition according to claim 1 wherein the ratio of the copolymer of polylactides and polyglycolides to the isoxazoline compound is about 1.5:1 to about 1:1.5 (weight:weight).

7. The extended release injectable composition according to claim 6, wherein the weight average molecular weight of the copolymer of polylactides and polyglycolides is from about 5 to about 20 kDa.

8. The extended release injectable composition according to claim 1, which further comprises an effective amount at least one additional pharmaceutically active agent.

9. The extended release injectable composition according to claim 3 wherein the additional pharmaceutically active agent is a macrocyclic lactone.

10. The extended release injectable composition according to claim 9, wherein the macrocyclic lactone is abamectin, dimadectin, doramectin, emamectin, eprinomectin, ivermectin, latidectin, lepimectin, selamectin, milbemectin, milbemycin D, milbemycin oxime, moxidectin or nemadectin.

11. A method for treating an ectoparasitic infestation in an animal in need thereof comprising administering a long acting injectable composition to said animal, wherein the long acting injectable composition comprises:

a) 5 to 20% (w/w) of an isoxazoline compound of Formula (IIc):

(IIc)

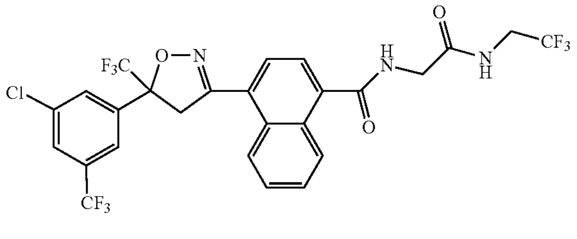

or a pharmaceutically acceptable salt thereof;

b) about 8% (w/w) to about 20% (w/w) of a pharmaceutically acceptable polymer which is a copolymer of polylactides and polyglycolides that has a lactide to glycolide ratio of 460 70:30 to 80:20 (weight:weight);

c) about 40 to about 85% (w/w) of a solvent which is a mixture comprising propylene carbonate and triacetin wherein the ratio of propylene carbonate to triacetin is about 2:1 to about 6:1 (w/w);

d) optionally, about 0.01% to 2.0% (w/w) of an antioxidant;

e) optionally, about 0.1% to 10% (w/w) of a surfactant; and f) optionally, about 0.01 to 5.0% (w/w) of a pharmaceutically acceptable additive, excipient or mixtures thereof, wherein the ectoparasitic infestation is treated for about 5 to 6 months.

12. The method according to claim 11 wherein the animal is a dog, cat, sheep or cattle.

13. The method according to claim 11 wherein the ectoparasitic infestation is a flea and/or tick infestation.

14. The method according to claim 11, wherein the isoxazoline compound is:

(S)-IIc

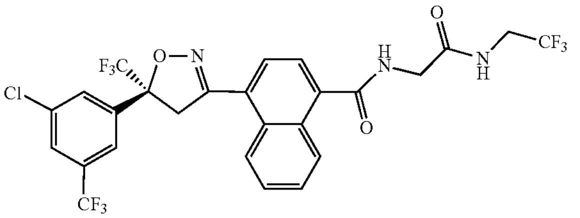

or a pharmaceutically acceptable salt thereof.

15. The method according to claim 14 wherein the animal is a dog, cat, sheep or cattle.

16. The method according to claim 14 wherein the ectoparasitic infestation is a flea and/or tick infestation.

17. The method according to claim 11 wherein the solvent mixture further comprises a poloxamer.

18. The method according to claim 17 which comprises about 0.5 to about 20% (w/w) of the poloxamer.

19. The method according claim 11, wherein the ratio of the copolymer of polylactides and polyglycolides to the isoxazoline compound or a pharmaceutically acceptable salt thereof is about 1.5:1 to about 1:1.5 (weight:weight).

20. The method according to claim 11, wherein the weight average molecular weight of the copolymer of polylactides and polyglycolides is from about 5 to about 20 kDa.

21. The method according to claim 11, further comprising an effective amount of at least one additional pharmaceutically active agent.

22. The method according to claim 21, wherein the additional pharmaceutically active agent is a macrocyclic lactone.

23. The method according to claim 22, wherein the macrocyclic lactone is selected from the group consisting of abamectin, dimadectin, doramectin, emamectin, eprinomectin, ivermectin, latidectin, lepimectin, selamectin, milbemectin, milbemycin D, milbemycin oxime, moxidectin or nemadectin.

24. The method according to claim 11, comprising 10 to 20% (w/w) of the isoxazoline compound of Formula (IIc).

25. The method according to claim 11, comprising about 60 to about 85% (w/w) of the solvent.

26. The method according to claim 11, wherein the ratio of propylene carbonate to triacetin is about 2:1 to about 3:1 (w/w).

27. The method according to claim 11, comprising 10 to 20% (w/w) of the isoxazoline compound of Formula (IIc), and about 60 to about 85% (w/w) of the solvent, wherein the ratio of propylene carbonate to triacetin is about 2:1 to about 3:1 (w/w).

* * * * *